(12) United States Patent
Luo

(10) Patent No.: US 11,357,780 B2
(45) Date of Patent: Jun. 14, 2022

(54) METHODS AND COMPOSITIONS RELATING TO THE INHIBITION OF IP6K1

(71) Applicant: THE CHILDREN'S MEDICAL CENTER CORPORATION, Boston, MA (US)

(72) Inventor: Hongbo R. Luo, Wellesley, MA (US)

(73) Assignee: THE CHILDREN'S MEDICAL CENTER CORPORATION, Boston, MA (US)

( * ) Notice: Subject to any disclaimer, the term of this patent is extended or adjusted under 35 U.S.C. 154(b) by 84 days.

(21) Appl. No.: 16/978,797

(22) PCT Filed: Mar. 12, 2019

(86) PCT No.: PCT/US2019/021741
§ 371 (c)(1),
(2) Date: Sep. 8, 2020

(87) PCT Pub. No.: WO2019/194939
PCT Pub. Date: Oct. 10, 2019

(65) Prior Publication Data
US 2021/0046080 A1   Feb. 18, 2021

Related U.S. Application Data

(60) Provisional application No. 62/651,364, filed on Apr. 2, 2018.

(51) Int. Cl.
*A61K 31/52* (2006.01)
*A61P 11/00* (2006.01)
*A61P 31/04* (2006.01)
*A61K 45/06* (2006.01)

(52) U.S. Cl.
CPC .............. *A61K 31/52* (2013.01); *A61K 45/06* (2013.01)

(58) Field of Classification Search
CPC ........... A61K 31/52; A61P 11/00; A61P 31/04
USPC ....................................................... 51/263.4
See application file for complete search history.

(56) References Cited

U.S. PATENT DOCUMENTS

2016/0354378 A1   12/2016   Kim et al.

FOREIGN PATENT DOCUMENTS

WO    2017098467 A1    6/2017

OTHER PUBLICATIONS

Burton et al., "Are inositol pyrophosphates signalling molecules?." Journal of Cellular Physiology 220(1):8-15 (2009).
Chakraborty et al., "HSP90 regulates cell survival via inositol hexakisphosphate kinase-2." PNAS 105(4):1134-1139 (2008).
Ghoshal et al. "TNP [N2-(m-Trifluorobenzyl), N6-(p-nitrobenzyl)purine] ameliorates died induced obesity and insulin resistance via inhibition of the IP6K1 pathway." Mol Metab. 5(10): 903-917 (2016).
Glennon et al., "Turnover of inositol pentakisphosphates, inositol hexakisphosphate and diphosphoinositol polyphosphates in primary cultured hepatocytes." Biochemical Journal 293(2):583-590 (1993).
Hou et al. "Inhibition of IP6K1 suppresses neutrophil-mediated pulmonary damage in bacterial pneumonia." Sci Transl Med. 10(435): 1-25 (2018).
Menniti et al., "Turnover of inositol polyphosphate pyrophosphates in pancreatoma cells." Journal of Biological Chemistry 268(6):3850-3856 (1993).
Prasad et al., "Inositol hexakisphosphate kinase 1 regulates neutrophil function in innate immunity by inhibiting phosphatidylinositol-(3, 4, 5)-trisphosphate signaling." Nature Immunology 12(8):752-760 (2011).
Shears "Diphosphoinositol polyphosphates: metabolic messengers?." Molecular Pharmacology 76(2):236-252 (2009).
Shears "How versatile are inositol phosphate kinases?." Biochemical Journal 377(2):265-280 (2004).
Stephens et al., "The detection, purification, structural characterization, and metabolism of diphosphoinositol pentakisphosphate (s) and bisdiphosphoinositol tetrakisphosphate (s)." Journal of Biological Chemistry 268(6):4009-4015 (1993).

*Primary Examiner* — Raymond J Henley, III
(74) *Attorney, Agent, or Firm* — Nixon Peabody LLP; David S. Resnick; Nicole D. Kling

(57) ABSTRACT

The technology described herein is directed to methods of treating lung infections and/or lung inflammation (e.g, pneumonia) by inhibiting IP6K1.

12 Claims, 29 Drawing Sheets

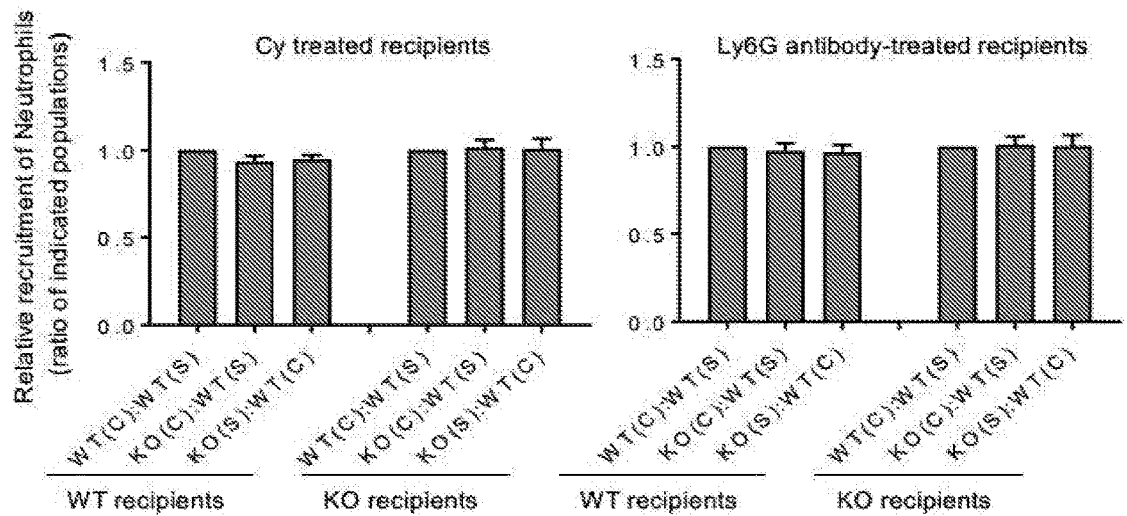
Fig. 2L
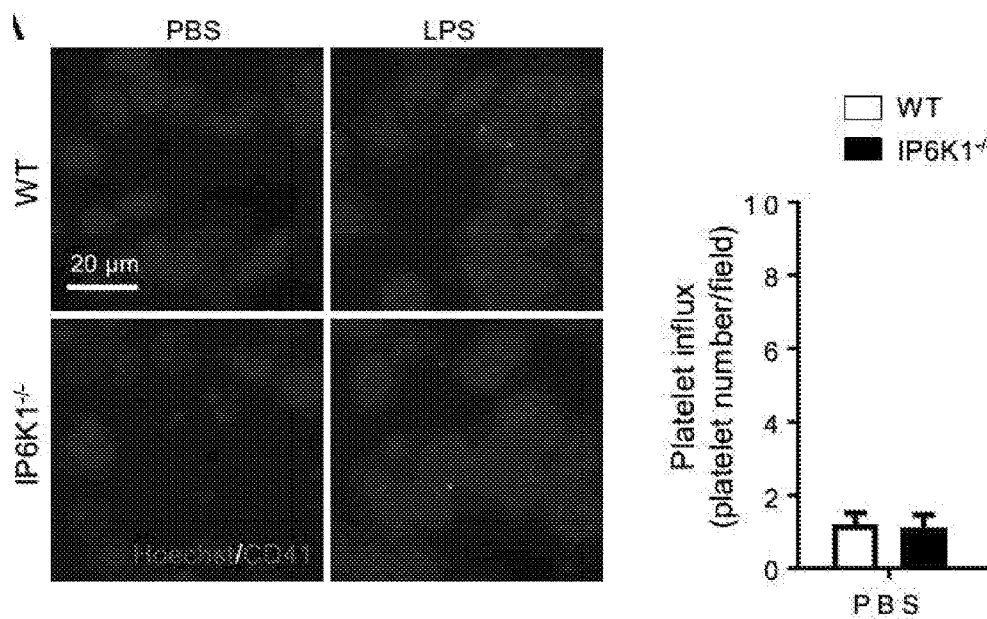
Fig. 3A
Fig. 3B

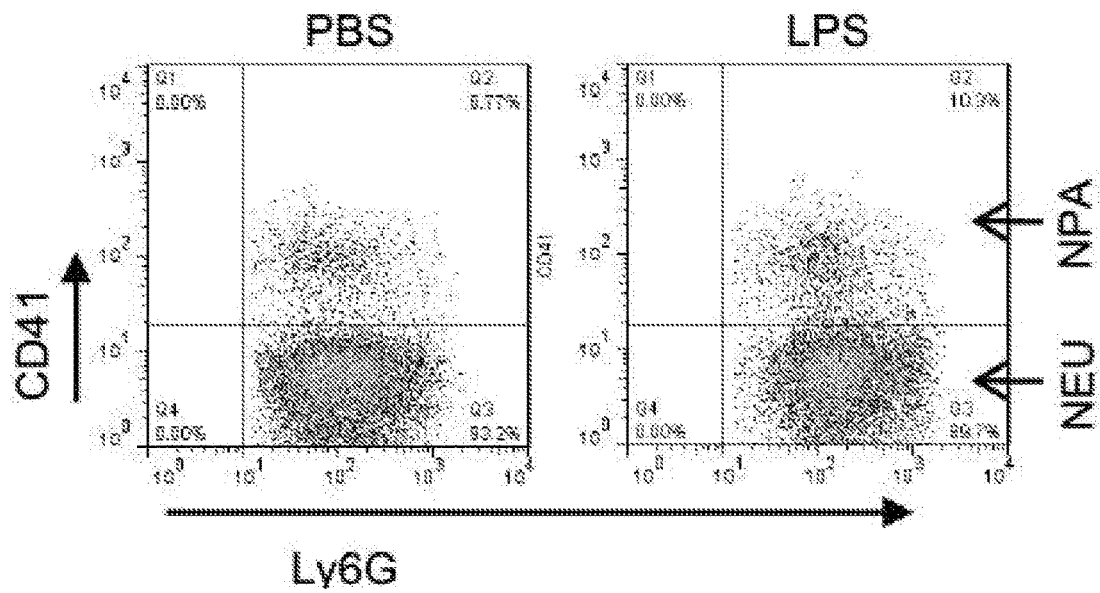
Fig. 3F
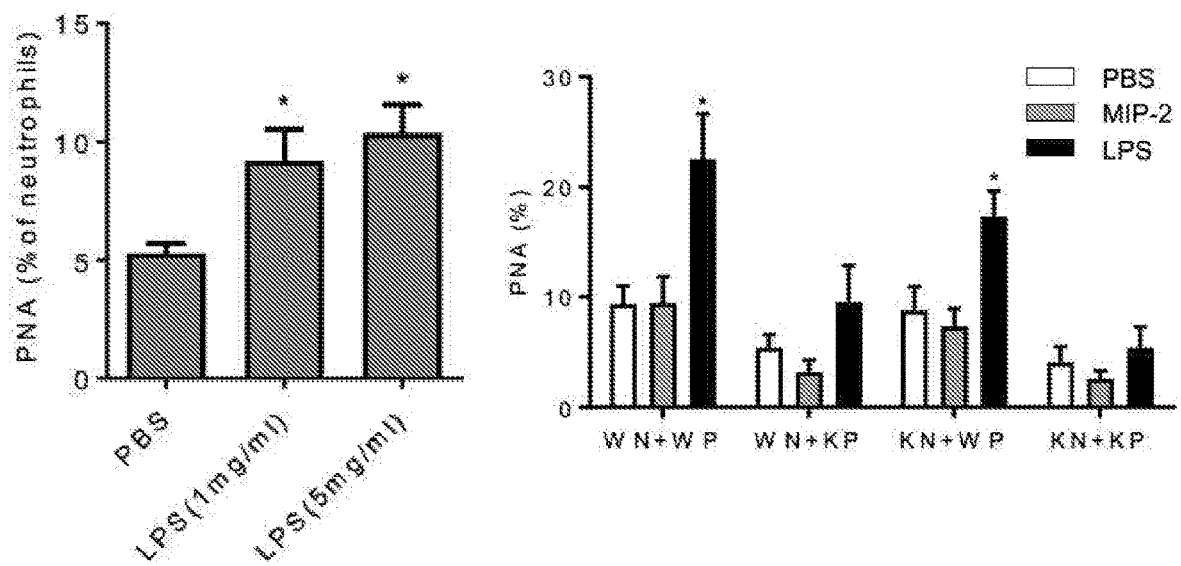
Fig. 3G
Fig. 3H

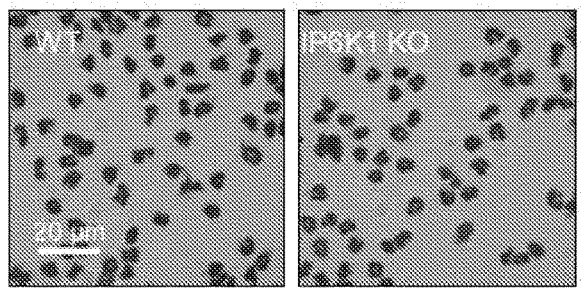
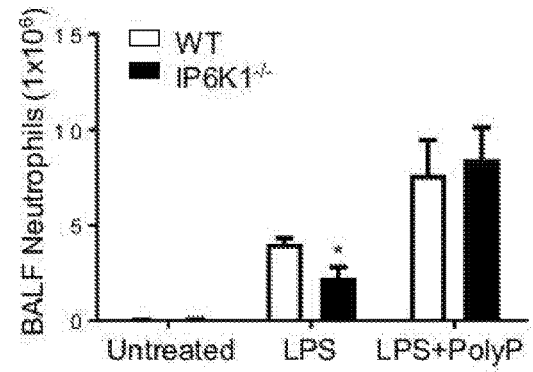
Fig. 4F
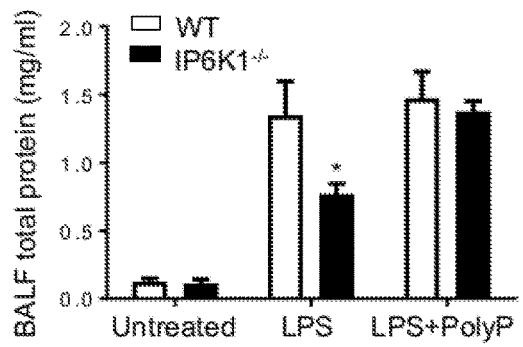
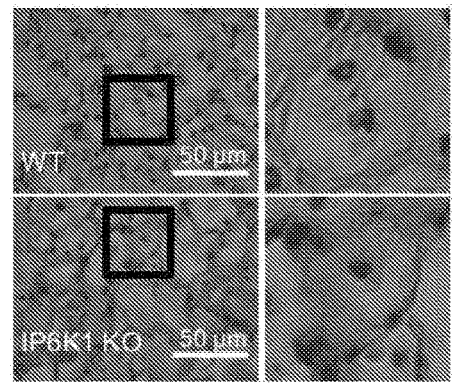
Fig. 4G
Fig. 4H
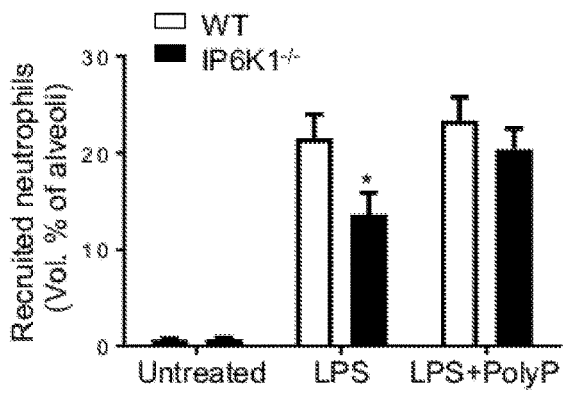
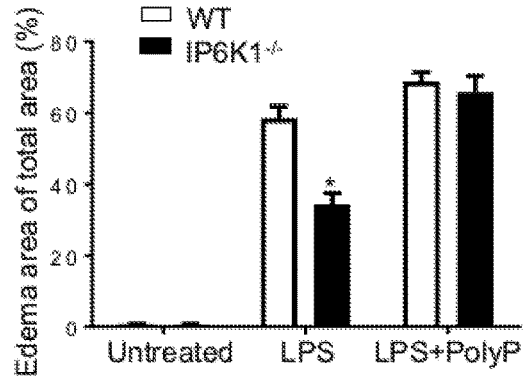
Fig. 4I
Fig. 4J

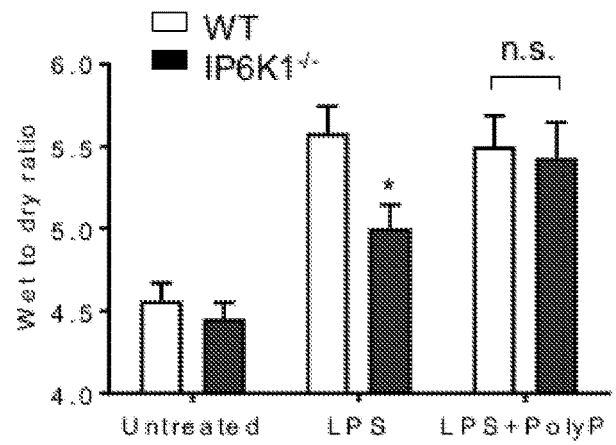
Fig. 4K
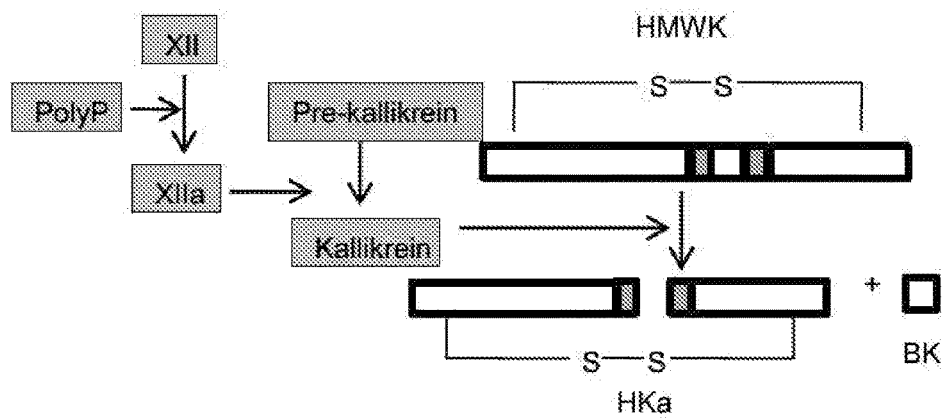
Fig. 5A
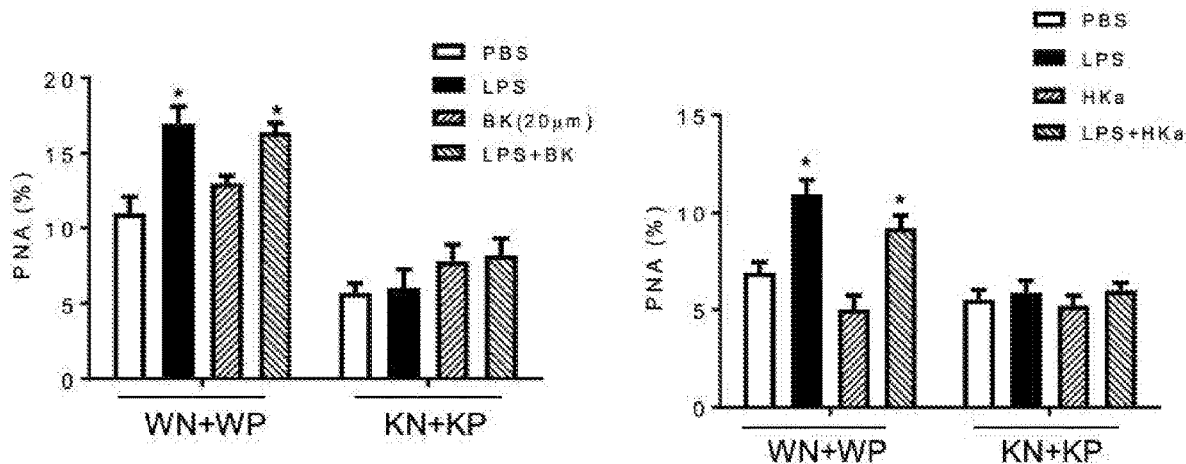
Fig. 5B
Fig. 5C

METHODS AND COMPOSITIONS RELATING TO THE INHIBITION OF IP6K1

CROSS-REFERENCE TO RELATED APPLICATIONS

This application is a 35 U.S.C. § 371 National Phase Entry Application of International Application No. PCT/US2019/021741 filed Mar. 12, 2019, which designates the U.S. and claims benefit under 35 U.S.C. § 119(e) of U.S. Provisional Application No. 62/651,364 filed Apr. 2, 2018, the contents of which are incorporated herein by reference in their entireties.

GOVERNMENT SUPPORT

This invention was made with government support under Grant Nos. R01AI103142, R01HL092020, and P01 HL095489 awarded by the National Institutes of Health. The government has certain rights in the invention.

TECHNICAL FIELD

The technology described herein relates to the treatment of lung diseases related to or involving neutrophil accumulation, e.g, pneumonia.

BACKGROUND

In view of the rising incidence of antimicrobial resistance, host-modulating strategies for treating infections are of increasing interest and relevance. Such host-modulating strategies seek to control or alter the host immune response in order to more effectively combat infections. A primary concern of such strategies is balancing anti-pathogen effects with unwanted inflammation-induced tissue damage.

SUMMARY

As described herein, the inventors have discovered that inhibition of inositol hexakisphosphate kinase 1 (IP6K1) provides the surprising effect of increasing host bacterial killing while reducing harmful neutrophil accumulation in the lung. This is particularly surprising as inhibition of IP6K1 in neutrophils themselves was previously known to increase their inflammatory activity and accumulation. However, as the inventors demonstrate herein, neutrophil accumulation in the lung is uniquely regulated by platelets. Inhibition of IP6K1 in platelets alters the platelet activity in such a way as to reduce neutrophil accumulation specifically in the lung. As a result, IP6K1 inhibition is a particularly suitable treatment for lung infections and it is demonstrated herein that it successfully treats both gram-positive and gram-negative bacterial pneumonia.

In one aspect of any of the embodiments, described herein is a method of reducing neutrophil recruitment to the lung, the method comprising administering to the subject an inhibitor of inositol hexakisphosphate kinase 1 (IP6K1). In one aspect of any of the embodiments, described herein is a method of treating or preventing a lung infection or lung inflammatory condition in a subject in need thereof, the method comprising administering to the subject an inhibitor of inositol hexakisphosphate kinase 1 (IP6K1).

In one aspect of any of the embodiments, described herein is a composition comprising an inhibitor of inositol hexakisphosphate kinase 1 (IP6K1) for use in reducing neutrophil recruitment to the lung in a subject in need thereof. In one aspect of any of the embodiments, described herein is a composition comprising an inhibitor of inositol hexakisphosphate kinase 1 (IP6K1) for use in treating or preventing a lung infection or lung inflammatory condition in a subject in need thereof.

In one embodiment of any of the aspects, the infection is bacterial pneumonia. In one embodiment of any of the aspects, the subject is a subject with or determined to have pulmonary neutrophil accumulation. In one embodiment of any of the aspects, the subject is a subject with or determined to have increased inorganic polyphosphate (polyP) levels. In one embodiment of any of the aspects, the subject is a subject with or determined to have increased serum inorganic polyphosphate (polyP) levels.

In one embodiment of any of the aspects, the inhibitor is an inhibitory nucleic acid. In one embodiment of any of the aspects, the inhibitor is TNP [N2-(m-(trifluoromethyl)benzyl) N6-(p-nitrobenzyl)purine]. In one embodiment of any of the aspects, the inhibitor is administered in a composition which further comprises a platelet-targeting molecule.

BRIEF DESCRIPTION OF THE DRAWINGS

FIG. 1A: Bacterial killing in inflamed lungs. Live bacteria were quantified as cfu per lung. The experiment was repeated three times and the data were pooled and analyzed together. Data shown are means±SEM (n≥5 mice per group). FIG. 1B: The numbers of recruited neutrophils in bronchoalveolar lavage fluid (BALF). All data are presented as mean SEM (n≥5 mice per group). FIG. 1C: Representative hematoxylin and eosin (H&E) stained images of lung tissues show emigrated neutrophils and polymerized fibrin (arrows) in the pulmonary parenchyma. FIG. 1D: Recruited neutrophils in alveolar spaces were quantified as volume fraction of the alveolar spaces using standard point-counting morphometry. Data shown are means±SEM (n≥5 mice per group). FIG. 1E: Pulmonary edema formation was quantified as the percentage of edema area in the total parenchymal region. Data shown are means SEM (n≥5 mice per group). FIG. 1F: BALF total protein level. Data shown are means±SEM (n=5 mice per group). FIG. 1G: Lung wet weight-to-dry weight ratio was measured at 24 hr after E. coli instillation. Data shown are means±SEM (n=5 mice per group). FIG. 1H: Survival rates of E. coli-challenged WT and IP6K1-deficient mice. Mice were intratracheally challenged with $5\times10^6$ live E. coli. Survival rates were analyzed using the Kaplan-Meier survival curves and log-rank test. FIG. 1I: The numbers of recruited neutrophils in BALF were measured at 24 hr after E. coli instillation. In untreated and platelet-depleted groups, mice were intratracheally instilled with $2\times10^6$ cfu of E. coli. In the neutrophil-depleted group, mice were intratracheally instilled with $2\times10^5$ cfu. Data shown are means±SD (n=5 mice per group). FIG. 1J: Bacterial killing in inflamed lungs. Data shown are means±SD (n=5 mice per group). FIG. 1K: Lung wet weight-to-dry weight ratio. Values are means±SD (n=5 mice per group). FIG. 1L: Lung vascular permeability was evaluated by Evans blue (EB) dye. Data shown are means±SD (n=5 mice per group). *p<0.05 vs. WT mice. Statistical analysis was performed using student's t-test unless differently indicated.

FIGS. 2A-2L demonstrate that disrupting IP6K1 inhibits neutrophil accumulation and reduces lung damage in lipopolysaccharide (LPS)-induced lung inflammation. Mice were intratracheally instilled with 5 mg/kg LPS (*E. coli* O111:B4) and euthanized at the indicated time points. FIG. 2A: Total cells in BALF were stained with a modified Wright-Giemsa stain. FIG. 2B: The number of pulmonary neutrophils was counted using cytospin preparations. Data shown are means±SD (n=4 mice per group). FIG. 2C: BALF total protein levels. Data shown are means±SD (n=4 mice per group). FIG. 2D: Representative H&E staining of LPS-treated lung tissues. FIG. 2E: Quantification of recruited neutrophils in alveolar spaces. Data shown are means±SEM (n≥5 mice per group). FIG. 2F: Pulmonary edema formation quantified as the percentage of edema area in the total parenchymal region. Data shown are means±SEM (n=5 mice per group). FIG. 2G: Lung vascular permeability was evaluated by Evans blue dye. Data shown are means±SD (n=5 mice per group). FIG. 2H: Lung wet weight-to-dry weight ratio was measured at 24 hr after *E. coli* instillation. Data shown are means±SD (n=4 mice per group). FIG. 2I: Survival rates of LPS-challenged WT and IP6K1-deficient mice. Mice were intratracheally challenged with LPS (10 mg/kg body weight). Survival rates were analyzed using the Kaplan-Meier survival curves and log-rank test. FIG. 2J: Schematic of the neutrophil adoptive transfer assay. FIG. 2K: Purified WT and IP6K1-deficient neutrophil mixture for adoptive transfer (input) and adoptively transferred circulating neutrophils. FIG. 2L: Relative accumulation rates were quantified as ratios of adoptively transplanted IP6K1-null neutrophils to WT neutrophils in BALF. Data shown are means±SD (n=4 mice per group). *p<0.05 vs. WT mice. Statistical analysis was performed using student's t-test unless differently indicated.

FIGS. 3A-3J demonstrate that disruption of IP6K1 in platelets suppresses NPA formation both ex vivo and in vivo in LPS-induced lung inflammation. FIG. 3A: Platelet accumulation in the lungs after intratracheal LPS challenge (5 mg/kg body weight). Lung sections were stained with CD41 antibody. Hoechst was used as a nuclear counterstain. FIG. 3B: The platelet index in lung sections was expressed as the number of platelets (CD41+ cells) per field of view. At least five fields of view were randomly picked for each experiment and the averages were used for the calculation. Data shown are means±SEM (n=10 mice total, data are pooled from three experiments). FIG. 3C: Neutrophil-platelet aggregates (NPAs) in the inflamed lungs. The lung sections were co-stained with Ly6G and CD41 antibodies. The co-localization of neutrophils (Ly6G+) and platelets (CD41+) indicated NPA formation. The right panel is an inset of the left. FIG. 3D: NPA % was calculated as the percentage of Ly6G and CD41 double-positive cells (NPAs) among all Ly6G+ cells. Data shown are means±SEM (n=10 mice). FIG. 3E: FACS analysis of NPA formation in peripheral blood. Data shown are means±SEM (n=4 mice). *p<0.05 vs. WT mice. FIG. 3F: FACS analysis of ex vivo NPA formation. WT neutrophils and platelets were incubated with LPS (1 µg/mL) for 2 h at 37° C. After incubation, cell mixtures were stained with CD11b, CD41, and Ly6G. The NPAs were CD41 and Ly6G double-positive on FACS. FIG. 3G: NPA formation was calculated at the indicated LPS concentrations. Data shown are means±SEM of four experiments. FIG. 3H: NPA formation between WT or Ip6k1 KO neutrophils and platelets. WT (WN) or Ip6k1-KO (KN) neutrophils and WT (WP) or Ip6k1-KO (KP) platelets were incubated in the presence of LPS (5 µg/mL) or MIP2 (1 nM). Data shown are means±SEM of ≥4 experiments. FIG. 3I NPA formation between fluorescently labeled neutrophils and platelets. Neutrophils were stained with calcein AM (5 µg/ml) for 10 min. Platelets were isolated from whole blood and stained with calcein red AM (5 µg/ml) for 10 min. The labeled neutrophils and platelets were incubated with LPS (5 µg/mL) for 2 h at 37° C. Shown are representative images. FIG. 3J: The number of platelets in each NPA. The experiment was repeated three times and the data were pooled and analyzed together. Data shown are means±SEM (n=10 samples). *p<0.05 vs. WN+WP. Statistical analysis was performed using student's t-test.

FIGS. 4A-4K demonstrate that IP6K1-mediated polyP production by platelets plays a critical role in LPS-induced NPA formation. FIG. 4A: Polyphosphate (polyP) levels in WT and Ip6k1−/− platelets. *p<0.05 vs. WT platelets. FIG. 4B: LPS-induced polyP secretion in neutrophil-platelet co-cultures. WT (WN) or Ip6k1-KO (KN) neutrophils (5×10$^6$) and WT (WP) or Ip6k1-KO (KP) platelets (1×10$^9$) were incubated in the presence of LPS (5 µg/mL) for 2 h at 37° C. polyP levels in the supernatants were measured. Data shown are means±SEM of four experiments. FIG. 4C: NPA formation in the presence of polyP analyzed as described in FIG. 3F. Data shown are means±SEM of five experiments. *p<0.05 vs. cells treated with PBS. FIG. 4D: Subcellular localization of polyP in unstimulated platelets. PolyP was stained with DAPI. DAPI-polyP fluoresces yellow when viewed under UV. FIG. 4E: FACS analysis of NPA formation in peripheral blood. Shown are percentage of neutrophils (Ly6G+) forming NPAs in whole blood. Data shown are means±SEM (n=5 mice per group). *p<0.05 vs. WT mice. FIG. 4F: Neutrophil accumulation to the inflamed lungs in polyP-treated mice. Data shown are means±SEM (n=5 mice per group). FIG. 4G: BALF total protein levels. Data shown are means±SEM (n≥5 mice per group). FIG. 4H: Hematoxylin and eosin (H&E) staining of lung tissues. The right panels are insets of left panels. FIG. 4I: Recruited neutrophils in alveolar spaces were quantified as volume fraction of the alveolar spaces using standard point-counting morphometry. Data shown are means±SEM (n n≥5 mice per group). FIG. 4J: Pulmonary edema formation was quantified as the percentage of edema area in the total parenchymal region. Data shown are means±SEM (n n≥5 mice per group). *p<0.05 vs. WT mice. FIG. 4K: Lung wet weight-to-dry weight ratio was measured at 24 hr after LPS-instillation. Data shown are means±SEM (n=4 mice per group). *p<0.05 vs. WT mice. Statistical analysis was performed using student's t-test.

FIGS. 5A-5H demonstrate that polyP regulates NPA formation through the bradykinin pathway. FIG. 5A: Schematic of polyP activation in the bradykinin pathway. HMWK (or HK), high molecular weight kininogen. BK, bradykinin. HKa, cleaved HMWK. FIG. 5B: NPA formation in the presences or absence of bradykinin (20 µM). Neutrophils were pretreated with BK for 5 min and then incubated with WT or IP6K1-deficient platelets. Data shown are means±SD of three experiments. *p<0.05 vs. cells treated with PBS. FIG. 5C: NPA formation in the presence or absence of HKa (1 µg/ml). Data shown are means±SEM of ≥3 experiments. FIG. 5D: NPA formation in the presence or absence of both BK and HKa. Data shown are means±SEM of three experiments. FIG. 5E: NPA formation in the presence or absence of HKa and Lys-BK (1 µM), a B1 receptor agonist. Data shown are means±SEM of four experiments. FIG. 5F: NPA formation in the presence or absence of a BK1 receptor inhibitor. Neutrophils were pretreated with BK2 receptor inhibitor R715 (8 µM) for 5 min. Data shown are means±SEM of four experiments. FIG. 5G: NPA formation in the presence or absence BK2 receptor inhibitor. Neutrophils were pretreated with BK2 receptor inhibitor HOE140 (150 nM) for 5 min. Data shown are means±SEM of four experiments. FIG. 5H: Surface expression of adhesion molecule CD11b on neutrophils. WT neutrophils and platelets were treated with polyP for 2 h and CD11b surface levels were detected by FACS. *p<0.05 vs. cells treated with LPS alone (n=10 mice per group). Statistical analysis was performed using student's t-test.

FIG. 6A: PolyP levels in platelets. Mice were treated with TNP or DMSO alone for 10 days (20 mg/kg body weight, once a day). The experiment was repeated three times and the data were pooled and analyzed together. Data shown are means±SEM (n=7 mice per group). FIG. 6B: LPS-induced polyP secretion in neutrophil-platelet co-cultures. Neutrophils ($5\times10^6$) isolated from DMSO (N-DMSO) or TNP (N-TNP)-treated mice and platelets ($1\times10^9$) isolated from DMSO (P-DMSO) or TNP (P-TNP)-treated mice were incubated in the presence of LPS (5 μg/mL) for 2 h at 37° C. Data shown are means±SEM of four experiments. FIG. 6C: LPS-induced NPA formation. Neutrophils and platelets were isolated from DMSO (untreated) and TNP-treated mice and incubated with LPS (1 μg/mL) for 2 h at 37° C. Data shown are means±SEM of five experiments. FIG. 6D: Percentage of NPAs in whole blood. DMSO and TNP-treated mice were intratracheally instilled with 5 mg/kg LPS. NPA formation was analyzed at 24 hr after the LPS instillation. Data shown are means±SEM (n=4 mice per group). FIG. 6E: Bacterial killing in inflamed lungs. Data shown are means±SEM (n≥5 mice per group). FIG. 6F: Neutrophil accumulation in the inflamed lungs. Data shown are means±SEM (n≥5 mice per group). FIG. 6G: Representative H&E staining of lung tissues. FIG. 6H: Recruited neutrophils in alveolar spaces were quantified as volume fraction of the alveolar space using standard point-counting morphometry. Data shown are means±SEM (n=9 mice per group). FIG. 6I: Pulmonary edema formation was quantified as the percentage of edema area in the total parenchymal region using. Data shown are means±SEM (n=9 mice per group). FIG. 6J: Lung vascular permeability was evaluated by BALF total protein level. Data shown are means±SEM (n≥5 mice per group). FIG. 6K: Lung wet weight-to-dry weight ratio was measured at 24 hr after *E. coli* instillation. Data shown are means±SD (n=4 mice per group). FIG. 6L: PolyP levels in human platelets. Human platelets were treated with TNP (20 μM) at room temperature for 4 days. Data shown are means±SEM (n=8 donors per group). FIG. 6M: NPA formation between human neutrophils and platelets. NPA % was calculated as the percentage of CD66+, CD16+ and CD41 triple-positive cells (NPAs) among all CD66+ and CD16+ cells. Data shown are means±SEM of five experiments. *p<0.05. Statistical analysis was performed using student's t-test.

FIG. 7A: The number of alveolar macrophages in BALF of unchallenged mice. Data shown are means±SEM (n=4 mice per group). FIGS. 7B-7D: Mice were challenged by intratracheal instillation of LPS (5 mg/kg body weight) and sacrificed 24 h later. FIG. 7B: Whole lungs were homogenized. The levels of indicated surfactant proteins/antimicrobial peptides were assessed by western blotting with surfactant protein A (Abcam), surfactant protein B (Abbiotec), CRAMP (cathelin-related antimicrobial peptide) (Santa Cruz), or beta-defensin 2 (Abbiotec) antibodies. FIG. 7C: The viability of accumulated neutrophils was determined by the TUNEL assay. FIG. 7D: Neutrophil apoptosis was expressed as the number of apoptotic cells per field of view. At least 10 fields of view were randomly picked for each experiment and the averages were used for the calculation. Data shown are means±SEM (n≥9 mice per group). p<0.05 was defined as significant.

FIG. 9A: Platelet depletion in WT and IP6K1-deficient mice. Mice were intravenously injected with a single dose of platelet depletion (anti-GPIb/CD42b) antibody. The peripheral blood platelet counts were assessed at indicated time points. Data shown are means±SD (n=3 mice per group). FIG. 9B: Peripheral blood platelet count in untreated, neutrophil-depleted, and platelet-depleted mice. Data shown are means±SD (n=5 mice per group). FIG. 9C: Peripheral blood neutrophil count in untreated, neutrophil-depleted, and platelet-depleted mice. Data shown are means±SD (n=5 mice per group). FIG. 9D: BALF total protein level. The experiment was conducted as described in FIG. 1I-1L. Data shown are means±SD (n=5 mice per group). FIG. 9E: Survival rates of *E. coli*-challenged WT and IP6K1-deficient mice. Age- and sex-matched (10-week old male) wild-type and IP6K1-deficient mice were intratracheally challenged with $5\times10^6$ (for untreated and platelet-depleted mice) or $5\times10^5$ (for neutrophil-depleted mice) live *E. coli* and monitored for 5 days. Survival rates were analyzed using the Kaplan-Meier survival curves and log-rank test. *p<0.05 vs WT.

FIG. 10A: Bacterial killing in inflamed lungs. Live bacteria were quantified as cfu per lung. Data shown are means±SEM (n=4 mice). FIG. 10B: The numbers of recruited neutrophils in bronchoalveolar lavage fluid (BALF). All data are presented as mean±SEM (n=4 mice). FIG. 10C: BALF total protein level. Protein accumulation in the inflamed lung was measured using a Bio-Rad protein assay kit. Data shown are means±SEM (n=4 mice). FIG. 10D: Lung wet weight-to-dry weight ratio was measured at 24 hr after *S. aureus* instillation. Values are means±SEM; n=5 mice/group. FIG. 10E: Survival rates of *S. aureus*-challenged WT and IP6K1-deficient mice. Age- and sex-matched (10-week old male) wild-type and IP6K1-deficient mice were intratracheally challenged with $1\times10^9$ live *S. aureus* and monitored for 7 days. Survival rates were analyzed using the Kaplan-Meier survival curves and log-rank test. *p<0.05 vs WT.

FIG. 13A: Neutrophil-platelet aggregates can be induced by LPS O157:H7. Neutrophils and platelets were isolated from WT mice and incubated with LPS O157:H7 (1 mg/ml or 5 mg/ml) for 2 h at 37° C. to induce NPAs ex vivo. After incubation, cell mixtures were stained with CD11b, CD41, and Ly6G and analyzed by flow cytometry to detect NPAs. NPA formation was calculated at the indicated LPS concentrations. Data shown are means±SEM of four experiments. FIG. 13B: NPA formation between WT or Ip6k1−/− neutrophils and platelets. The experiment was conducted using LPS O157:H7 as described in FIG. 3G. Data shown are means±SEM of four experiments. *$p<0.05$ vs. cells treated with PBS.

FIG. 15A: NPA formation in the presence or absence of polyP. FACS analysis of NPA formation in peripheral blood was conducted as described in FIG. 4E. Both untreated and platelet-depleted mice were used in this experiment. Shown are percentage of NPAs in whole blood. Data shown are means±SD (n=5 mice per group). FIG. 15B: Neutrophil accumulation to the inflamed lungs in untreated or polyP-treated normal mice or platelet-depleted mice. The numbers of neutrophils in BALF were determined as described in FIG. 4F. Data shown are means±SD (n=5 mice per group). *$p<0.05$.

FIG. 16A: WT neutrophils and platelets were treated with polyP for 2 h. CD11b surface levels were detected by FACS. FIGS. 16B-16C: Surface expression of adhesion molecules CD18 and Cd162 on neutrophils. WT neutrophils and platelets were treated with polyP for 2 h. CD18 and Cd162 surface levels were detected by FACS. Data shown are means±SEM of four experiments. *$p<0.05$ vs. cells treated with LPS alone.

DETAILED DESCRIPTION

Figure 1A:
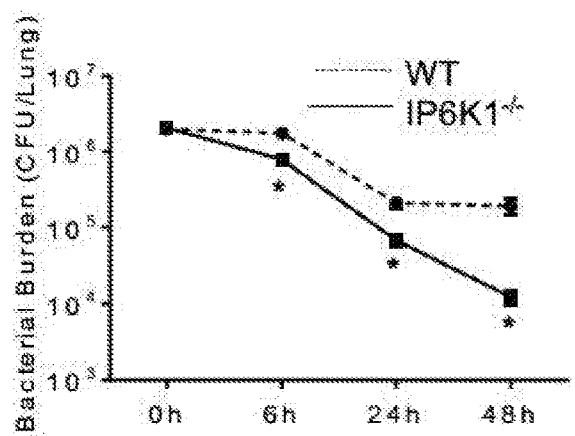
FIGS. 1A-1L demonstrate that disrupting IP6K1 enhances bacterial killing and reduces lung damage in bacterial pneumonia. Mice were intratracheally instilled with $2\times10^6$ cfu of E. coli and euthanized at indicated time points.

As described herein, the inventors have found that inhibition of inositol hexakisphosphate kinase 1 (IP6K1) acts uniquely upon neutrophil behavior in the lung, that is, it reduces neutrophil accumulation in the lung in contrast to previously observed effects in other areas of the body. Accordingly in one aspect of any of the embodiments, described herein is a method of reducing neutrophil recruitment to the lung, the method comprising administering to the subject an inhibitor of inositol hexakisphosphate kinase 1 (IP6K1).

As used herein, "inositol hexakisphosphate kinase 1" or "IP6K1" refers to an enzyme of the inositol phosphokinase (IPK) family which converts inositol hexakisphosphate (InsP6) to diphosphoinositol pentakisphosphate (InsP7/PP-InsP5). It may also convert 1,3,4,5,6-pentakisphosphate (InsP5) to PP-InsP4. Sequences of IP6K1 genes and expression products are known for a number of species, e.g., human IP6K1 (NCBI Gene ID 9807) mRNA (e.g., NCBI Ref Seqs. NM_001006115.2; NM_001242829.1; and NM_153273.4) and polypeptide (e.g., NCBI Ref Seqs. NP_001006115.1; NM_001229758.1; and NP_695005.1) sequences.

As used herein, the term "inhibitor" refers to an agent which can decrease the expression and/or activity of the targeted expression product (e.g. mRNA encoding the target, or a target polypeptide), e.g. by at least 10% or more, e.g. by 10% or more, 50% or more, 70% or more, 80% or more, 90% or more, 95% or more, or 98% or more. The efficacy of an inhibitor of, for example, IP6K1, e.g. its ability to decrease the level and/or activity of IP6K1 can be determined, e.g. by measuring the level of IP6K1 protein (or its mRNA). Methods for measuring the level of a given mRNA and/or polypeptide are known to one of skill in the art, e.g. RT-PCR with primers can be used to determine the level of RNA, and Western blotting with an antibody can be used to determine the level of a polypeptide. In some embodiments of any of the aspects, an inhibitor can be an inhibitory nucleic acid; an aptamer; an antibody reagent; an antibody; or a small molecule. Exemplary IP6K1 inhibitors include inhibitory nucleic acids and TNP [N2-(m-(trifluoromethyl)benzyl) N6-(p-nitrobenzyl)purine].

In some embodiments of any of the aspects, the agent that inhibits IP6K1 is an inhibitory nucleic acid. In some embodiments of any of the aspects, inhibitors of the expression of a given gene can be an inhibitory nucleic acid. As used herein, "inhibitory nucleic acid" refers to a nucleic acid molecule which can inhibit the expression of a target, e.g., double-stranded RNAs (dsRNAs), inhibitory RNAs (iR-NAs), amiRNA, lncRNA, and the like. In some embodiments of any of the aspects, the inhibitory nucleic acid can hybridize, e.g, hybridize specifically under cellular conditions (e.g., in a platelet) to an IP6K1 transcript.

Double-stranded RNA molecules (dsRNA) have been shown to block gene expression in a highly conserved regulatory mechanism known as RNA interference (RNAi). The inhibitory nucleic acids described herein can include an RNA strand (the antisense strand) having a region which is 30 nucleotides or less in length, i.e., 15-30 nucleotides in length, generally 19-24 nucleotides in length, which region is substantially complementary to at least part the targeted mRNA transcript. The use of these iRNAs enables the targeted degradation of mRNA transcripts, resulting in decreased expression and/or activity of the target.

As used herein, the term "iRNA" refers to an agent that contains RNA (or modified nucleic acids as described below herein) and which mediates the targeted cleavage of an RNA transcript via an RNA-induced silencing complex (RISC) pathway. In some embodiments of any of the aspects, an iRNA as described herein effects inhibition of the expression and/or activity of a target, e.g. IP6K1. In some embodiments of any of the aspects, contacting a cell with the inhibitor (e.g. an iRNA) results in a decrease in the target mRNA level in a cell by at least about 5%, about 10%, about 20%, about 30%, about 40%, about 50%, about 60%, about 70%, about 80%, about 90%, about 95%, about 99%, up to and including 100% of the target mRNA level found in the cell without the presence of the iRNA. In some embodiments of any of the aspects, administering an inhibitor (e.g. an iRNA) to a subject results in a decrease in the target mRNA level in the subject by at least about 5%, about 10%, about 20%, about 30%, about 40%, about 50%, about 60%, about 70%, about 80%, about 90%, about 95%, about 99%, up to and including 100% of the target mRNA level found in the subject without the presence of the iRNA.

In some embodiments of any of the aspects, the iRNA can be a dsRNA. A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of the target, e.g., it can span one or more intron boundaries. The other strand (the sense strand) includes a region that is complementary to the antisense strand, such that the two strands hybridize and form a duplex structure when combined under suitable conditions. Generally, the duplex structure is between 15 and 30 base pairs in length inclusive, more generally between 18 and 25 base pairs in length inclusive, yet more generally between 19 and 24 base pairs in length inclusive, and most generally between 19 and 21 base pairs in length, inclusive. Similarly, the region of complementarity to the target sequence is between 15 and 30 base pairs in length inclusive, more generally between 18 and 25 base pairs in length inclusive, yet more generally between 19 and 24 base pairs in length inclusive, and most generally between 19 and 21 base pairs in length nucleotides in length, inclusive. In some embodiments of any of the aspects, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e., cleavage through a RISC pathway). dsRNAs having duplexes as short as 9 base pairs can, under some circumstances, mediate RNAi-directed RNA cleavage. Most often a target will be at least 15 nucleotides in length, preferably 15-30 nucleotides in length.

Exemplary embodiments of types of inhibitory nucleic acids can include, e.g., siRNA, shRNA, miRNA, and/or amiRNA, which are well known in the art.

In some embodiments of any of the aspects, the RNA of an iRNA, e.g., a dsRNA, is chemically modified to enhance stability or other beneficial characteristics. The nucleic acids described herein may be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of RNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments of any of the aspects, the modified RNA will have a phosphorus atom in its internucleoside backbone.

Modified RNA backbones can include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included. Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; others having mixed N, O, S and CH2 component parts, and oligonucleosides with heteroatom backbones, and in particular —CH2-NH—CH2-, —CH2-N(CH3)-O—CH2-[known as a methylene (methylimino) or MMI backbone], —CH2-O—N(CH3)-CH2-, —CH2-N(CH3)-N(CH3)-CH2- and —N(CH3)-CH2-CH2- [wherein the native phosphodiester backbone is represented as —O—P—O—CH2-].

In other RNA mimetics suitable or contemplated for use in iRNAs, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) Nucleic Acids Research 33(1):439-447; Mook, O R. et al., (2007) Mol Canc Ther 6(3):833-843; Grunweller, A. et al., (2003) Nucleic Acids Research 31(12): 3185-3193).

Modified RNAs can also contain one or more substituted sugar moieties. The iRNAs, e.g., dsRNAs, described herein can include one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Exemplary suitable modifications include O[(CH2)nO]mCH3, O(CH2).nOCH3, O(CH2) nNH2, O(CH2)nCH3, O(CH2)nONH2, and O(CH2)nON [(CH2)nCH3)]$_2$, where n and m are from 1 to about 10. In some embodiments of any of the aspects, dsRNAs include one of the following at the 2' position: C1 to C10 lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments of any of the aspects, the modification includes a 2' methoxyethoxy (2'-O—CH2CH2OCH3, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O(CH2)2ON(CH3)2 group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH2-O—CH2-N(CH2)2, also described in examples herein below.

Other modifications include 2'-methoxy (2'-OCH3), 2'-aminopropoxy (2'-OCH2CH2CH2NH2) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs may also have sugar mimetics such as cyclobutyl moieties in place of the pentofuranosyl sugar.

An inhibitory nucleic acid can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Certain of these nucleobases are particularly useful for increasing the binding affinity of the inhibitory nucleic acids featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

The preparation of the modified nucleic acids, backbones, and nucleobases described above are well known in the art.

Another modification of an inhibitory nucleic acid featured in the invention involves chemically linking to the inhibitory nucleic acid to one or more ligands, moieties or conjugates that enhance the activity, cellular distribution, pharmacokinetic properties, or cellular uptake of the iRNA. Such moieties include but are not limited to lipid moieties such as a cholesterol moiety (Letsinger et al., Proc. Natl. Acad. Sci. USA, 1989, 86: 6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylaminocarbonyloxycholesterol moiety (Crooke et al., J. Pharmacol. Exp. Ther., 1996, 277:923-937).

In some embodiments of any of the aspects, inhibitors can be direct IP6K1 inhibitors, i.e., they physically interact with an IP6K1 polypeptide, transcript, or gene.

In some embodiments of any of the aspects, two or more IPK6K1 inhibitors can be administered.

As used herein, "infection" refers to an abnormal and/or undesired presence of an organism in or on a subject. The presence can be abnormal in that the organism is a noncommensal species, e.g. one not typically found in or on a healthy subject, or it can be abnormal in that the organism is present at abnormally high levels, e.g. at least twice the level found in or on a healthy subject (e.g. twice the level, three times the level, four times the level, five times the level, or greater), or it can be abnormal in that the presence of the organism is causing or contributing to disease or symptoms thereof, e.g. congestion, necrosis, toxicity, etc. An infection can involve one or more different pathogenic species, e.g., one pathogenic species, two pathogenic species, or more species can be present in or on the subject.

In some embodiments of any of the aspects, a lung infection can be pneumonia, e.g., bacterial pneumonia. As used herein, the term "pneumonia" refers to an infection of the lungs that can be caused by a variety of microorganisms, including viruses, bacteria, fungi, and parasites. This triggers an immune response by sending white blood cells, including but not limited to neutrophils, to the lungs to attack the microorganisms. Neutrophils engulf and kill the offending organisms but also release cytokines, which result in a general activation of the immune system, which results in the fever, chills, and fatigue common in bacterial and fungal pneumonia. The white blood cells, microorganisms, and fluid leaked from surrounding pulmonary tissues and blood vessels fill the alveoli resulting in impaired oxygen transportation.

Bacterial pneumonia typically occurs when bacteria enter the lung through inhalation, though they may also reach the lung through the bloodstream if other parts of the body are infected. Bacteria commonly colonize the upper respiratory tract and are continually inhaled into the alveoli. Once inside the alveoli, bacteria travel into the spaces between the cells and also between adjacent alveoli through connecting pores. *Streptococcus pneumoniae* (*S. pneumoniae*) is a Gram-positive bacterium that often resides in the upper respiratory tract of healthy individuals and is the most common bacterial cause of pneumonia (i.e. pneumococcal pneumonia) in all age groups except newborn infants. *Staphylococcus aureus* is another Gram-positive bacterium that causes pneumonia. Staphylococcal pneumonias tend to develop in infants, the elderly or those who are debilitated by other illnesses. Gram-negative bacteria such as *Haemophilus influenzae, Klebsiella pneumoniae, Escherichia coli, Pseudomonas aeruginosa* and *Moraxella catarrhalis* are also possible causes of bacterial pneumonia. These bacteria often reside in the gut and enter the lungs when contents of the gut (such as vomit or feces) are inhaled. Gram-negative bacterial pneumonia most commonly infects infants, the elderly, people with chronic diseases and alcoholics. "Atypical" pneumonias are caused by organisms other than the typical bacteria, viruses or fungi. Bacteria such as *Coxiella burnetii, Chlamydophila pneumoniae, Mycoplasma pneumoniae*, and *Legionella pneumophila* are considered "atypical" because they cause uncharacteristic symptoms and do not respond to common antibiotics. The "atypical" forms of community-acquired pneumonia are becoming more common in North America.

As used herein, "inflammation" refers to the complex biological response to harmful stimuli, such as pathogens, damaged cells, or irritants. Inflammation is a protective attempt by the organism to remove the injurious stimuli as well as initiate the healing process for the tissue. Accordingly, the term "inflammation" includes any cellular process that leads to the production of pro-inflammatory cytokines, inflammation mediators and/or the related downstream cellular events resulting from the actions of the cytokines thus produced, for example, fever, fluid accumulation, swelling, abscess formation, and cell death. Inflammation can include both acute responses (i.e., responses in which the inflammatory processes are active) and chronic responses (i.e., responses marked by slow progression and formation of new connective tissue). Acute and chronic inflammation may be distinguished by the cell types involved. Acute inflammation often involves polymorphonuclear neutrophils; whereas chronic inflammation is normally characterized by a lymphohistiocytic and/or granulomatous response.

An inflammatory condition is any disease state characterized by inflammatory tissues (for example, infiltrates of leukocytes such as lymphocytes, neutrophils, macrophages, eosinophils, mast cells, basophils and dendritic cells) or inflammatory processes which provoke or contribute to the abnormal clinical and histological characteristics of the disease state. By way of non-limiting example, inflammatory conditions can be inflammatory conditions of the lung, such as asthma, bronchitis, chronic bronchitis, bronchiolitis, pneumonia, sinusitis, emphysema, adult respiratory distress syndrome, pulmonary inflammation, pulmonary fibrosis, and cystic fibrosis (which may additionally or alternatively involve the gastro-intestinal tract or other tissue(s)). In some embodiments of any of the aspects, an inflammatory condition is associated with an infection, e.g., viral, bacterial, fungal, parasite or prion infections. In some embodiments of any of the aspects, an inflammatory condition is associated with an allergic response. In some embodiments of any of the aspects, an inflammatory condition is associated with a pollutant (e.g., asbestosis, silicosis, or berylliosis).

In some embodiments of any of the aspects, the inflammatory condition can be a local condition, e.g., a rash or allergic reaction. In some embodiments of any of the aspects, the inflammation is associated with a wound.

In some embodiments of any of the aspects, the subject is a subject with or determined to have pulmonary neutrophil accumulation. For example, a higher level of neutrophils in the lungs than in a normal healthy subject or a higher level of neutrophils in the lungs than at an earlier time point for the same subject. Methods for detecting or measuring neutrophil accumulation are described elsewhere herein.

In some embodiments of any of the aspects, the subject is a subject with or determined to have increased inorganic polyphosphate (polyP) levels. For example, an increased inorganic polyphosphate (polyP) levels than in a normal healthy subject or increased inorganic polyphosphate (polyP) levels than at an earlier time point for the same subject. Methods for detecting or measuring polyP levels are described elsewhere herein. In some embodiments of any of the aspects, the polyP level is the serum polyP level.

As described herein, levels of neutrophil accumulation and/or polyP can be increased in subjects with a lung infection or lung inflammation, e.g., those that will benefit from the treatment described herein. In some embodiments of any of the aspects, the level of neutrophil accumulation and/or polyP can be increased in subjects with lung infection and/or lung inflammation. Accordingly, in one aspect of any of the embodiments, described herein is a method of treating lung infection and/or lung inflammation in a subject in need thereof, the method comprising administering an inhibitor of IP6K1 to a subject determined to have a level of neutrophil accumulation and/or polyP that is increase relative to a reference. In one aspect of any of the embodiments, described herein is a method of treating lung infection and/or lung inflammation in a subject in need thereof, the method comprising: a) determining the level of neutrophil accumulation and/or polyP in a sample obtained from a subject; and b) administering an inhibitor of IP6K1 to the subject if the level of neutrophil accumulation and/or polyP is increased relative to a reference.

In some embodiments of any of the aspects, when the subject is determined not to have an increased level of neutrophil accumulation and/or polyp, the subject can be administered an anti-microbial or anti-inflammatory treatment, e.g, not administered an inhibitor of IP6K1 or a host-modulating treatment. In some embodiments of any of the aspects, when the subject is determined not to have an increased level of neutrophil accumulation and/or polyp, the subject can be administered a course of treatment which does not comprise an inhibitor of IP6K1 and/or a host-modulating treatment. In some embodiments of any of the aspects, the anti-microbial can be an antibiotic.

In some embodiments of any of the aspects, the method comprises administering an inhibitor of IP6K1 to a subject previously determined to have a level of neutrophil accumulation and/or polyP that is increased relative to a reference. In some embodiments of any of the aspects, described herein is a method of treating lung infection and/or lung inflammation in a subject in need thereof, the method comprising: a) first determining the level of neutrophil accumulation and/or polyP in a sample obtained from a subject; and b) then administering an inhibitor of IP6K1 to the subject if the level of neutrophil accumulation and/or polyP is increased relative to a reference.

In one aspect of any of the embodiments, described herein is a method of treating lung infection and/or lung inflammation in a subject in need thereof, the method comprising: a) determining if the subject has a increased level of neutrophil accumulation and/or polyp, and b) administering an inhibitor of IP6K1 to the subject if the level of neutrophil accumulation and/or polyP is increased relative to a reference. In some embodiments of any of the aspects, the step of determining if the subject has an increased level of neutrophil accumulation and/or polyP can comprise i) obtaining or having obtained a sample from the subject and ii) performing or having performed an assay on the sample obtained from the subject to determine/measure the level of neutrophil accumulation and/or polyP in the subject. In some embodiments of any of the aspects, the step of determining if the subject has an increased level of neutrophil accumulation and/or polyP can comprise performing or having performed an assay on a sample obtained from the subject to determine/measure the level of neutrophil accumulation and/or polyP in the subject. In some embodiments of any of the aspects, the step of determining if the subject has an increased level of neutrophil accumulation and/or polyP can comprise ordering or requesting an assay on a sample obtained from the subject to determine/measure the level of neutrophil accumulation and/or polyP in the subject. In some embodiments of any of the aspects, the step of determining if the subject has an increased level of neutrophil accumulation and/or polyP can comprise receiving the results of an assay on a sample obtained from the subject to determine/measure the level of neutrophil accumulation and/or polyP in the subject. In some embodiments of any of the aspects, the step of determining if the subject has an increased level of neutrophil accumulation and/or polyP can comprise receiving a report, results, or other means of identifying the subject as a subject with an increased level of neutrophil accumulation and/or polyP.

In one aspect of any of the embodiments, described herein is a method of treating lung infection and/or lung inflammation in a subject in need thereof, the method comprising: a) determining if the subject has an increased level of neutrophil accumulation and/or polyP; and b) instructing or directing that the subject be administered an inhibitor of IP6K1 if the level of neutrophil accumulation and/or polyP is increased relative to a reference. In some embodiments of any of the aspects, the step of determining if the subject has an increased level of neutrophil accumulation and/or polyP can comprise i) obtaining or having obtained a sample from the subject and ii) performing or having performed an assay on the sample obtained from the subject to determine/measure the level of neutrophil accumulation and/or polyP in the subject. In some embodiments of any of the aspects, the step of determining if the subject has an increased level of neutrophil accumulation and/or polyP can comprise performing or having performed an assay on a sample obtained from the subject to determine/measure the level of neutrophil accumulation and/or polyP in the subject. In some embodiments of any of the aspects, the step of determining if the subject has an increased level of neutrophil accumulation and/or polyP can comprise ordering or requesting an assay on a sample obtained from the subject to determine/measure the level of neutrophil accumulation and/or polyP in the subject. In some embodiments of any of the aspects, the step of instructing or directing that the subject be administered a particular treatment can comprise providing a report of the assay results. In some embodiments of any of the aspects, the step of instructing or directing that the subject be administered a particular treatment can comprise providing a report of the assay results and/or treatment recommendations in view of the assay results.

In some embodiments of any of the aspects, measurement of the level of a target/marker and/or detection of the level or presence of a target/marker can comprise a transformation. As used herein, the term "transforming" or "transformation" refers to changing an object or a substance, e.g., biological sample, nucleic acid or protein, into another substance. The transformation can be physical, biological or chemical. Exemplary physical transformation includes, but is not limited to, pre-treatment of a biological sample, e.g., from whole blood to blood serum by differential centrifugation. A biological/chemical transformation can involve the action of at least one enzyme and/or a chemical reagent in a reaction. For example, a DNA sample can be digested into fragments by one or more restriction enzymes, or an exogenous molecule can be attached to a fragmented DNA sample with a ligase. In some embodiments of any of the aspects, a DNA sample can undergo enzymatic replication, e.g., by polymerase chain reaction (PCR).

Transformation, measurement, and/or detection of a target molecule, can comprise contacting a sample obtained from a subject with a reagent (e.g. a detection reagent) which is specific for the target, e.g., a target-specific reagent. In some embodiments of any of the aspects, the target-specific reagent is detectably labeled. In some embodiments of any of the aspects, the target-specific reagent is capable of generating a detectable signal. In some embodiments of any of the aspects, the target-specific reagent generates a detectable signal when the target molecule is present.

Methods to measure gene expression products are known to a skilled artisan. Such methods to measure gene expression products, e.g., protein level, include ELISA (enzyme linked immunosorbent assay), western blot, immunoprecipitation, and immunofluorescence using detection reagents such as an antibody or protein binding agents. Alternatively, a peptide can be detected in a subject by introducing into a subject a labeled anti-peptide antibody and other types of detection agent. For example, the antibody can be labeled with a detectable marker whose presence and location in the subject is detected by standard imaging techniques.

In some embodiments of any of the aspects, immunohistochemistry ("IHC") and immunocytochemistry ("ICC") techniques can be used. IHC is the application of immunochemistry to tissue sections, whereas ICC is the application of immunochemistry to cells or tissue imprints after they have undergone specific cytological preparations such as, for example, liquid-based preparations. Immunochemistry is a family of techniques based on the use of an antibody, wherein the antibodies are used to specifically target molecules inside or on the surface of cells. The antibody typically contains a marker that will undergo a biochemical reaction, and thereby experience a change of color, upon encountering the targeted molecules. In some instances, signal amplification can be integrated into the particular protocol, wherein a secondary antibody, that includes the marker stain or marker signal, follows the application of a primary specific antibody.

In some embodiments of any of the aspects, the assay can be a Western blot analysis. Alternatively, proteins can be separated by two-dimensional gel electrophoresis systems. Two-dimensional gel electrophoresis is well known in the art and typically involves iso-electric focusing along a first dimension followed by SDS-PAGE electrophoresis along a second dimension. These methods also require a considerable amount of cellular material. The analysis of 2D SDS-PAGE gels can be performed by determining the intensity of protein spots on the gel, or can be performed using immune detection. In other embodiments, protein samples are analyzed by mass spectroscopy.

Immunological tests can be used with the methods and assays described herein and include, for example, competitive and non-competitive assay systems using techniques such as Western blots, radioimmunoassay (RIA), ELISA (enzyme linked immunosorbent assay), "sandwich" immunoassays, immunoprecipitation assays, immunodiffusion assays, agglutination assays, e.g. latex agglutination, complement-fixation assays, immunoradiometric assays, fluorescent immunoassays, e.g. FIA (fluorescence-linked immunoassay), chemiluminescence immunoassays (CLIA), electrochemiluminescence immunoassay (ECLIA, counting immunoassay (CIA), lateral flow tests or immunoassay (LFIA), magnetic immunoassay (MIA), and protein A immunoassays. Methods for performing such assays are known in the art, provided an appropriate antibody reagent is available. In some embodiments of any of the aspects, the immunoassay can be a quantitative or a semi-quantitative immunoassay.

An immunoassay is a biochemical test that measures the concentration of a substance in a biological sample, typically a fluid sample such as blood or serum, using the interaction of an antibody or antibodies to its antigen. The assay takes advantage of the highly specific binding of an antibody with its antigen. For the methods and assays described herein, specific binding of the target polypeptides with respective proteins or protein fragments, or an isolated peptide, or a fusion protein described herein occurs in the immunoassay to form a target protein/peptide complex. The complex is then detected by a variety of methods known in the art. An immunoassay also often involves the use of a detection antibody.

Enzyme-linked immunosorbent assay, also called ELISA, enzyme immunoassay or EIA, is a biochemical technique used mainly in immunology to detect the presence of an antibody or an antigen in a sample. The ELISA has been used as a diagnostic tool in medicine and plant pathology, as well as a quality control check in various industries.

In one embodiment, an ELISA involving at least one antibody with specificity for the particular desired antigen (e.g., any of the targets as described herein) can also be performed. A known amount of sample and/or antigen is immobilized on a solid support (usually a polystyrene micro titer plate). Immobilization can be either non-specific (e.g., by adsorption to the surface) or specific (e.g. where another antibody immobilized on the surface is used to capture antigen or a primary antibody). After the antigen is immobilized, the detection antibody is added, forming a complex with the antigen. The detection antibody can be covalently linked to an enzyme, or can itself be detected by a secondary antibody which is linked to an enzyme through bio-conjugation. Between each step the plate is typically washed with a mild detergent solution to remove any proteins or antibodies that are not specifically bound. After the final wash step the plate is developed by adding an enzymatic substrate to produce a visible signal, which indicates the quantity of antigen in the sample. Older ELISAs utilize chromogenic substrates, though newer assays employ fluorogenic substrates with much higher sensitivity.

In another embodiment, a competitive ELISA is used. Purified antibodies that are directed against a target polypeptide or fragment thereof are coated on the solid phase of multi-well plate, i.e., conjugated to a solid surface. A second batch of purified antibodies that are not conjugated on any solid support is also needed. These non-conjugated purified antibodies are labeled for detection purposes, for example, labeled with horseradish peroxidase to produce a detectable signal. A sample (e.g., a blood sample) from a subject is mixed with a known amount of desired antigen (e.g., a known volume or concentration of a sample comprising a target polypeptide) together with the horseradish peroxidase labeled antibodies and the mixture is then are added to coated wells to form competitive combination. After incubation, if the polypeptide level is high in the sample, a complex of labeled antibody reagent-antigen will form. This complex is free in solution and can be washed away. Washing the wells will remove the complex. Then the wells are incubated with TMB (3, 3', 5, 5'-tetramethylbenzidene) color development substrate for localization of horseradish peroxidase-conjugated antibodies in the wells. There will be no color change or little color change if the target polypeptide level is high in the sample. If there is little or no target polypeptide present in the sample, a different complex in formed, the complex of solid support bound antibody reagents-target polypeptide. This complex is immobilized on the plate and is not washed away in the wash step. Subsequent incubation with TMB will produce significant color change. Such a competitive ELSA test is specific, sensitive, reproducible and easy to operate.

There are other different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; and Oellerich, M. 1984, J. Clin. Chem. Clin. Biochem. 22:895-904. These references are hereby incorporated by reference in their entirety.

In one embodiment, the levels of a target in a sample can be detected by a lateral flow immunoassay test (LFIA), also known as the immunochromatographic assay, or strip test. LFIAs are a simple device intended to detect the presence (or absence) of antigen, e.g. a polypeptide, in a fluid sample. There are currently many LFIA tests used for medical diagnostics, either for home testing, point of care testing, or laboratory use. LFIA tests are a form of immunoassay in which the test sample flows along a solid substrate via capillary action. After the sample is applied to the test strip it encounters a colored reagent (generally comprising antibody specific for the test target antigen) bound to microparticles which mixes with the sample and transits the substrate encountering lines or zones which have been pretreated with another antibody or antigen. Depending upon the level of target polypeptides present in the sample the colored reagent can be captured and become bound at the test line or zone. LFIAs are essentially immunoassays adapted to operate along a single axis to suit the test strip format or a dipstick format. Strip tests are extremely versatile and can be easily modified by one skilled in the art for detecting an enormous range of antigens from fluid samples such as urine, blood, water, and/or homogenized tissue samples etc. Strip tests are also known as dip stick tests, the name bearing from the literal action of "dipping" the test strip into a fluid sample to be tested. LFIA strip tests are easy to use, require minimum training and can easily be included as components of point-of-care test (POCT) diagnostics to be use on site in the field. LFIA tests can be operated as either competitive or sandwich assays. Sandwich LFIAs are similar to sandwich ELISA. The sample first encounters colored particles which are labeled with antibodies raised to the target antigen. The test line will also contain antibodies to the same target, although it may bind to a different epitope on the antigen. The test line will show as a colored band in positive samples. In some embodiments of any of the aspects, the lateral flow immunoassay can be a double antibody sandwich assay, a competitive assay, a quantitative assay or variations thereof. Competitive LFIAs are similar to competitive ELISA. The sample first encounters colored particles which are labeled with the target antigen or an analogue. The test line contains antibodies to the target/its analogue. Unlabelled antigen in the sample will block the binding sites on the antibodies preventing uptake of the colored particles. The test line will show as a colored band in negative samples. There are a number of variations on lateral flow technology. It is also possible to apply multiple capture zones to create a multiplex test.

The use of "dip sticks" or LFIA test strips and other solid supports have been described in the art in the context of an immunoassay for a number of antigen biomarkers. U.S. Pat. Nos. 4,943,522; 6,485,982; 6,187,598; 5,770,460; 5,622,871; 6,565,808, U.S. patent application Ser. No. 10/278,676; U.S. Ser. No. 09/579,673 and U.S. Ser. No. 10/717,082, which are incorporated herein by reference in their entirety, are non-limiting examples of such lateral flow test devices. Examples of patents that describe the use of "dip stick" technology to detect soluble antigens via immunochemical assays include, but are not limited to U.S. Pat. Nos. 4,444,880; 4,305,924; and 4,135,884; which are incorporated by reference herein in their entireties. The apparatuses and methods of these three patents broadly describe a first component fixed to a solid surface on a "dip stick" which is exposed to a solution containing a soluble antigen that binds to the component fixed upon the "dip stick," prior to detection of the component-antigen complex upon the stick. It is within the skill of one in the art to modify the teachings of this "dip stick" technology for the detection of polypeptides using antibody reagents as described herein.

Other techniques can be used to detect the level of a target in a sample. One such technique is the dot blot, an adaptation of Western blotting (Towbin et at., Proc. Nat. Acad. Sci. 76:4350 (1979)). In a Western blot, the target or fragment thereof can be dissociated with detergents and heat, and separated on an SDS-PAGE gel before being transferred to a solid support, such as a nitrocellulose or PVDF membrane. The membrane is incubated with an antibody reagent specific for the target or a fragment thereof. The membrane is then washed to remove unbound proteins and proteins with non-specific binding. Detectably labeled enzyme-linked secondary or detection antibodies can then be used to detect and assess the amount of polypeptide in the sample tested. A dot blot immobilizes a sample on a defined region of a support, which is then probed with antibody and labelled secondary antibody as in Western blotting. The intensity of the signal from the detectable label in either format corresponds to the amount of enzyme present, and therefore the amount of target. Levels can be quantified, for example by densitometry.

In some embodiments of any of the aspects, the level of a target can be measured, by way of non-limiting example, by Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluoresence assay; mass spectroscopy and/or immunoelectrophoresis assay.

RNA and/or DNA molecules can be isolated, derived, or amplified from a biological sample, such as a blood sample. Techniques for the detection of mRNA expression is known by persons skilled in the art, and can include but not limited to, PCR procedures, RT-PCR, quantitative RT-PCR Northern blot analysis, differential gene expression, RNAse protection assay, microarray based analysis, next-generation sequencing; hybridization methods, etc.

In general, the PCR procedure describes a method of gene amplification which is comprised of (i) sequence-specific hybridization of primers to specific genes or sequences within a nucleic acid sample or library, (ii) subsequent amplification involving multiple rounds of annealing, elongation, and denaturation using a thermostable DNA polymerase, and (iii) screening the PCR products for a band of the correct size. The primers used are oligonucleotides of sufficient length and appropriate sequence to provide initiation of polymerization, i.e. each primer is specifically designed to be complementary to a strand of the genomic locus to be amplified. In an alternative embodiment, mRNA level of gene expression products described herein can be determined by reverse-transcription (RT) PCR and by quantitative RT-PCR (QRT-PCR) or real-time PCR methods. Methods of RT-PCR and QRT-PCR are well known in the art.

In some embodiments of any of the aspects, the level of an mRNA can be measured by a quantitative sequencing technology, e.g. a quantitative next-generation sequence technology. Methods of sequencing a nucleic acid sequence are well known in the art. Briefly, a sample obtained from a subject can be contacted with one or more primers which specifically hybridize to a single-strand nucleic acid sequence flanking the target gene sequence and a complementary strand is synthesized. In some next-generation technologies, an adaptor (double or single-stranded) is ligated to nucleic acid molecules in the sample and synthesis proceeds from the adaptor or adaptor compatible primers. In some third-generation technologies, the sequence can be determined, e.g. by determining the location and pattern of the hybridization of probes, or measuring one or more characteristics of a single molecule as it passes through a sensor (e.g. the modulation of an electrical field as a nucleic acid molecule passes through a nanopore). Exemplary methods of sequencing include, but are not limited to, Sanger sequencing, dideoxy chain termination, high-throughput sequencing, next generation sequencing, 454 sequencing, SOLiD sequencing, polony sequencing, Illumina sequencing, Ion Torrent sequencing, sequencing by hybridization, nanopore sequencing, Helioscope sequencing, single molecule real time sequencing, RNAP sequencing, and the like. Methods and protocols for performing these sequencing methods are known in the art, see, e.g. "Next Generation Genome Sequencing" Ed. Michal Janitz, Wiley-VCH; "High-Throughput Next Generation Sequencing" Eds. Kwon and Ricke, Humanna Press, 2011; and Sambrook et al., Molecular Cloning: A Laboratory Manual (4 ed.), Cold Spring Harbor Laboratory Press, Cold Spring Harbor, N.Y., USA (2012); which are incorporated by reference herein in their entireties.

Nucleic acid and ribonucleic acid (RNA) molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Roiff, A et al. PCR: Clinical Diagnostics and Research, Springer (1994)).

In some embodiments of any of the aspects, one or more of the reagents (e.g. an antibody reagent and/or nucleic acid probe) described herein can comprise a detectable label and/or comprise the ability to generate a detectable signal (e.g. by catalyzing reaction converting a compound to a detectable product). Detectable labels can comprise, for example, a light-absorbing dye, a fluorescent dye, or a radioactive label. Detectable labels, methods of detecting them, and methods of incorporating them into reagents (e.g. antibodies and nucleic acid probes) are well known in the art.

In some embodiments of any of the aspects, detectable labels can include labels that can be detected by spectroscopic, photochemical, biochemical, immunochemical, electromagnetic, radiochemical, or chemical means, such as fluorescence, chemifluoresence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). The detectable label can be linked by covalent or non-covalent means to the reagent. Alternatively, a detectable label can be linked such as by directly labeling a molecule that achieves binding to the reagent via a ligand-receptor binding pair arrangement or other such specific recognition molecules. Detectable labels can include, but are not limited to radioisotopes, bioluminescent compounds, chromophores, antibodies, chemiluminescent compounds, fluorescent compounds, metal chelates, and enzymes.

In other embodiments, the detection reagent is label with a fluorescent compound. When the fluorescently labeled reagent is exposed to light of the proper wavelength, its presence can then be detected due to fluorescence. In some embodiments of any of the aspects, a detectable label can be a fluorescent dye molecule, or fluorophore including, but not limited to fluorescein, phycoerythrin, phycocyanin, o-phthaldehyde, fluorescamine, Cy3™, Cy5™, allophycocyanine, Texas Red, peridenin chlorophyll, cyanine, tandem conjugates such as phycoerythrin-Cy5™, green fluorescent protein, rhodamine, fluorescein isothiocyanate (FITC) and Oregon Green™, rhodamine and derivatives (e.g., Texas red and tetrahodimine isothiocynate (TRITC)), biotin, phycoerythrin, AMCA, CyDyes™, 6-carboxyfhiorescein (commonly known by the abbreviations FAM and F), 6-carboxy-2',4',7',4,7-hexachlorofiuorescein (HEX), 6-carboxy-4',5'-dichloro-2',7'-dimethoxyfluorescein (JOE or J), N,N,N',N'-tetramethyl-6carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. In some embodiments of any of the aspects, a detectable label can be a radiolabel including, but not limited to $^{3}H$, $^{125}I$, $^{35}S$, $^{14}C$, $^{32}P$, and $^{33}P$. In some embodiments of any of the aspects, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use to detectably label an antibody reagent include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase. In some embodiments of any of the aspects, a detectable label is a chemiluminescent label, including, but not limited to lucigenin, luminol, luciferin, isoluminol, theromatic acridinium ester, imidazole, acridinium salt and oxalate ester. In some embodiments of any of the aspects, a detectable label can be a spectral colorimetric label including, but not limited to colloidal gold or colored glass or plastic (e.g., polystyrene, polypropylene, and latex) beads.

In some embodiments of any of the aspects, detection reagents can also be labeled with a detectable tag, such as c-Myc, HA, VSV-G, HSV, FLAG, V5, HIS, or biotin. Other detection systems can also be used, for example, a biotin-streptavidin system. In this system, the antibodies immunoreactive (i. e. specific for) with the biomarker of interest is biotinylated. Quantity of biotinylated antibody bound to the biomarker is determined using a streptavidin-peroxidase conjugate and a chromagenic substrate. Such streptavidin peroxidase detection kits are commercially available, e. g. from DAKO; Carpinteria, Calif. A reagent can also be detectably labeled using fluorescence emitting metals such as $^{152}Eu$, or others of the lanthanide series. These metals can be attached to the reagent using such metal chelating groups as diethylenetriaminepentaacetic acid (DTPA) or ethylene-diaminetetraacetic acid (EDTA).

A level which is less than a reference level can be a level which is less by at least about 10%, at least about 20%, at least about 50%, at least about 60%, at least about 80%, at least about 90%, or less relative to the reference level. In some embodiments of any of the aspects, a level which is less than a reference level can be a level which is statistically significantly less than the reference level.

A level which is more than a reference level can be a level which is greater by at least about 10%, at least about 20%, at least about 50%, at least about 60%, at least about 80%, at least about 90%, at least about 100%, at least about 200%, at least about 300%, at least about 500% or more than the reference level. In some embodiments of any of the aspects, a level which is more than a reference level can be a level which is statistically significantly greater than the reference level.

In some embodiments of any of the aspects, the reference can be a level of the target in a population of subjects who do not have or are not diagnosed as having, and/or do not exhibit signs or symptoms of lung infection and/or lung inflammation. In some embodiments of any of the aspects, the reference can also be a level of the target in a control sample, a pooled sample of control individuals or a numeric value or range of values based on the same. In some embodiments of any of the aspects, the reference can be the level of a target in a sample obtained from the same subject at an earlier point in time, e.g., the methods described herein can be used to determine if a subject's sensitivity or response to a given therapy is changing over time.

In some embodiments of any of the aspects, the level of expression products of no more than 200 genes is determined. In some embodiments of any of the aspects, the level of expression products of no more than 100 genes is determined. In some embodiments of any of the aspects, the level of expression products of no more than 20 genes is determined. In some embodiments of any of the aspects, the level of expression products of no more than 10 genes is determined.

In some embodiments of the foregoing aspects, the expression level of a given gene can be normalized relative to the expression level of one or more reference genes or reference proteins.

In some embodiments of any of the aspects, the reference level can be the level in a sample of similar cell type, sample type, sample processing, and/or obtained from a subject of similar age, sex and other demographic parameters as the sample/subject for which the level of neutrophil accumulation and/or polyP is to be determined. In some embodiments of any of the aspects, the test sample and control reference sample are of the same type, that is, obtained from the same biological source, and comprising the same composition, e.g. the same number and type of cells.

The term "sample" or "test sample" as used herein denotes a sample taken or isolated from a biological organism, e.g., a blood or plasma sample from a subject. In some embodiments of any of the aspects, the present invention encompasses several examples of a biological sample. In some embodiments of any of the aspects, the biological sample is cells, or tissue, or peripheral blood, or bodily fluid. Exemplary biological samples include, but are not limited to, a biopsy, a tumor sample, biofluid sample; blood; serum; plasma; urine; sperm; mucus; tissue biopsy; organ biopsy; synovial fluid; bile fluid; cerebrospinal fluid; mucosal secretion; effusion; sweat; saliva; and/or tissue sample etc. The term also includes a mixture of the above-mentioned samples. The term "test sample" also includes untreated or pretreated (or pre-processed) biological samples. In some embodiments of any of the aspects, a test sample can comprise cells from a subject. In some embodiments of any of the aspects, the test sample can be a lung sample, lung aspirate, sputum sample, airway sample, serum sample, or the like.

The test sample can be obtained by removing a sample from a subject, but can also be accomplished by using a previously isolated sample (e.g. isolated at a prior timepoint and isolated by the same or another person).

In some embodiments of any of the aspects, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments of any of the aspects, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments of any of the aspects, the test sample is a clarified test sample, for example, by centrifugation and collection of a supernatant comprising the clarified test sample. In some embodiments of any of the aspects, a test sample can be a pre-processed test sample, for example, supernatant or filtrate resulting from a treatment selected from the group consisting of centrifugation, filtration, thawing, purification, and any combinations thereof. In some embodiments of any of the aspects, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of an expression product as described herein.

In some embodiments of any of the aspects, the methods, assays, and systems described herein can further comprise a step of obtaining or having obtained a test sample from a subject. In some embodiments of any of the aspects, the subject can be a human subject. In some embodiments of any of the aspects, the subject can be a subject in need of treatment for (e.g. having or diagnosed as having) a lung infection or lung inflammation or a subject at risk of or at increased risk of developing a lung infection or lung inflammation as described elsewhere herein.

In some embodiments of any of the aspects, the sample obtained from a subject can be a lung, lung aspirate, or sputum sample. In some embodiments of any of the aspects, the sample obtained from a subject can be a biopsy sample. In some embodiments of any of the aspects, the sample obtained from a subject can be a blood or serum sample.

In some embodiments of any of the aspects, the inhibitor is administered or provided in a composition which further comprises a platelet-targeting molecule. Targeting can be achieved, e.g. by conjugating the inhibitor to a targeting group or including the inhibitor in a composition comprising a targeting group (e.g. a nanoparticule). Targeting groups can include, e.g., a platelet targeting agent, e.g., a lectin, glycoprotein, lipid or protein, e.g., an antibody, that binds to platelet, or a cell permeation agent. Non-limiting examples of platelet targeting groups can include antibodies to platelet cell surface markers (e.g., CD41 (GP IIb/IIIa), CD42a (GPIX), CD42b (GPIb), CD61 (avb3, vitronectin receptor), PAC-1 (activated IIb/IIIa), CD62P (P-selectin), CD31 (PE-CAM), and CD63) and the like.

In some embodiments of any of the aspects, the subject is further administered an antibmicrobial (e.g., antibiotic) or anti-inflammatory.

As used herein, "antibiotic" refers to an agent that reduces, inhibits, or prevents microbial growth. In some embodiments of any of the aspects, an antibiotic can be bacteriostatic. In some embodiments of any of the aspects, an antibiotic can be bacteriocidal. The term "antibiotic" includes semi-synthetic modifications of various natural compounds. Accordingly, the term "antibiotic" includes, but is not limited to, aminoglycosides (e.g., gentamicin, streptomycin, kanamycin), β-lactams (e.g., penicillins and cephalosporins), vancomycins, bacitracins, macrolides (e.g., erythromycins), lincosamides (e.g., clindomycin), chloramphenicols, tetracyclines, amphotericins, cefazolins, clindamycins, mupirocins, sulfonamides and trimethoprim, rifampicins, metronidazoles, quinolones, novobiocins, polymixins, gramicidins, or any salts or variants thereof.

In some embodiments of any of the aspects, the antibiotic is selected from the group consisting of: vancomycin; an inhibitor of cell wall synthesis; rifampin; an ansamycin (e.g., rifamycins, geldanamycin, ansamitocin, naphthomycins, and dertivatives thereof); a rifamycin (e.g., rifamide, various naturally-occurring rifamycins, rifampicin (or rifampin), rifabutin, rifapentine, rifalazil, rifaximin, and derivatives thereof); ciprofloxacin; a fluoroquinolone (e.g., cinoxacin, nalidixic acid, oxolinic acid, piromidic acid, pipemidic acid, rosoxacin, ciproflaxcin, enoxacin, fleroxacin, lomefloxacin, nadifloxacin, norfloxacin, ofloxacin, perfloxacin, rufloxacin, balofloxacin, grepafloxacin, levofloxacin, pazufloxacin, sparfloxacin, temfloxacon, tosufloxacin, clinafloxacin, gatifloxacin, gemifloxacin, moxifloxacin, sitafloxacin, trovafloxacin, prulifloxacin, delafloxacin, nemonoxacin, zabofloxacin, JNJ-Q2, and derivatives thereof); a quinolone (e.g. sparfloxacin, ciprofloxacin, norfloxacin, and derivatives thereof); kanamycin; and an aminoglycoside (e.g. streptomycin, gentamicin, kanamycin A, tobramycin, neomycin B, neomycin C, framycetin, paromomycin, ribostamycin, amikacin, arbekacin, bekanamycin (kanamycin B), dibekacin, spectinomycin, hygromycin B, paromomycin sulfate, netilmicin, sisomicin, isepamicin, verdamicin, astromicin, neamine, ribostamycin, and paromomycinlividomycin, and derivatives thereof). In some embodiments of any of the aspects, the antibiotic is selected from the group consisting of: vancomycin; an inhibitor of cell wall synthesis; rifampin; an ansamycin; a rifamycin; ciprofloxacin; a fluoroquinolone; and a quinolone. In some embodiments of any of the aspects, the antibiotic is selected from the group consisting of: vancomycin; rifampin; a rifamycin; ciprofloxacin; and a fluoroquinolone. In some embodiments of any of the aspects, the antibiotic is selected from the group consisting of: vancomycin; rifampin; and ciprofloxacin.

In some embodiments of any of the aspects, the anti-inflammatory is selected from non-steroidal anti-inflammatory drugs (NSAIDs—such as aspirin, ibuprofen, or naproxen); corticosteroids, including glucocorticoids (e.g. cortisol, prednisone, prednisolone, methylprednisolone, dexamethasone, betamethasone, triamcinolone, and beclometasone); methotrexate; sulfasalazine; leflunomide; anti-TNF medications; cyclophosphamide; pro-resolving drugs; mycophenolate, and the like.

In some embodiments of any of the aspects, the methods described herein relate to treating a subject having or diagnosed as having an infection. Subjects having an infection can be identified by a physician using current methods of diagnosing infections. Symptoms and/or complications of infections which characterize these conditions and aid in diagnosis are well known in the art and include but are not limited to, fever, microbial growth, impairment of infected tissues and/or organs etc. Tests that may aid in a diagnosis of, e.g. infection include, but are not limited to, microbial culture of samples. Exposure to risk factors for infections can also aid in determining if a subject is likely to have an infection or in making a diagnosis of infection.

The compositions and methods described herein can be administered to a subject having or diagnosed as having a lung infection and/or lung inflammation. In some embodiments of any of the aspects, the methods described herein comprise administering an effective amount of compositions described herein, e.g. an inhibitor of IP6K1 to a subject in order to alleviate a symptom of a lung infection and/or lung inflammation. As used herein, "alleviating a symptom" is ameliorating any condition or symptom associated with the lung infection and/or lung inflammation. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, or injection administration. Administration can be local or systemic.

The term "effective amount" as used herein refers to the amount of active agent needed to alleviate at least one or more symptom of the disease or disorder, and relates to a sufficient amount of pharmacological composition to provide the desired effect. The term "therapeutically effective amount" therefore refers to an amount of the active agent that is sufficient to provide a particular effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the active agent, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for bacterial counts, among others. The dosage can be determined by a physician and adjusted, as necessary, to suit observed effects of the treatment.

In some embodiments of any of the aspects, the technology described herein relates to a pharmaceutical composition comprising an inhibitor of IP6K1 as described herein, and optionally a pharmaceutically acceptable carrier. In some embodiments of any of the aspects, the active ingredients of the pharmaceutical composition comprise an inhibitor of IP6K1 as described herein. In some embodiments of any of the aspects, the active ingredients of the pharmaceutical composition consist essentially of an inhibitor of IP6K1 as described herein. In some embodiments of any of the aspects, the active ingredients of the pharmaceutical composition consist of an inhibitor of IP6K1 as described herein. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments of any of the aspects, the carrier inhibits the degradation of the active agent, e.g. an inhibitor of IP6K1 as described herein.

In some embodiments of any of the aspects, the pharmaceutical composition comprising an inhibitor of IP6K1 as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of an inhibitor of IP6K1 as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of an inhibitor of IP6K1 as disclosed herein can also be incorporated into the parenteral dosage forms of the disclosure, including conventional and controlled-release parenteral dosage forms.

Pharmaceutical compositions comprising an inhibitor of IP6K1 can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments of any of the aspects, the inhibitor of IP6K1 can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008, 719; 5,674,533; 5,059,595; 5,591,767; 5,120,548; 5,073, 543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

Im some embodiments of any of the aspects, the inhibitor of IP6K1 described herein is administered as a monotherapy, e.g., another treatment for the lung infection and/or lung inflammation is not administered to the subject.

In some embodiments of any of the aspects, the methods described herein can further comprise administering a second agent and/or treatment to the subject, e.g. as part of a combinatorial therapy. Non-limiting examples of second agents or treatments can include, e.g., ventilation, antimicrobials, anti-inflammatories, and the like.

In certain embodiments, an effective dose of a composition comprising an inhibitor of IP6K1 as described herein can be administered to a patient once. In certain embodiments, an effective dose of a composition comprising an inhibitor of IP6K1 can be administered to a patient repeatedly. For systemic administration, subjects can be administered a therapeutic amount of a composition comprising an inhibitor of IP6K1, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments of any of the aspects, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the active agent. The desired dose or amount of activation can be administered at one time or divided into subdoses, e.g., 2-4 subdoses and administered over a period of time, e.g., at appropriate intervals through the day or other appropriate schedule. In some embodiments of any of the aspects, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising an inhibitor of IP6K1 can be administered over a period of time, such as over a 5 minute, 10 minute, 15 minute, 20 minute, or 25 minute period.

The dosage ranges for the administration of an inhibitor of IP6K1, according to the methods described herein depend upon, for example, the form of the inhibitor, its potency, and the extent to which symptoms, markers, or indicators of a condition described herein are desired to be reduced, for example the percentage reduction desired for bacterial counts or neutrophil accumulation or the extent to which, for example, immune responses are desired to be induced. The dosage should not be so large as to cause adverse side effects, such as immunosuppression. Generally, the dosage will vary with the age, condition, and sex of the patient and can be determined by one of skill in the art. The dosage can also be adjusted by the individual physician in the event of any complication.

The efficacy of an inhibitor of IP6K1 in, e.g. the treatment of a condition described herein, or to induce a response as described herein can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. bacterial counts, neutrophil activity, neutrophil accumulation, polyp levels, or the like. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein, for example treatment of pneumonia. When using an experimental animal model, efficacy of treatment is evidenced when a statistically significant change in a marker is observed, e.g. bacterial counts or survival.

In vitro and animal model assays are provided herein which allow the assessment of a given dose of an inhibitor of IP6K1.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments of any of the aspects, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments of any of the aspects, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments of any of the aspects, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of a condition. A subject can be male or female.

A subject can be one who has been previously diagnosed with or identified as suffering from or having a condition in need of treatment or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments of any of the aspects, the polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to the assays described below herein. A functional fragment can comprise conservative substitutions of the sequences disclosed herein.

In some embodiments of any of the aspects, the polypeptide described herein can be a variant of a sequence described herein. In some embodiments of any of the aspects, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

A variant amino acid or DNA sequence can be at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA. Suitable RNA can include, e.g., mRNA.

The term "expression" refers to the cellular processes involved in producing RNA and proteins and as appropriate, secreting proteins, including where applicable, but not limited to, for example, transcription, transcript processing, translation and protein folding, modification and processing. Expression can refer to the transcription and stable accumulation of sense (mRNA) or antisense RNA derived from a nucleic acid fragment or fragments of the invention and/or to the translation of mRNA into a polypeptide.

In some embodiments of any of the aspects, the expression of a biomarker(s), target(s), or gene/polypeptide described herein is/are tissue-specific. In some embodiments of any of the aspects, the expression of a biomarker(s), target(s), or gene/polypeptide described herein is/are global. In some embodiments of any of the aspects, the expression of a biomarker(s), target(s), or gene/polypeptide described herein is systemic.

"Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

"Marker" in the context of the present invention refers to an expression product, e.g., nucleic acid or polypeptide which is differentially present in a sample taken from subjects having having increased neutrophil accumulation and/or polyP, as compared to a comparable sample taken from control subjects (e.g., a healthy subject). The term "biomarker" is used interchangeably with the term "marker."

In some embodiments of any of the aspects, the methods described herein relate to measuring, detecting, or determining the level of at least one marker. As used herein, the term "detecting" or "measuring" refers to observing a signal from, e.g. a probe, label, or target molecule to indicate the presence of an analyte in a sample. Any method known in the art for detecting a particular label moiety can be used for detection. Exemplary detection methods include, but are not limited to, spectroscopic, fluorescent, photochemical, biochemical, immunochemical, electrical, optical or chemical methods. In some embodiments of any of the aspects, measuring can be a quantitative observation.

In some embodiments of any of the aspects, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

In some embodiments of any of the aspects, the inhibitor described herein is exogenous. In some embodiments of any of the aspects, the inhibitor described herein is ectopic. In some embodiments of any of the aspects, the inhibitor described herein is not endogenous.

The term "exogenous" refers to a substance present in a cell other than its native source. The term "exogenous" when used herein can refer to a nucleic acid (e.g. a nucleic acid encoding a polypeptide) or a polypeptide that has been introduced by a process involving the hand of man into a biological system such as a cell or organism in which it is not normally found and one wishes to introduce the nucleic acid or polypeptide into such a cell or organism. Alternatively, "exogenous" can refer to a nucleic acid or a polypeptide that has been introduced by a process involving the hand of man into a biological system such as a cell or organism in which it is found in relatively low amounts and one wishes to increase the amount of the nucleic acid or polypeptide in the cell or organism, e.g., to create ectopic expression or levels. In contrast, the term "endogenous" refers to a substance that is native to the biological system or cell. As used herein, "ectopic" refers to a substance that is found in an unusual location and/or amount. An ectopic substance can be one that is normally found in a given cell, but at a much lower amount and/or at a different time. Ectopic also includes substance, such as a polypeptide or nucleic acid that is not naturally found or expressed in a given cell in its natural environment.

In some embodiments of any of the aspects, a nucleic acid described herein, e.g., an inhibitory nucleic acid is or is provided or administered when it is comprised by a vector. In some of the aspects described herein, a nucleic acid sequence is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

In some embodiments of any of the aspects, the vector is recombinant, e.g., it comprises sequences originating from at least two different sources. In some embodiments of any of the aspects, the vector comprises sequences originating from at least two different species. In some embodiments of any of the aspects, the vector comprises sequences originating from at least two different genes, e.g., it comprises a fusion protein or a nucleic acid encoding an expression product which is operably linked to at least one non-native (e.g., heterologous) genetic control element (e.g., a promoter, suppressor, activator, enhancer, response element, or the like).

In some embodiments of any of the aspects, the vector or nucleic acid described herein is codon-optomized, e.g., the native or wild-type sequence of the nucleic acid sequence has been altered or engineered to include alternative codons such that altered or engineered nucleic acid encodes the same polypeptide expression product as the native/wild-type sequence, but will be transcribed and/or translated at an improved efficiency in a desired expression system. In some embodiments of any of the aspects, the expression system is an organism other than the source of the native/wild-type sequence (or a cell obtained from such organism). In some embodiments of any of the aspects, the vector and/or nucleic acid sequence described herein is codon-optimized for expression in a mammal or mammalian cell, e.g., a mouse, a murine cell, or a human cell. In some embodiments of any of the aspects, the vector and/or nucleic acid sequence described herein is codon-optimized for expression in a human cell. In some embodiments of any of the aspects, the vector and/or nucleic acid sequence described herein is codon-optimized for expression in a yeast or yeast cell. In some embodiments of any of the aspects, the vector and/or nucleic acid sequence described herein is codon-optimized for expression in a bacterial cell. In some embodiments of any of the aspects, the vector and/or nucleic acid sequence described herein is codon-optimized for expression in an *E. coli* cell.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification.

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring any nucleic acids into cells either in vitro or in vivo. Numerous forms of viral vectors are known in the art.

It should be understood that the vectors described herein can, In some embodiments of any of the aspects, be combined with other suitable compositions and therapies. In some embodiments of any of the aspects, the vector is episomal. The use of a suitable episomal vector provides a means of maintaining the nucleotide of interest in the subject in high copy number extra chromosomal DNA thereby eliminating potential effects of chromosomal integration.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. a lung infection and/or lung inflammation. The term "treating" includes reducing or alleviating at least one adverse effect or symptom of a condition, disease or disorder associated with a condition. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in in nature.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject. In some embodiments of any of the aspects, administration comprises physical human activity, e.g., an injection, act of ingestion, an act of application, and/or manipulation of a delivery device or machine. Such activity can be performed, e.g., by a medical professional and/or the subject being treated.

As used herein, "contacting" refers to any suitable means for delivering, or exposing, an agent to at least one cell. Exemplary delivery methods include, but are not limited to, direct delivery to cell culture medium, perfusion, injection, or other delivery method well known to one skilled in the art. In some embodiments of any of the aspects, contacting comprises physical human activity, e.g., an injection; an act of dispensing, mixing, and/or decanting; and/or manipulation of a delivery device or machine.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments of any of the aspects, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

EXAMPLES

Example 1: Inhibition of IP6K1 Suppresses Neutrophil-Mediated Pulmonary Damage in Bacterial Pneumonia IP6K1-mediated polyP production by platelets promotes neutrophil-platelet aggregation and neutrophil accumulation in bacterial pneumonia.

The significance of developing host-modulating personalized therapies to counteract the growing threat of antimicrobial resistance is well recognized, since such resistance cannot be overcome using microbe-centered strategies alone. Immune host defenses must be finely controlled during infection to balance pathogen clearance with unwanted inflammation-induced tissue damage. Thus, an ideal antimicrobial treatment would enhance bactericidal activity while preventing neutrophilic inflammation. It is reported herein that disrupting the inositol hexakisphosphate kinase 1 (Ip6k1) gene or pharmacologically inhibiting IP6K1 activity using the specific inhibitor TNP efficiently and effectively enhanced host bacterial killing but reduced pulmonary neutrophil accumulation, minimizing the lung damage caused by both gram-positive and gram-negative bacterial pneumonia. IP6K1-mediated inorganic polyphosphate (polyP) production by platelets was essential for infection-induced neutrophil-platelet aggregate (NPA) formation and facilitated neutrophil accumulation in alveolar spaces during bacterial pneumonia. IP6K1 inhibition reduced serum polyP levels, which regulated NPAs by triggering the bradykinin pathway and bradykinin-mediated neutrophil activation. Thus, identified herein is a mechanism that enhances host defenses whilst simultaneously suppressing neutrophil-mediated pulmonary damage in bacterial pneumonia. IP6K1 is, therefore, a legitimate therapeutic target for such disease.

Higher inositol pyrophosphates, are ubiquitous and have diverse cellular functions, in neutrophils (1). IP7 inhibits PtdIns(3,4,5)P3-mediated plasma membrane translocation of PH domain-containing proteins. Via this mechanism, IP7 acts as a key modulator of PtdIns(3,4,5)P3-mediated neutrophil functions such as phagocytosis, NADPH oxidase-mediate reactive oxygen species (ROS) production, and bacterial killing. IP6K1 appears to be the main enzyme responsible for IP7 production in neutrophils; as a result, IP6K1-deficient neutrophils exhibit increased PtdIns(3,4,5)P3 signaling, enhanced phagocytic and bactericidal capacity, and elevated NADPH oxidase-mediated superoxide production.

Described herein is IP6K1's role in neutrophil function in bacterial pneumonia models. IP6K1 expression in platelets was required for LPS-induced formation of the neutrophil-platelet aggregates (NPA) and essential for neutrophil accumulation in the alveolar spaces during bacterial pneumonia (2-6). IP6K1 function in NPA formation was mainly mediated by inorganic polyphosphate (polyP), which regulated NPA by triggering the bradykinin pathway and bradykinin-mediated neutrophil activation.

Figure 7A:
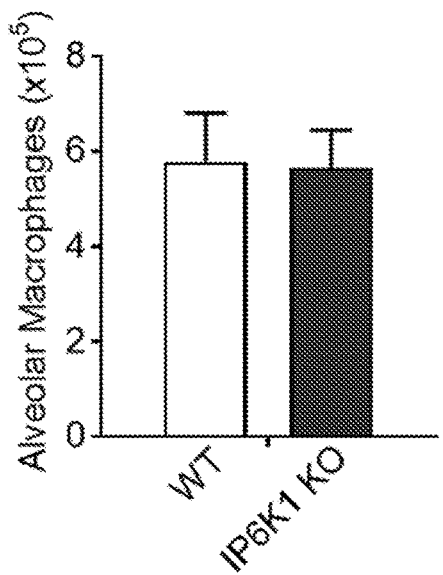
FIGS. 7A-7D demonstrate that disruption of InsP6K1 does not alter alveolar macrophage number, expression of surfactant proteins/antimicrobial peptides, and neutrophil apoptosis during lung inflammation.
Figure 7B:
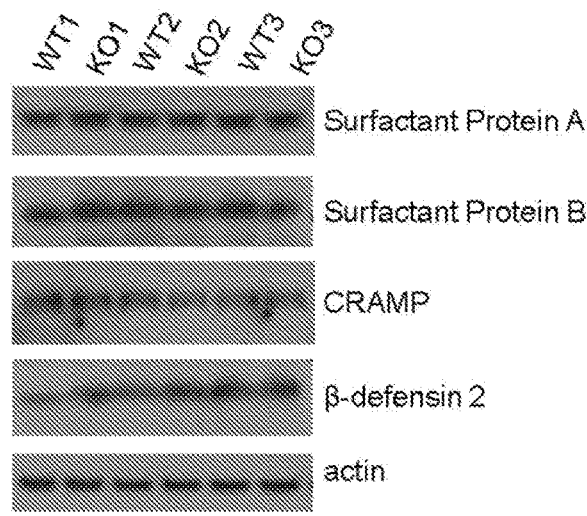

IP6K1 disruption leads to enhanced bacterial killing, reduced neutrophil accumulation, and alleviates lung damage in bacteria pneumonia. Disruption of IP6K1 in neutrophils upregulates PtdIns(3,4,5)P3 signaling in a mouse bacteria-induced peritonitis model, enhancing bacterial killing by the host (1). Similarly, bacterial clearance was also enhanced in IP6K1-deficient mice in a bacteria-induced pneumonia model (FIGS. 1A-1L). Bacterial pneumonia was induced by intratracheal instillation of *Escherichia coli*, a common Gram-negative pathogen. The lung bacterial burden, as measured by colony forming units (cfu), was reduced by up to 1 log(10) CFU/lung compared to wildtype (WT) mice at each time point examined (FIG. 1A). The number of alveolar macrophages in unchallenged mice and the amount of surfactant protein A, surfactant protein B, cathelin-related antimicrobial peptide (CRAMP), and beta-defensin 2 in the lungs after the infection were assessed (FIG. 7A-7B). No significant differences were detected between WT and IP6K1-deficient mice, consistent with the notion that the elevated bacterial killing observed in IP6K1-deficient mice may be mainly mediated by neutrophils.

Figure 1B:
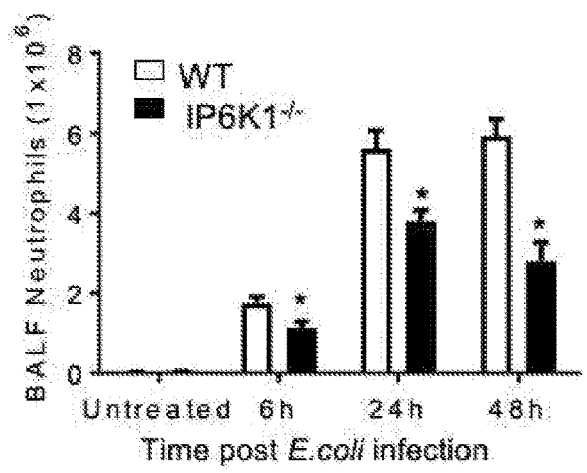
Figure 1C:
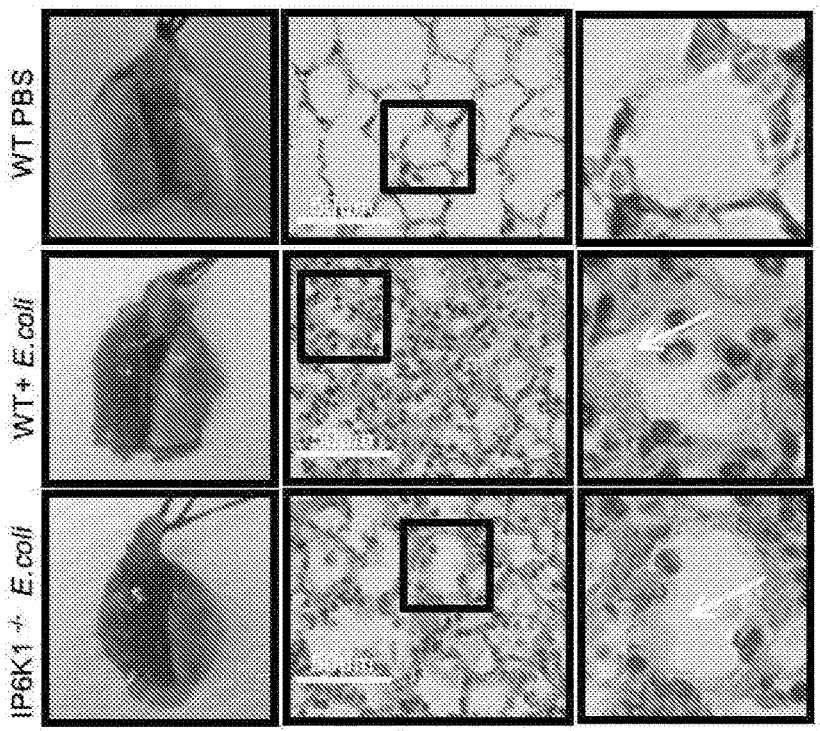
Figure 1D:
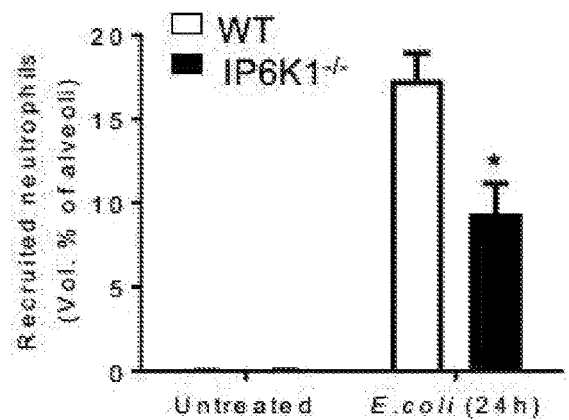
Figure 7C:
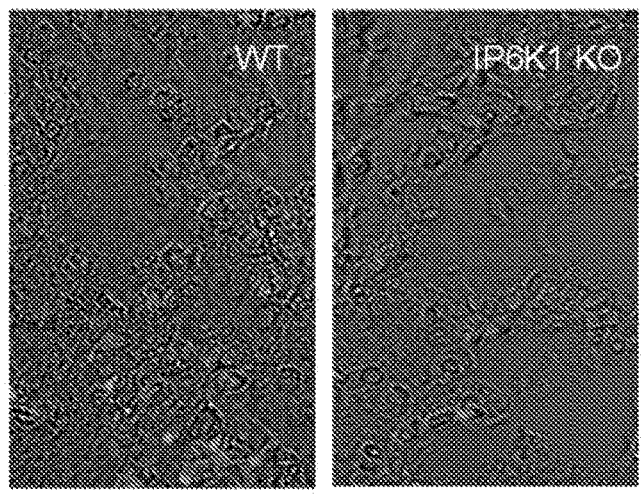
Figure 7D:
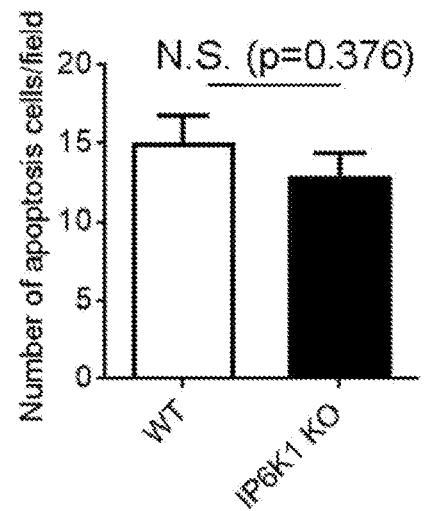
Figure 8A:
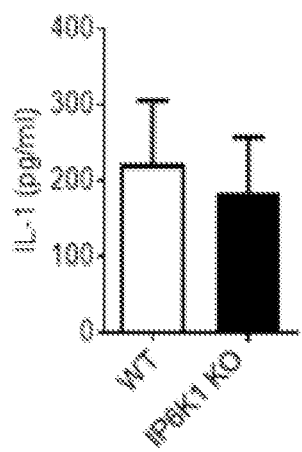
FIGS. 8A-8E demonstrate that disruption of InsP6K1 does not affect the production of proinflammatory cytokines/chemokines. Mice were intratracheally instilled with $2\times10^6$ CFU of *E. coli* and sacrificed after 24 h. BALF was collected using ice-cold PBS/15 mM EDTA. Cytokines/chemokine (IL-1, IL-6, TNF-α, KC and MIP-2) levels were determined using specific enzyme-linked immunosorbent assay (ELISA) kits. Data shown are means±SEM of ≥5 experiments. p<0.05 was defined as significant.
Figure 8B:
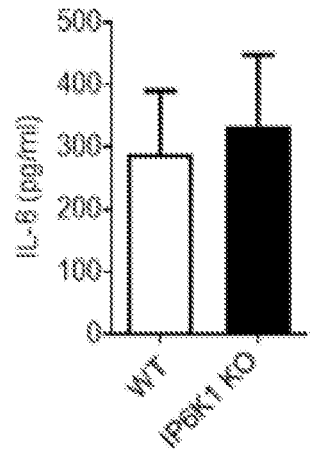
Figure 8C:
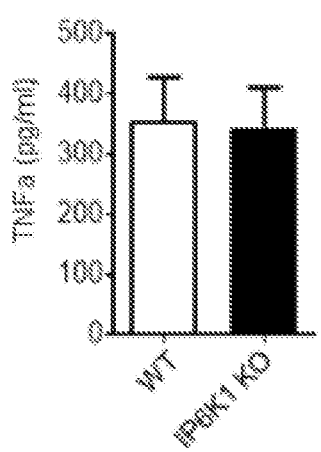
Figure 8D:
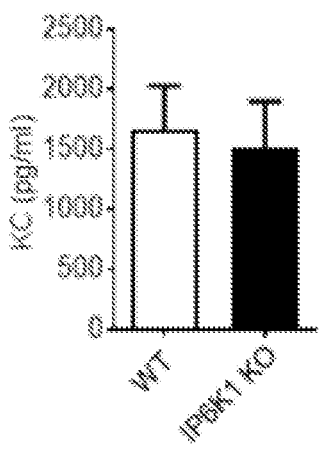
Figure 8E:
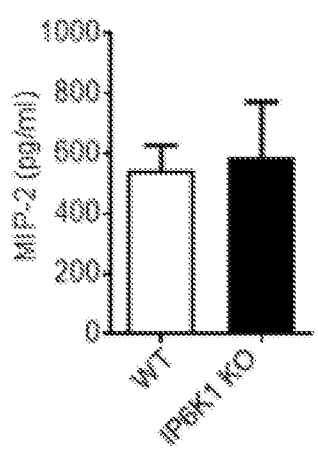

Intriguingly, although IP6K1 did not regulate neutrophil accumulation in the peritonitis model (1), IP6K1 deficiency led to a reduction in pulmonary neutrophil accumulation in the pneumonia model (FIG. 1B). During bacterial pneumonia, the number of neutrophils in the bronchoalveolar lavage fluid (BALF) increased gradually, reaching over 6×106 cells/lung 24 h after bacterial instillation. Bacteria-induced neutrophil accumulation was substantially lower in IP6K1-deficient mice, with only 4×106 neutrophils recruited to each inflamed lung 24 h after bacterial instillation (FIG. 1B). The number of emigrated neutrophils in alveolar spaces was also assessed by morphometry of lung tissue sections (7): very few neutrophils were present in the alveolar air spaces of mice challenged with PBS, but bacterial infection induced substantial neutrophil accumulation in alveolar air spaces (FIG. 1C-1D), with IP6K1 disruption decreasing the number of neutrophils in the alveolar air spaces in bacteria-challenged mice (FIG. 1C-1D). Similar to in the peritonitis model (1), IP6K1 disruption did not alter the rate of apoptosis of recruited neutrophils (FIG. 7C-7D), indicating that apoptosis was not responsible for reduced neutrophil accumulation. Additionally, the levels of proinflammatory cytokines/chemokines, including IL-1, IL-6, TNF-α, KC, and MIP2, in the BALF were the same between IP6K1-deficient and WT mice in bacterial pneumonia (FIG. 8).

Figure 1E:
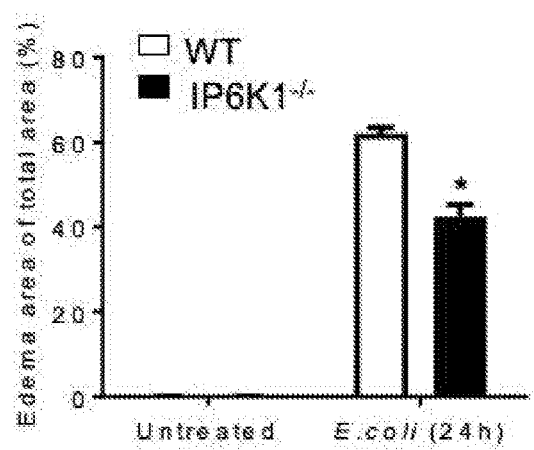
Figure 1F:
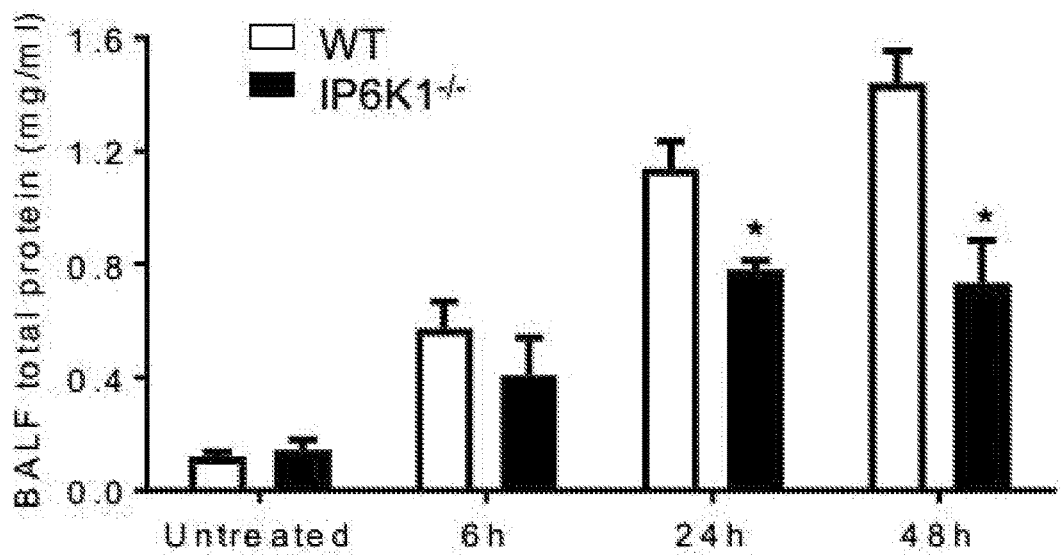
Figure 1G:
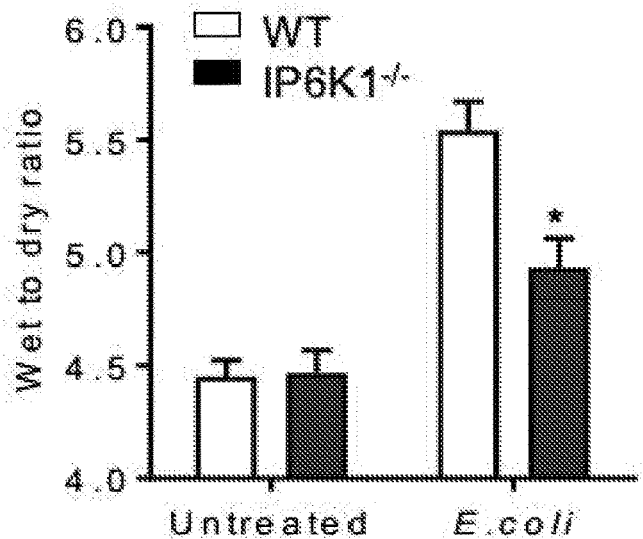
Figure 1H:
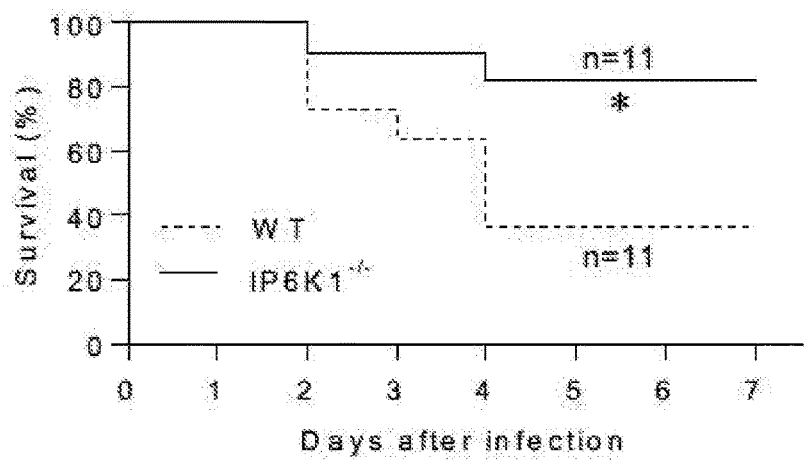

It was next investigated whether enhanced bacterial killing and reduced neutrophil accumulation in IP6K1-deficient mice alleviated lung damage. Pulmonary edema is a well-characterized sign of lung inflammation and can be directly detected and measured in lung sections by microscopy and quantified by morphometry. Disrupting IP6K1 improved the histologic integrity of the lungs and reduced lung edema formation (FIG. 1E). Consistent with reduced edema formation, total protein levels in the BALF of IP6K1-deficient mice were much lower than in WT mice at each time point examined (FIG. 1F). Additionally, the lung wet-to-dry ratio, which also measures the change in the capillary permeability, was reduced in infected IP6K1-deficient mice compared to WT mice (FIG. 1G). IP6K1 deficiency also increased the survival rate of bacteria-challenged mice in a more severe pneumonia model induced by higher dose of live *E. coli* (FIG. 1H). Taken together, these results indicate that disrupting IP6K1 protects mice from bacterial infection-induced lung damage.

Figure 1I:
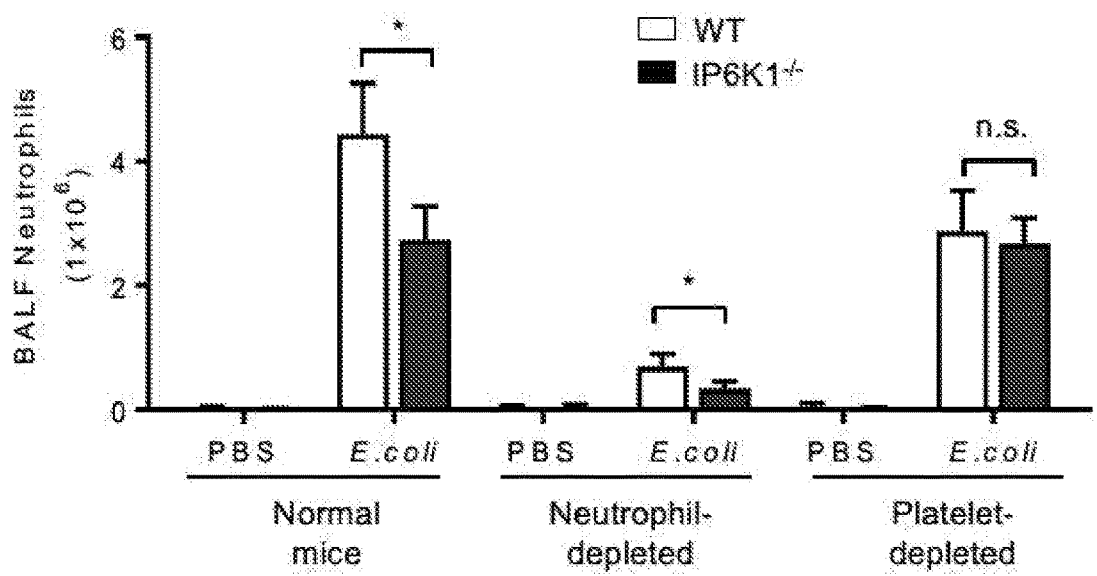
Figure 1J:
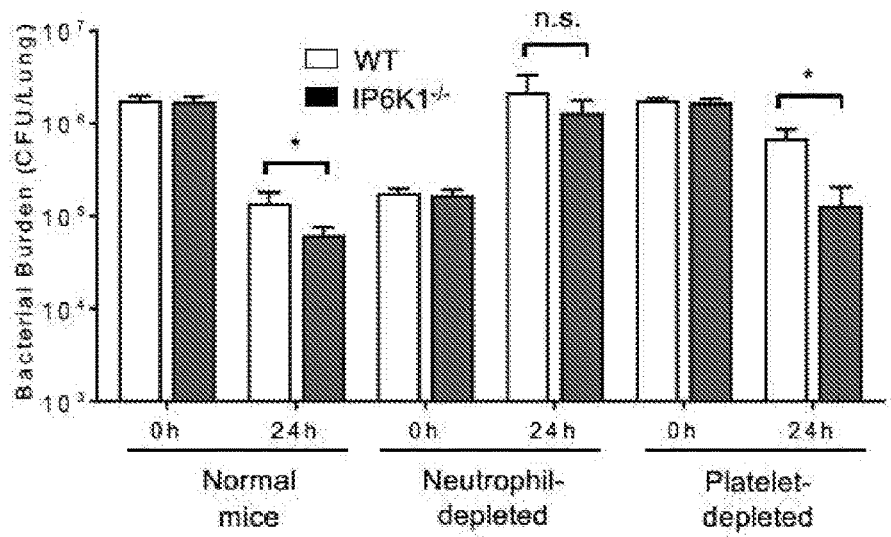
Figure 1K:
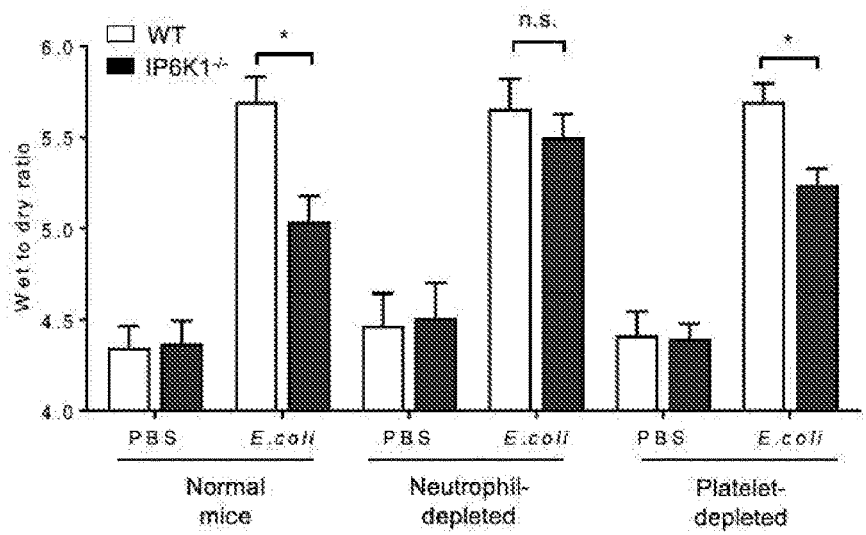
Figure 1L:
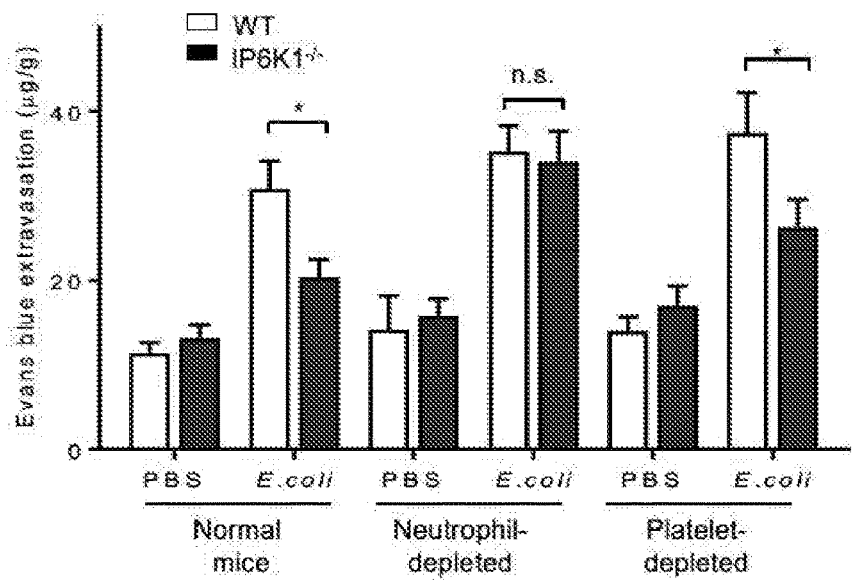
Figures 9A, 9B, 9C, 9D, 9E:
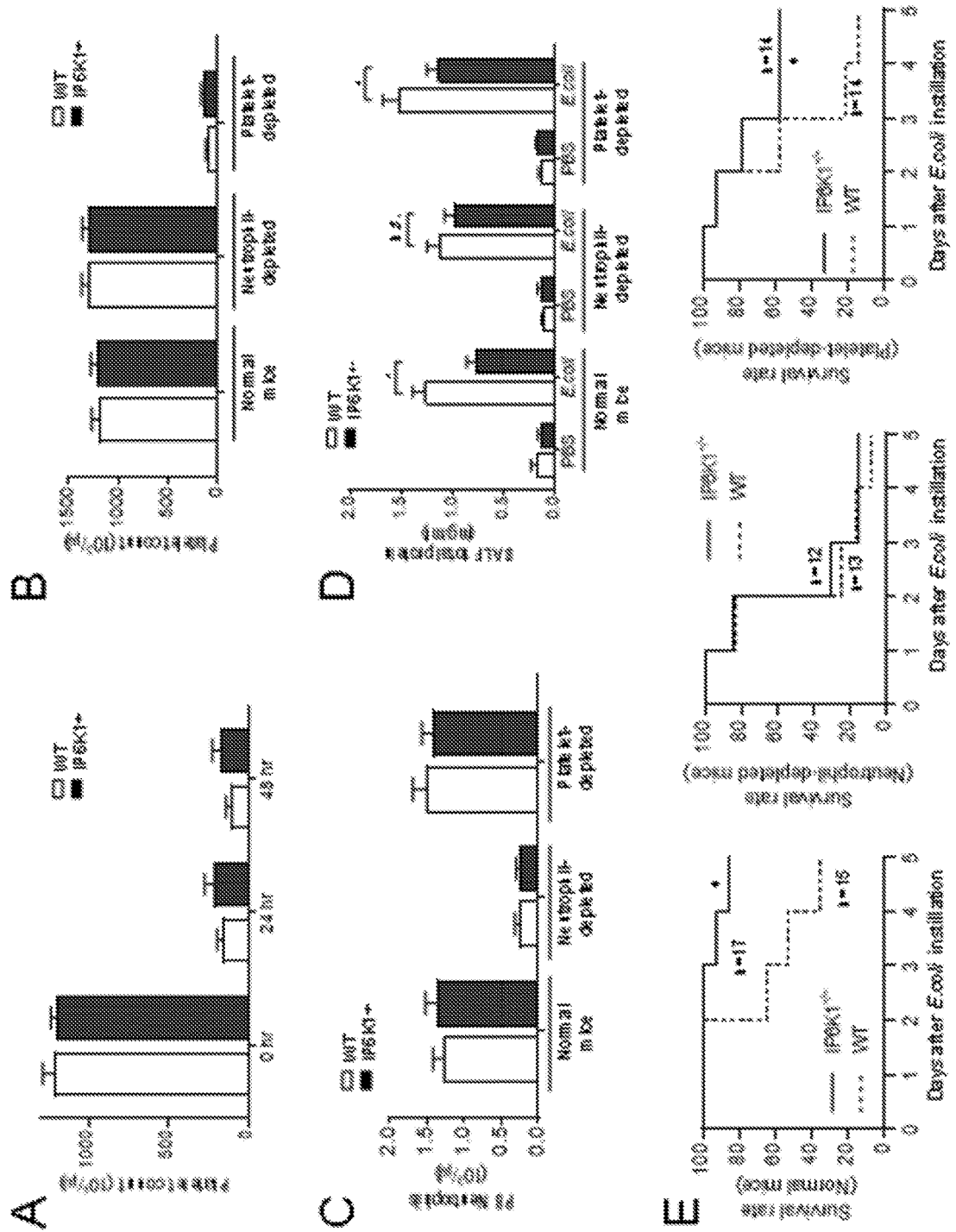
FIGS. 9A-9E demonstrate *E. coli*-induced pneumonia in untreated, neutrophil-depleted, and platelet-depleted mice.

Neutrophils are key players in host defense and inflammation-elicited lung injury. Consistently, neutrophil-depletion impaired host defense against *E. coli* infection (FIG. 1I-1K, FIG. 9A-9E); bacteria kept proliferating in neutropenic mice (FIG. 1J). Although peripheral blood neutrophil count was reduced to a similar level in neutrophil-depleted WT and IP6K1-deficient mice (FIG. 9C), a reduction of neutrophil accumulation in the inflamed lungs was still detected in the IP6K1-deficient mice (FIG. 1I). Nevertheless, the difference in bacteria clearance (FIG. 1J), *E. coli*-elicited lung damage (FIG. 1K-1L, FIG. 9D) and the related death (FIG. 9E) could not be detected between neutrophil-depleted WT and IP6K1KO mice anymore, indicating that the lung damage in neutropenic mice was mainly mediated by a neutrophil-independent mechanism.

Numerous studies showed that platelets have the capacity to promote neutrophil accumulation (8-11). As previously reported (2-6), platelet depletion substantially reduced *E. coli*-induced neutrophil presence in the inflamed lungs (FIG. 1I). Intriguingly, the reduced neutrophil accumulation observed in IP6K1-deficient mice was diminished in platelet-depleted mice, indicating that platelets contributed to IP6K1 function in *E. coli*-elicited pulmonary inflammation (FIG. 1I). Noticeably, although similar number of neutrophils were recruited to the lungs of platelet-depleted IP6K1 KO mice as platelet-depleted WT mice, the bacterial killing capability was elevated in these mice compared to platelet-depleted WT mice (FIG. 1J). This is in agreement with the observation that IP6K1-deficient neutrophils exhibit increased PtdIns(3,4,5)P3 signaling, enhanced phagocytic and bactericidal capacity, and elevated NADPH oxidase-mediated superoxide production (1). Consistently, *E. coli*-elicited lung damage (FIG. 1K-1L, FIG. 9D) and the related death (FIG. 9E) were also reduced in platelet-depleted IP6K1-deficient mice. Taken together, these results demonstrate that both neutrophils and platelets contributed to IP6K1 function in *E. coli*-elicited bacteria pneumonia.

Figures 10A, 10B, 10C, 10D, 10E:
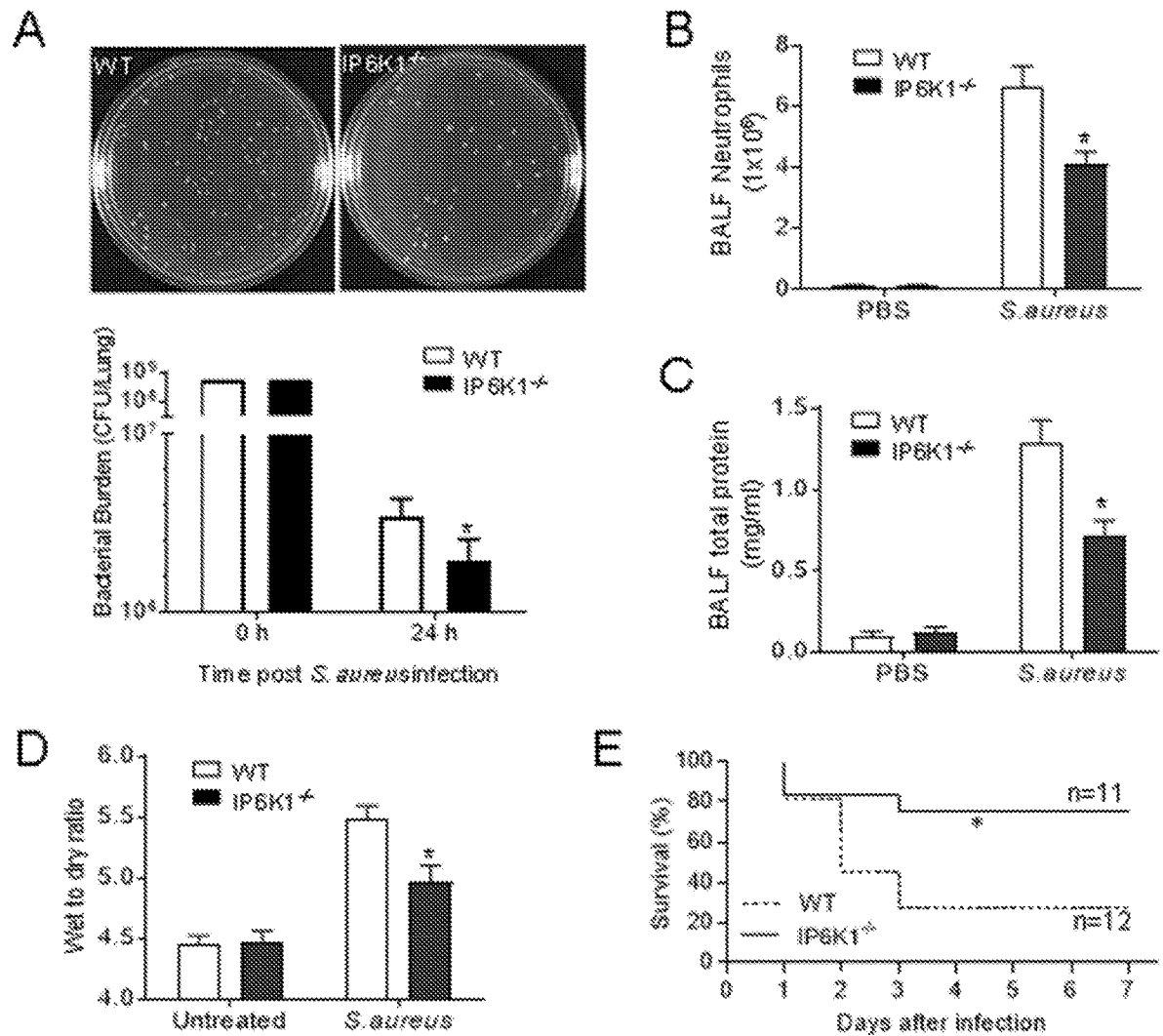
FIGS. 10A-10E demonstrate that disrupting IP6K1 enhances bacterial killing and reduces lung damage in *S. aureus*-induced pneumonia. Mice were intratracheally instilled with $5.13\times10^8$ cfu of *S. aureus* and euthanized at indicated time points.

IP6K1 disruption alleviates lung damage in pneumonia induced by gram positive bacteria *S. aureus* NPA formation facilitates neutrophil accumulation in alveolar spaces in various types of acute lung inflammation, not just in *E. coli*-induced lung inflammation (2-5). Thus, it was next explored whether IP6K1 disruption can also alleviate lung damage in pneumonia induced by gram positive bacteria. Pneumonia was induced by intratracheal instillation of *Staphylococcus aureus* (*S. aureus*), a commonly used and clinically relevant gram-positive coccal bacterium. Similar to what was observed in *E. coli*-induced pneumonia, the clearance of *S. aureus* was also enhanced in IP6K1-deficient mice (FIG. 10). The lung bacterial burden was substantially reduced compared to wildtype (WT) mice 24 h after bacterial instillation (FIG. 10A). IP6K1 deficiency also led to a reduction in pulmonary neutrophil accumulation in the inflamed lungs (FIG. 10B). Consistently, pneumonia induced-vascular leakage and lung damage, measured as total protein levels in the BALF and lung wet-to-dry ratio, in IP6K1-deficient mice was much less severe than in WT mice (FIG. 10C-10D). In addition, the pneumonia-related mortality was reduced in the IP6K1-deficient mice (FIG. 10E). Taken together, these results reveal that disrupting IP6K1 protects hosts from infection-induced lung damage in both gram negative and gram positive bacterial pneumonia.

Figure 2A:
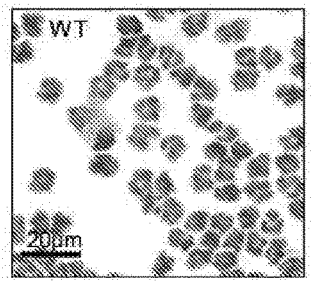
Figure 2A:
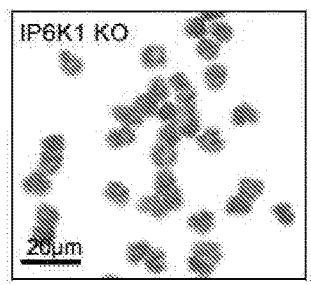
Figure 2B:
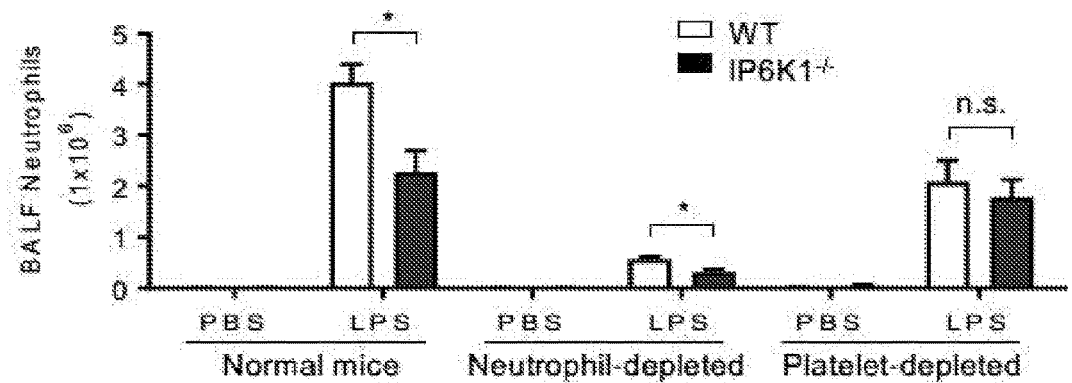
Figure 2C:
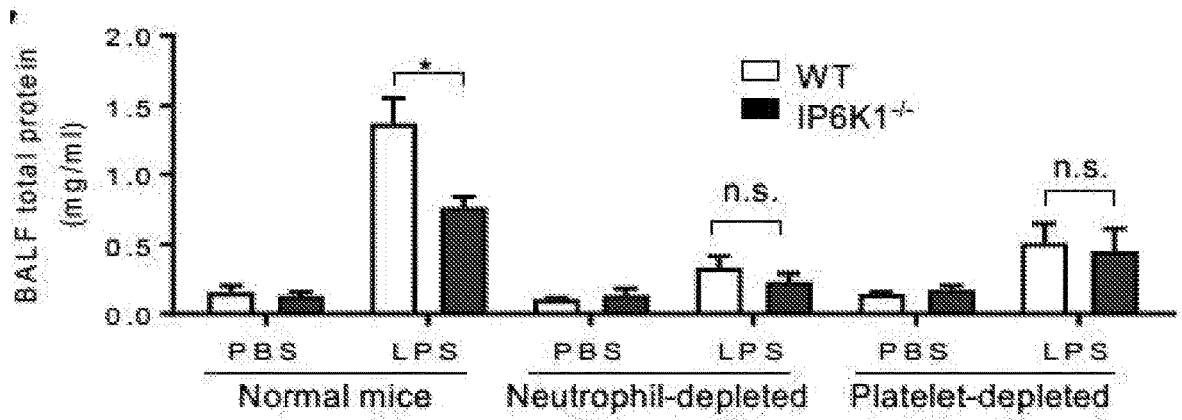
Figure 2D:
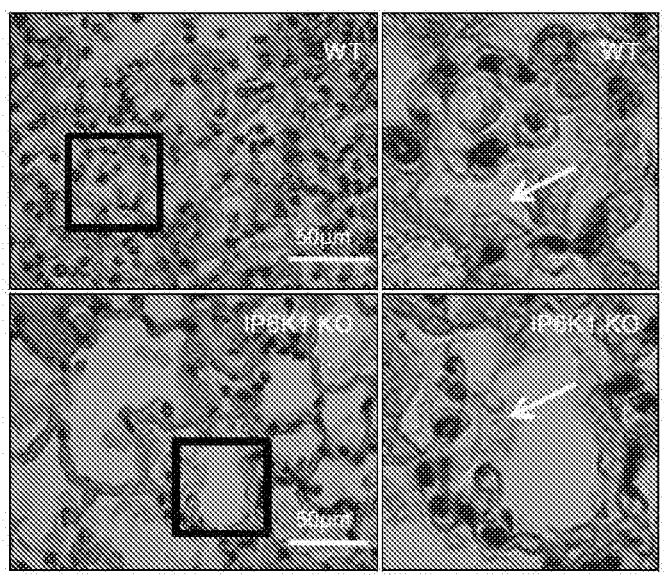
Figure 2E:
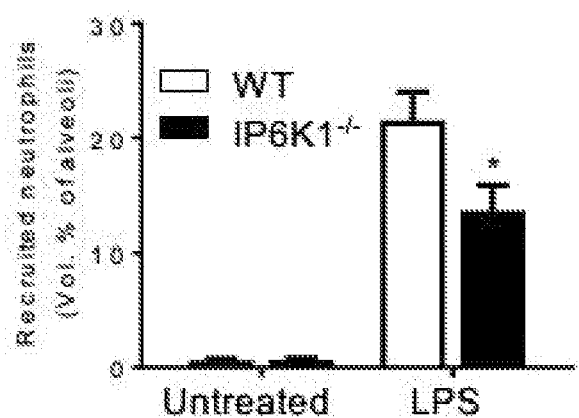
Figure 2F:
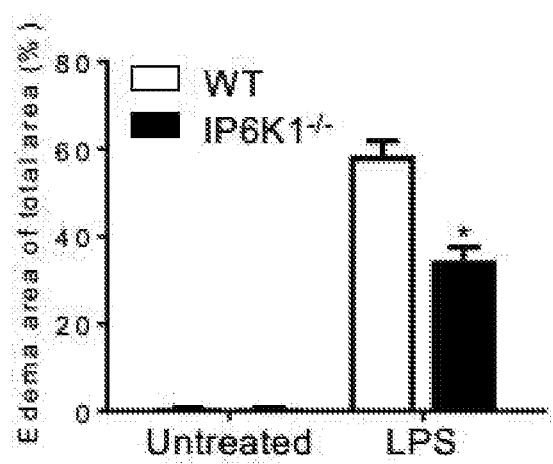
Figure 2G:
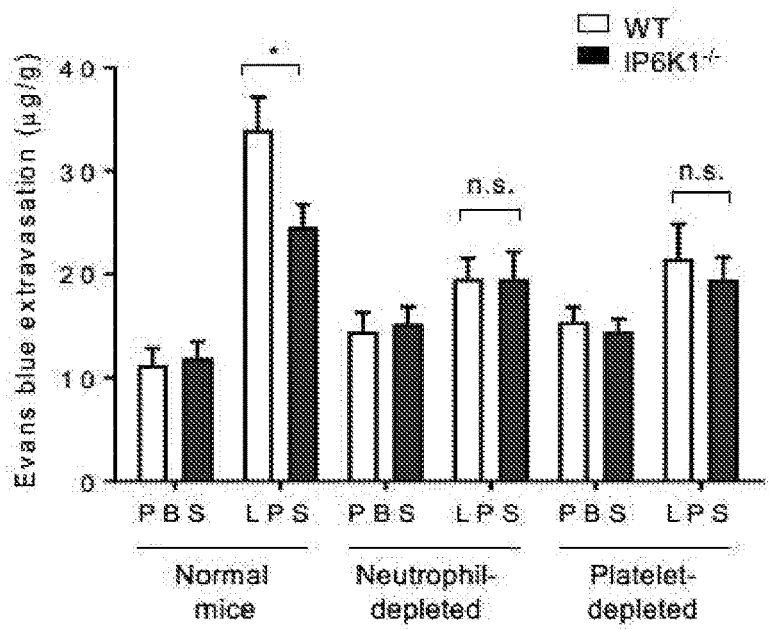
Figure 2H:
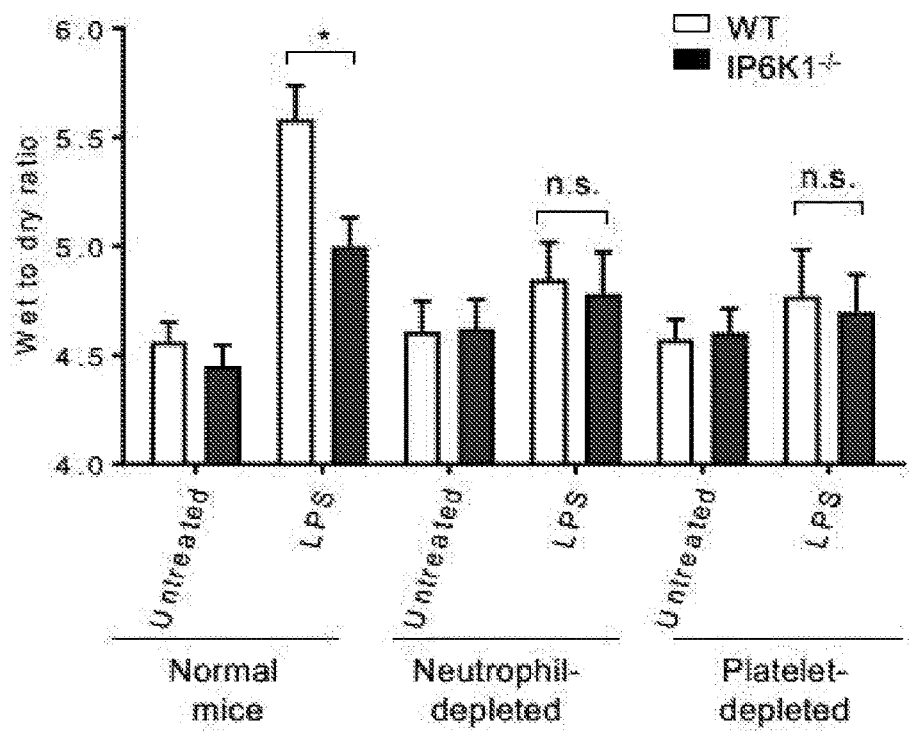
Figure 2I:
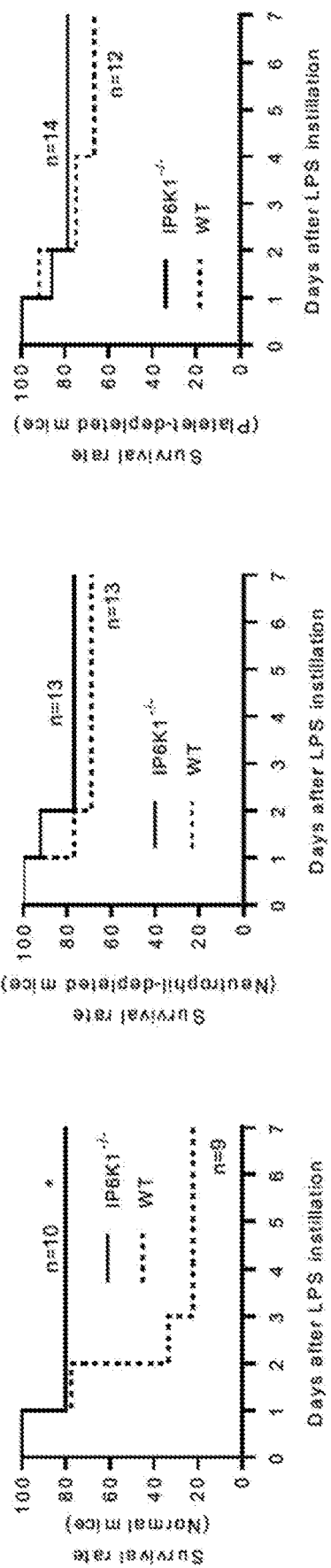

IP6K1 disruption reduces neutrophil accumulation and alleviates lung damage in LPS-induced lung inflammation. To directly assess whether IP6K1 disruption can reduce neutrophil accumulation independent of bacterial clearance, neutrophil accumulation was examined in a lipopolysaccharide (LPS)-induced acute lung injury (ALI) model. IP6K1 disruption similarly diminished LPS-induced neutrophil accumulation in the inflamed lung as assessed by both quantification of BALF neutrophil numbers (FIGS. 2A-2B). As expected, reduced neutrophil accumulation in the lungs substantially alleviated inflammation-induced lung damage. The total BALF protein level (FIG. 2C) and edema formation (FIG. 2D-2F) decreased in the lungs of IP6K1-deficient mice compared to WT. Finally, vascular permeability was directly assessed using Evans blue, an albumin-binding dye (FIG. 2G), and by measuring lung wet-to-dry ratio (FIG. 2H). Infection-induced increases in pulmonary vascular permeability were partially suppressed in IP6K1-deficient mice. Consistently, ALI-related mortality was reduced in these mice (FIG. 2I). Thus, disrupting IP6K1 reduced neutrophil accumulation and alleviated lung injury independent of increased bactericidal effects.

Figure 2J:
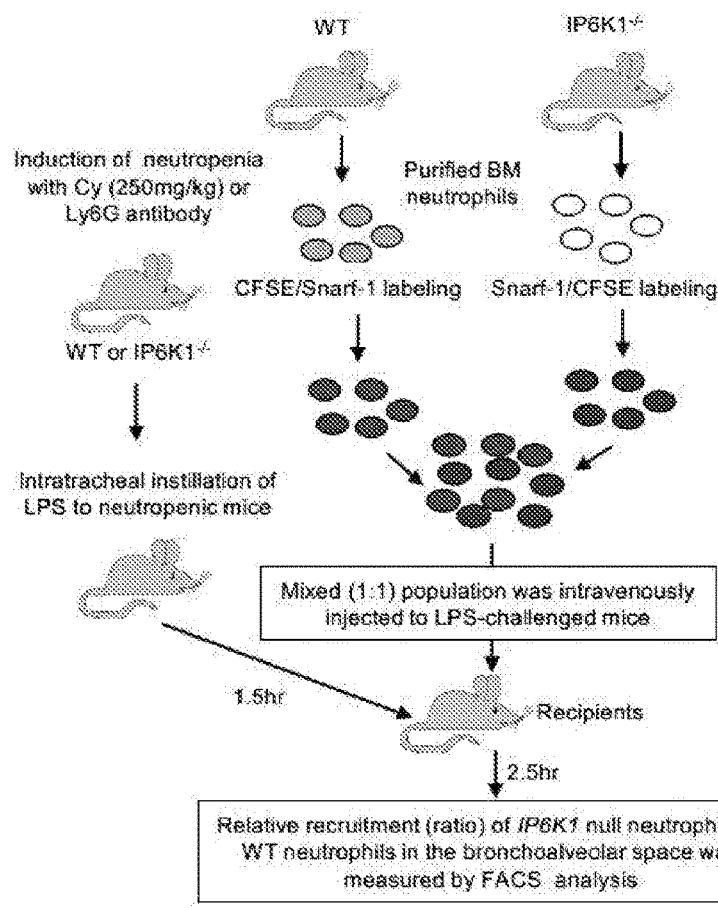

It was next explored whether the reduced neutrophil accumulation in IP6K1-deficient mice is due to IP6K1 disruption in neutrophils. In IP6K1-deficient mice, IP6K1 expression is ablated in all cell types including endothelial cells, lymphocytes, platelets, and macrophages. Therefore, IP6K1 disruption may alter the overall inflammatory environment in the lungs to affect neutrophil function and accumulation indirectly. To circumvent this problem, an adoptive transfer assay was used to explore neutrophil trafficking and accumulation directly (FIG. 2J). Purified Ip6k1-null neutrophils were labeled with green fluorescent dye 5- (and 6-) carboxyfluorescein diacetate succinimidyl esters (CFSE) and WT neutrophils were labeled with a red fluorescent dye 5- (and 6-) chloromethyl SNARF-1 acetate or vice versa.

Figure 2K:
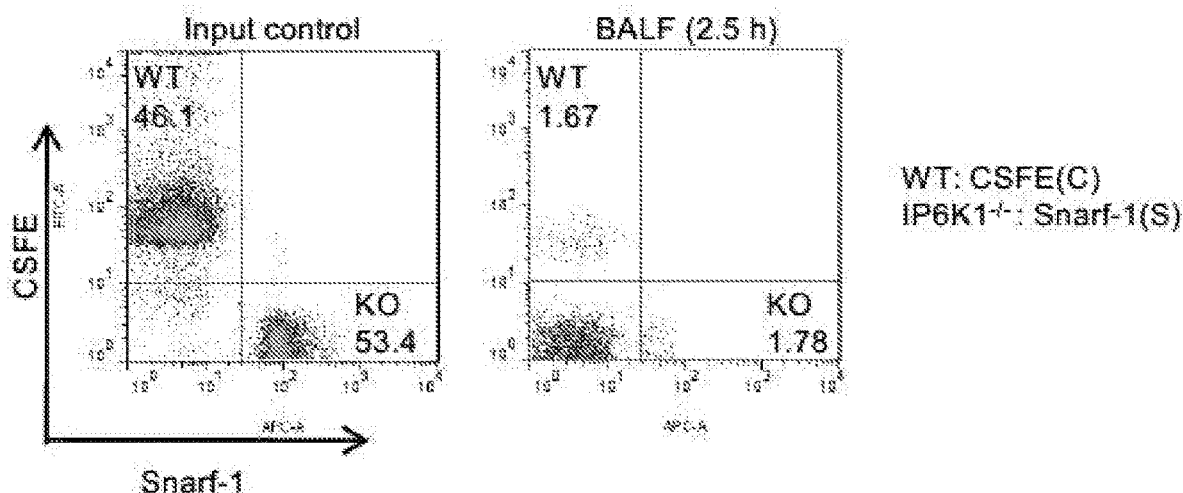

To increase the relative frequency of adoptively transferred neutrophils and improve detection sensitivity, numbers of endogenous neutrophils were reduced by treating recipients with cyclophosphamide, a chemotherapeutic drug, or a Ly6G antibody before challenging recipients with LPS (12). In this setup, the WT and KO neutrophils were isolated and prepared using an identical procedure before being mixed and studied in parallel such that accumulation of WT and KO neutrophils would occur under exactly the same conditions. The relative accumulation of neutrophils was calculated as the ratio of CFSE+ to Snarf-1+ cells in the BALF normalized to the ratio of these two populations in the peripheral blood. IP6K1 disruption did not alter neutrophil half-life in the peripheral blood, as shown by the CFSE+ to Snarf-1+ cell ratio being similar to the input control (1:1). This ratio was also unaltered in the BALF, indicating that these two populations were similarly recruited to the lungs (FIGS. 2K-2L). Adoptively transferred neutrophil accumulation in the inflamed lungs after LPS installation was also independent of the neutrophil staining method (FIG. 2L). Therefore, the reduced neutrophil accumulation observed in the IP6K1-deficient mice was not simply due to an intrinsic migration defect elicited by IP6K1 disruption in neutrophils. The experiments were conducted in both WT and IP6K1 KO recipient mice and essentially the same results were observed (FIG. 2L).

IP6K1 in platelets is essential for efficient neutrophil-platelet aggregation. IP6K1 critically regulates mammalian hemostasis by controlling inorganic polyphosphate (polyP) production in platelets: IP6K1-deficient platelets produced less polyP, slowing platelet aggregation and impairing platelet-mediated plasma clotting (13). Since reduced neutrophil accumulation in IP6K1-deficient mice was not caused by IP6K1 disruption in neutrophils, it was hypothesized that IP6K1 regulates neutrophil accumulation in the inflamed lungs indirectly by controlling platelet function.

Figures 3C, 3D:
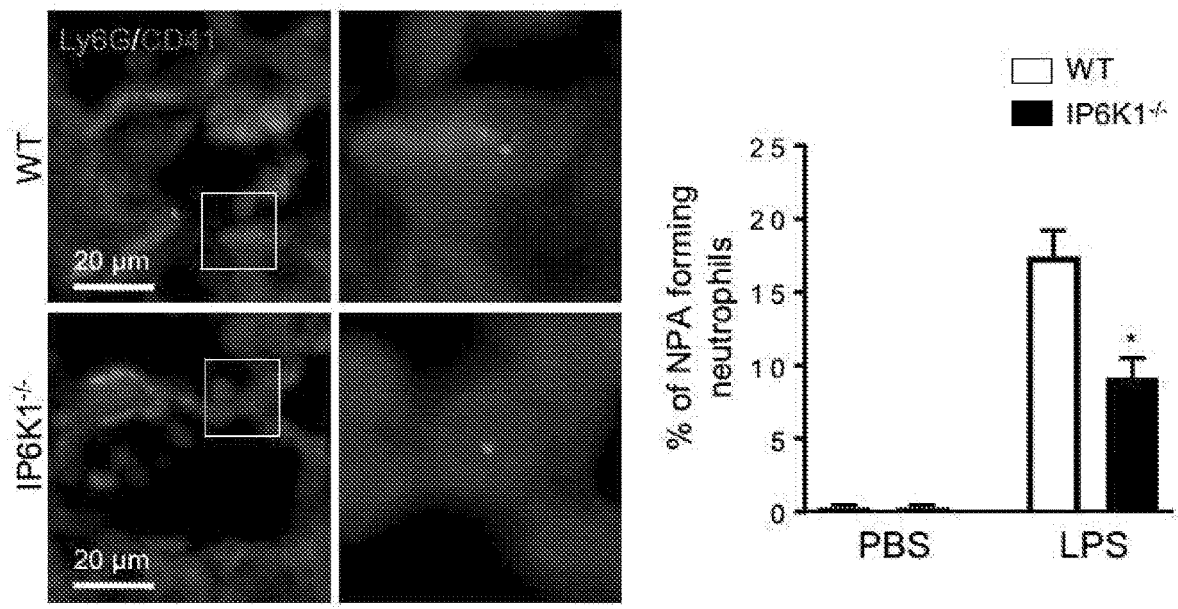
Figure 3E:
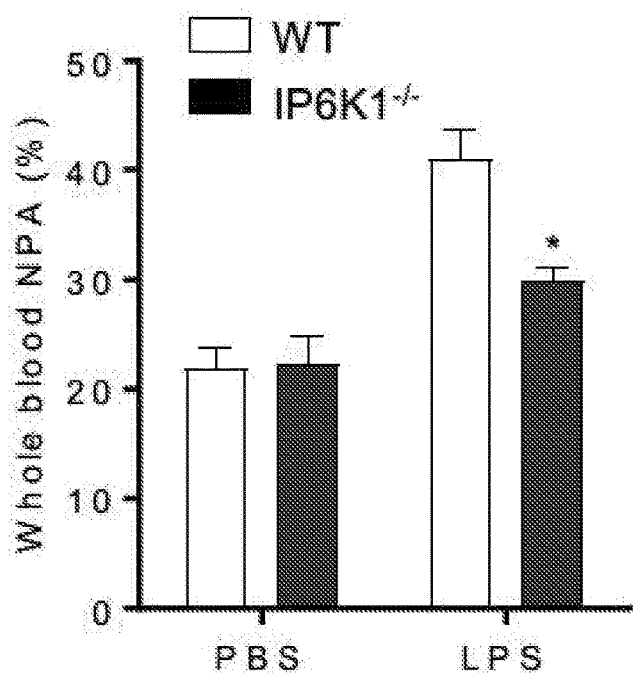
Figure 11A:
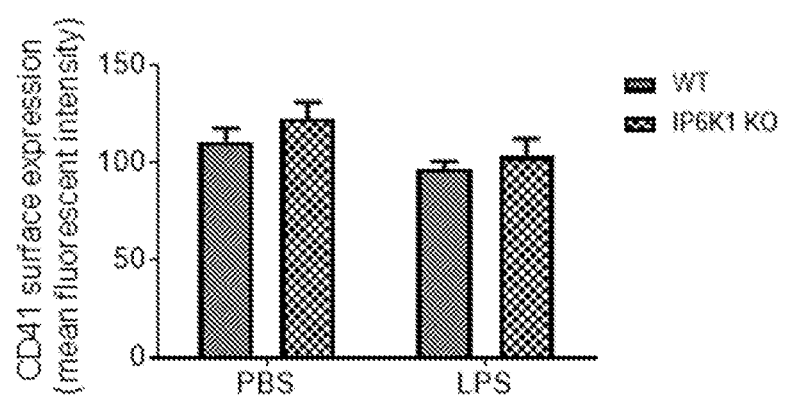
FIGS. 11A-11B demonstrate that InsP6K1-deficient platelets expressed the same amount of platelet markers CD41 and CD61. Mice were intratracheally instilled with 5 mg/kg LPS (*E. coli* 0111:B4) and euthanized at 24 hr after LPS instillation. Surface expression of CD41 (FIG. 11A) and CD61 (FIG. 11B) on the peripheral blood platelets was analyzed using FACS. Data shown are means±SEM of four experiments.
Figure 11B:
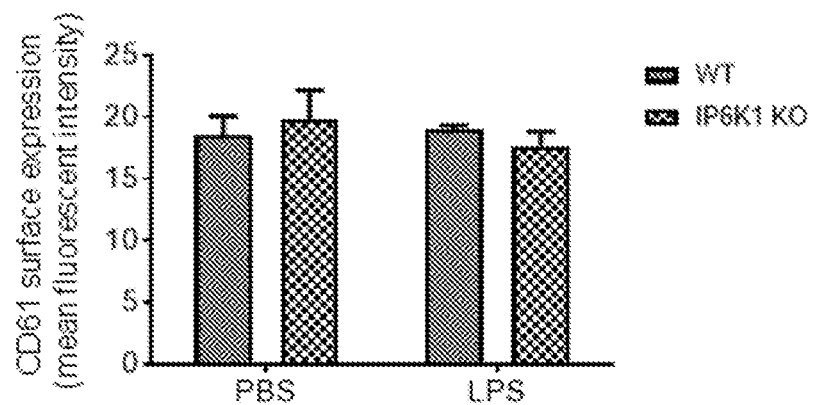

During lung inflammation, both neutrophils and platelets are sequestered in the pulmonary vasculature. Disruption of IP6K1 not only reduced neutrophil but also platelet accumulation in the lungs in LPS-induced lung inflammation (FIGS. 3A-3B). The reduced number of CD41+ platelets was not caused by a decrease in surface expression of CD41, since Ip6k1-null platelets expressed the same amount of the platelet markers CD41 and CD61 (FIG. 11A-11B). Neutrophil-platelet aggregates (NPAs) were quantified in lung sections stained with Gr1 and CD41 antibodies. LPS-induced NPA formation was substantially lower in IP6K1-deficient mice compared to WT (FIGS. 3C-3D). Neutrophil-platelet aggregates were quantified in the peripheral blood in live animals. The percentage of NPA in the blood of LPS-challenged mice increased compared to that in untreated mice, but such increase was attenuated in the IP6K1 deficient mice (FIG. 3E).

Figure 12:
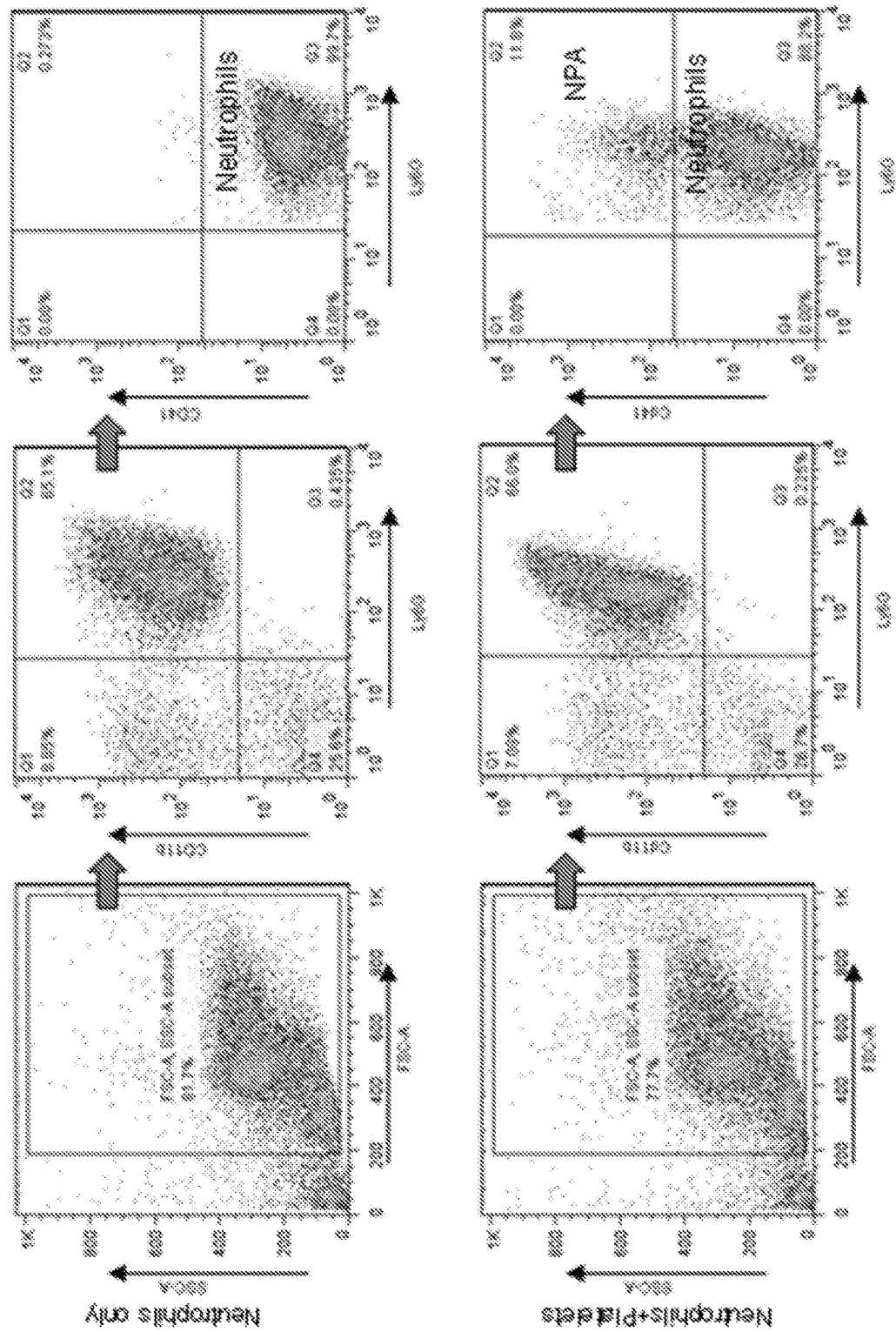
FIG. 12 demonstrates flow cytometry analysis of ex vivo NPA formation. Neutrophils and platelets were isolated from WT mice. Neutrophils were incubated with LPS (5 μg/mL or 1 μg/mL) for 2 h at 37° C. in the presence or absence of platelets. After incubation, cells were stained with CD11b, CD41, and Ly6G and analyzed by flow cytometry to detect NPA. NPAs were CD41 and Ly6G double-positive on FACS.
Figures 13A, 13B:
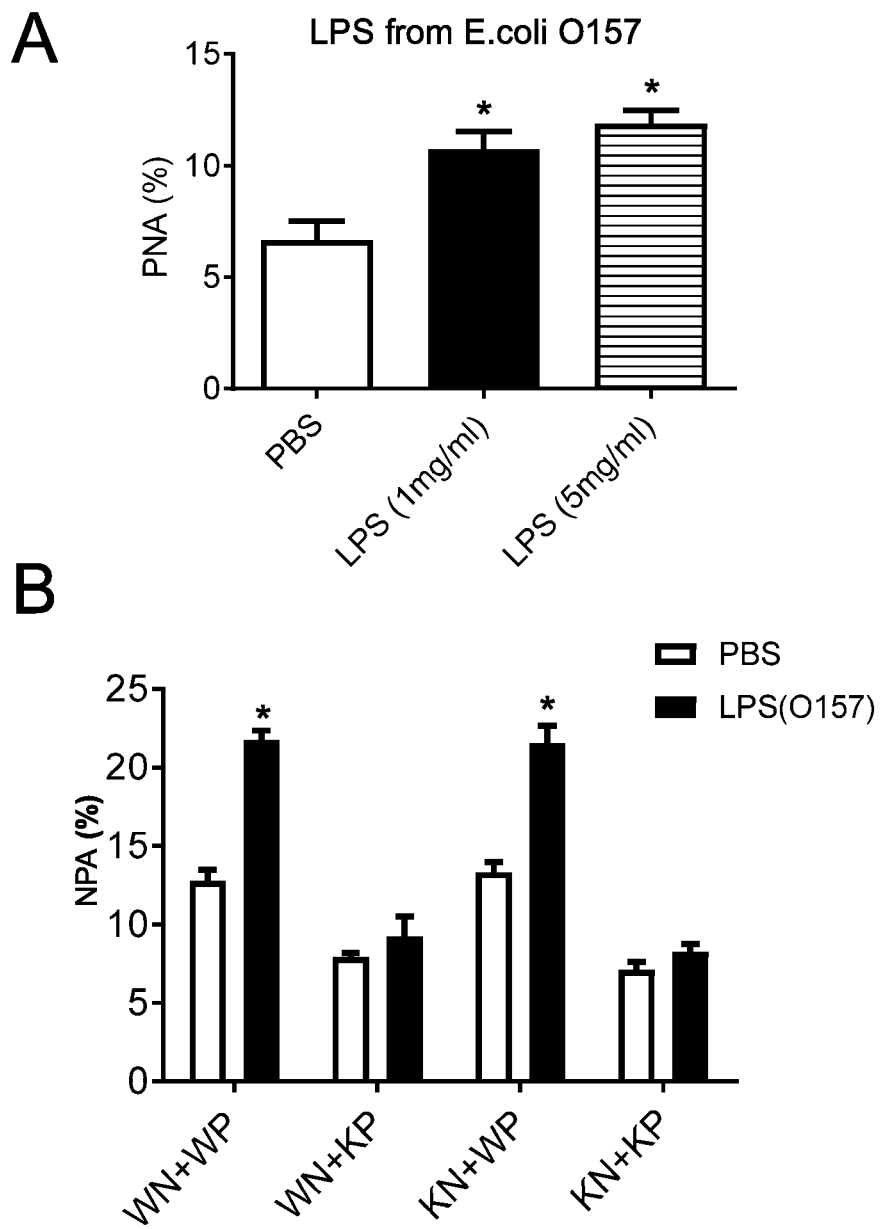
FIGS. 13A-13B demonstrate NPA formation triggered by LPS from *E. coli* O157:H7.

To directly assess the role of IP6K1 in NPA formation, an ex vivo system was utilized in which purified neutrophils and purified platelets underwent heterotypic aggregation in the presence of serum components prior to detection by FACS (FIG. 3F and FIG. 12). Consistent with the in vivo data, LPS treatment increased NPA formation by nearly 100% (FIG. 3G). However, LPS-induced NPA formation did not occur between IP6K1-deficient neutrophils and IP6K1-deficient platelets, regardless of the LPS used (LPS from E. coli 0111:B4 or LPS from E. coli O157:H7) (FIG. 13).

Figure 3I:
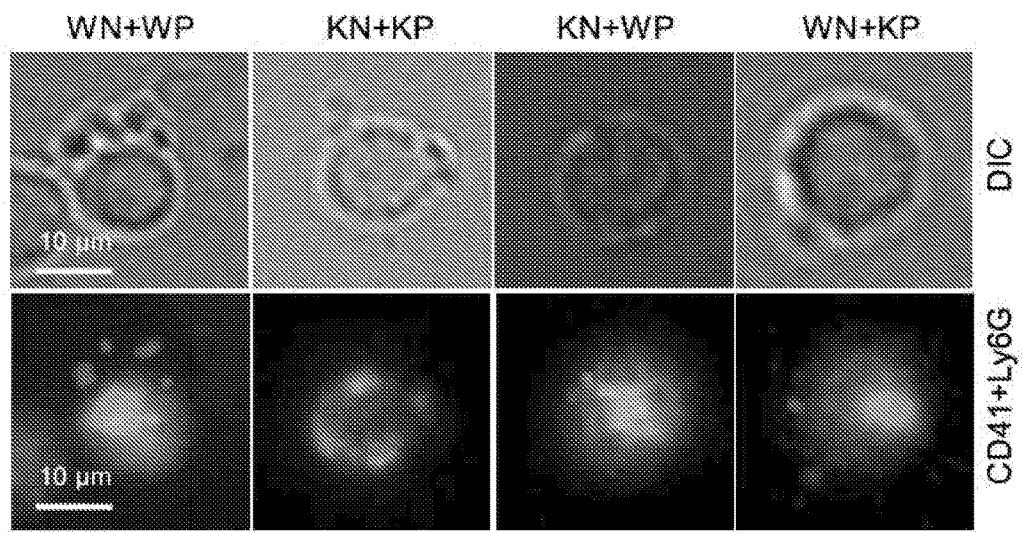
Figure 3J:
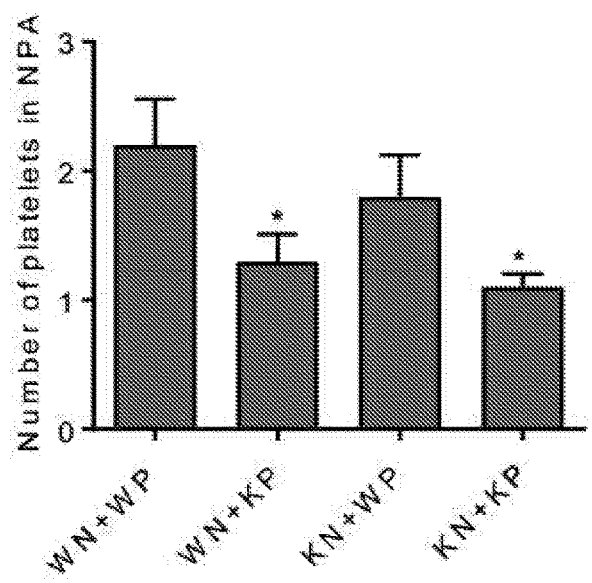
Figures 14A, 14B:
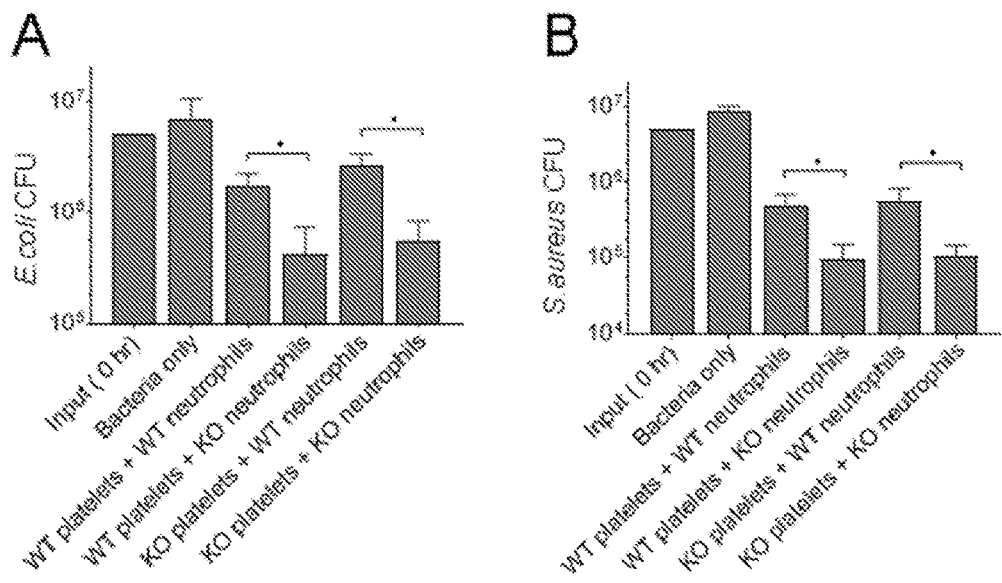
FIGS. 14A-14B demonstrate in vitro killing of bacteria by neutrophil-platelet co-culture. Purified WT or Ip6k1-KO neutrophils ($1\times10^6$) and WT or Ip6k1-KO platelets ($2\times10^8$) were incubated with (FIG. 14A) *E. coli* or (FIG. 14B) *S. aureus* for 1 hr. Diluted aliquots were spread on agar plates and incubated overnight at 37° C. In vitro bacterial killing capabilities were reflected by the decrease of bacteria colony forming units (CFU) after the incubation. Data shown are means±SD (n=5 mice per group). *$p<0.05$.

LPS-induced NPAs were completely abolished when WT neutrophils and Ip6k1-null platelets were incubated together but could still be formed when Ip6k1-null neutrophils and WT platelets were used (FIG. 3H). LPS-elicited NPA formation appeared to be specific; MIP2, a common proinflammatory cytokine, failed to induce the same NPA formation (FIG. 3I). Next assessed was the number of platelets in each LPS-induced NPA by immunostaining and it was found that the number of platelets was reduced when platelet IP6K1 was disrupted (FIGS. 3I-3J). Collectively, these findings demonstrate that platelet IP6K1 expression was essential for LPS-induced NPA formation in the inflamed lungs, indicating that reduced neutrophil presence in the lungs observed in IP6K1-deficient mice may be due to IP6K1 disruption in platelets rather than neutrophils. (1). The bactericidal activity of neutrophil-platelet co-cultures was also assessed. Disruption of IP6K1 in neutrophils, but not platelets, substantially diminished the bacterial killing capability (FIGS. 14A-14B), indicating that the elevated bactericidal activity in the IP6K1-deficient mice may be mediated by neutrophils.

Figure 4A:
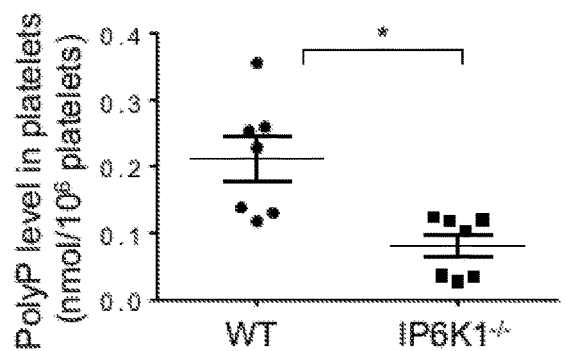
Figure 4B:
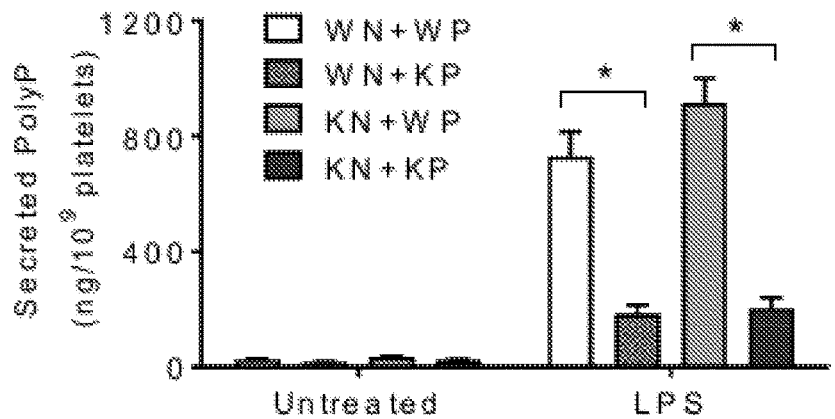
Figure 4C:
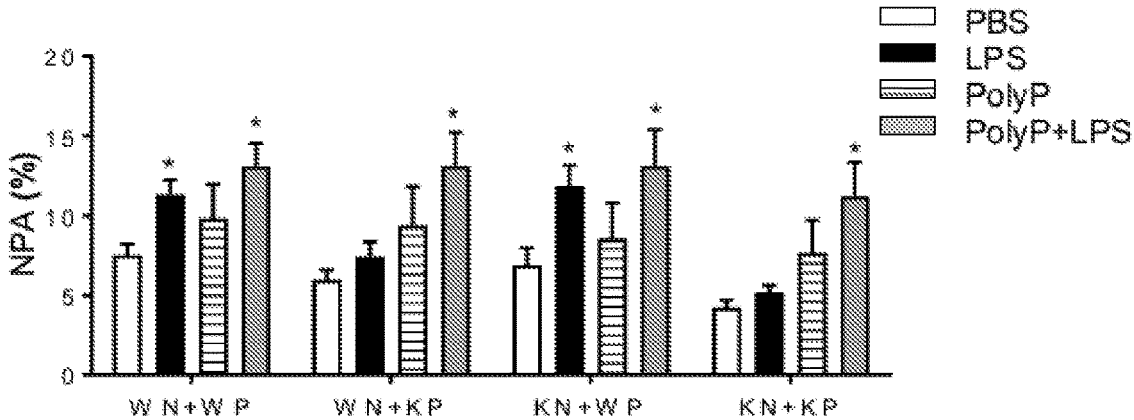
Figure 4D:
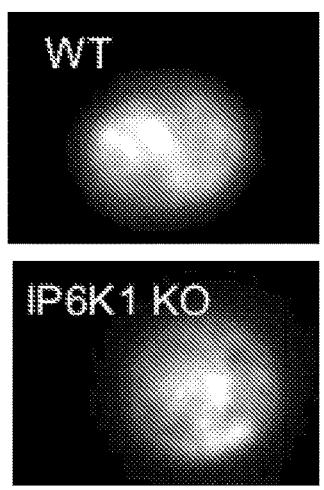

IP6K1-mediated polyP production by platelets plays a critical role in LPS-induced formation of NPAs. Upon stimulation, activated platelets release polyP into the extracellular space to regulate mammalian hemostasis (14-16). IP6K1 could control platelet polyP production and polyP levels were reduced in IP6K1-deficient platelets (FIG. 4A). LPS stimulation also augmented the level of secreted extracellular polyP in platelet-neutrophil co-culture. Importantly, IP6K1 disruption in platelets, but not neutrophils, substantially suppressed LPS-induced polyP secretion (FIG. 4B). Accordingly, it was hypothesized that the defective NPA formation observed in Ip6k1-null mice was due to impaired platelet polyP production. Confirming this hypothesis, the defective NPA formation between IP6K1-deficient platelets and WT or IP6K1-deficient neutrophils was rescued by the addition of polyP in the in vitro NPA-forming assay (FIG. 4C). The defective LPS-induced NPA formation was, therefore, likely to be mainly caused by reduced polyP levels in a system in which the majority of polyP was produced by platelets. Of note, polyP-mediated NPA formation still relied on LPS stimulation; polyP alone did not elicit NPA formation, indicating that other LPS-induced signals were also required for efficient NPA formation. Furthermore, IP6K1 disruption only affected the amount of polyP produced by platelets with the granular localization of polyP remaining unaltered (FIG. 4D).

Figure 4E:
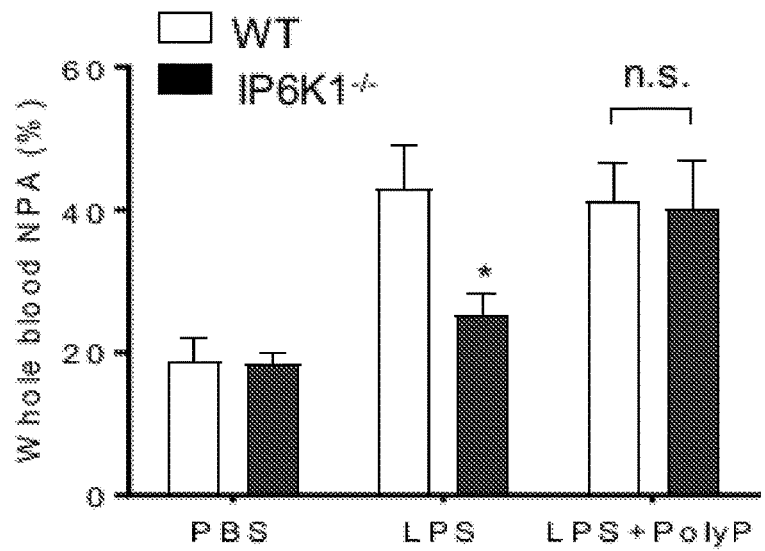
Figures 15A, 15B:
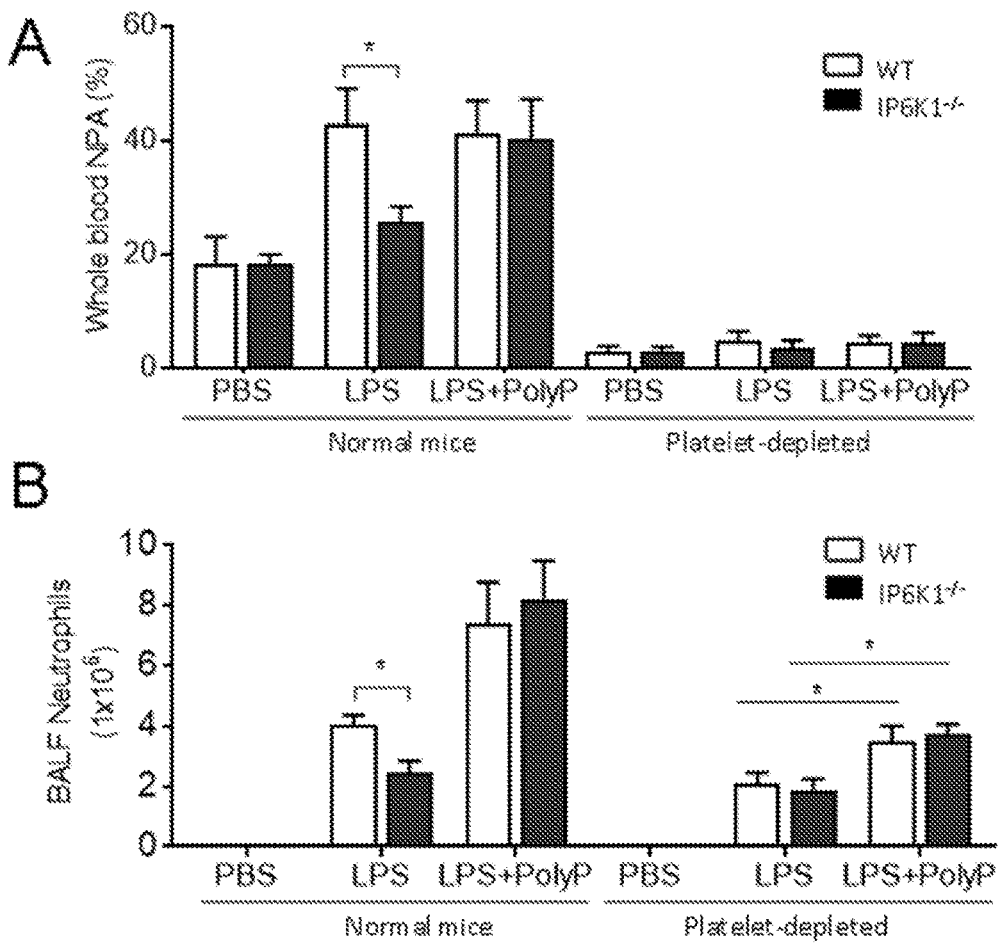
FIGS. 15A-15B demonstrate that polyP can also enhance neutrophil accumulation via a NPA-independent mechanism.
Figures 16A, 16B, 16C:
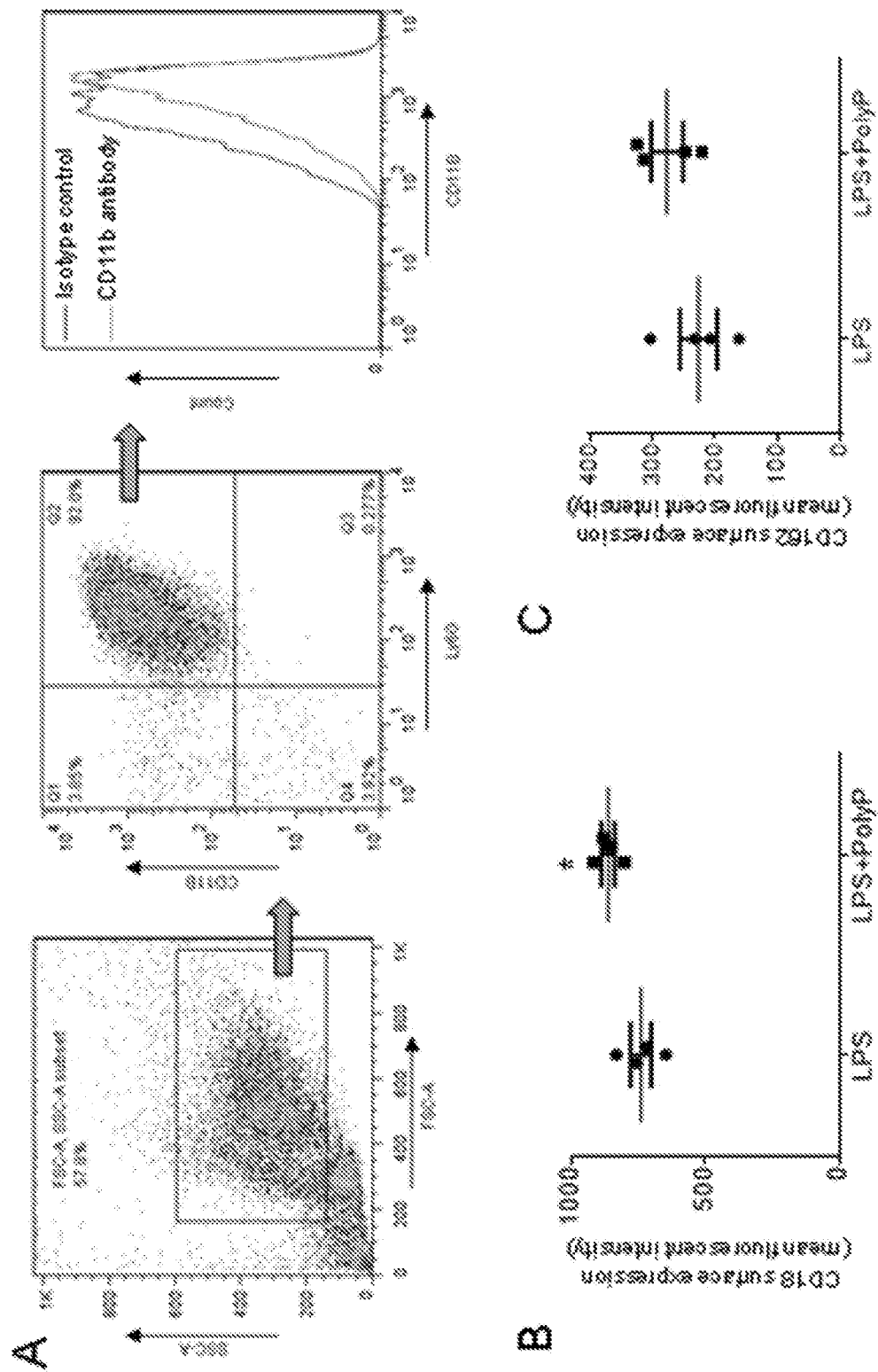
FIGS. 16A-16C demonstrate surface expression of adhesion molecules on neutrophils.

Consistent with the in vitro results, injection of polyP into IP6K1-deficient mice restored LPS-induced NPA formation in the peripheral blood (FIG. 4E) and pulmonary neutrophil accumulation (FIGS. 4F, 4H-4I) to the same levels as WT mice. PolyP treatment also increased pulmonary vascular permeability and neutrophil accumulation in Ip6k1-KO mice. The difference between the WT and KO mice was diminished when polyP was applied (FIGS. 4F-4I). Consistent with this, polyP-treated IP6K1-deficient mice displayed the same amount of LPS-induced lung damage as polyP-treated WT mice (FIGS. 4J-4K). Therefore, IP6K1-mediated polyP production by platelets appears to play a critical role in LPS-induced NPA formation. Reduced polyP production contributed to the decreased neutrophil accumulation and alleviated the lung damage observed in IP6K1-deficient mice. Noticeably, PolyP treatment could still enhance neutrophil accumulation in the absence of NPA, indicating existence of a NPA-independent mechanism (FIG. 15).

Figure 5D:
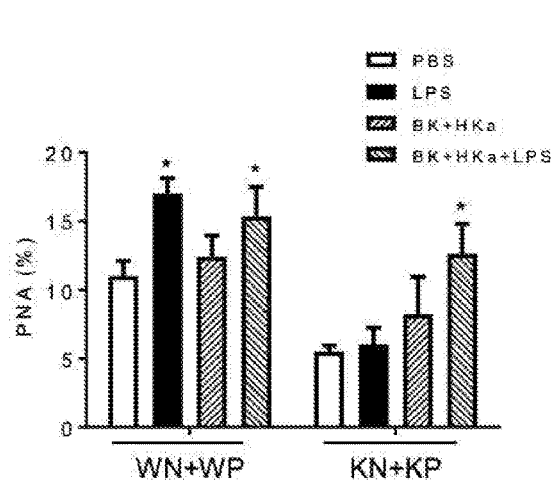

PolyP regulates bradykinin pathway and bradykinin-mediated neutrophil activation. Next explored was the mechanism by which polyP regulates NPA formation. It has previously been shown that platelet-derived polyP can trigger the plasma protease factor XII-dependent contact activation system to drive inflammatory reactions (14, 15, 17). PolyP directly binds to and activates factor XII, leading to proteolysis of high molecular weight kininogen (HMWK) by kallikrein and the release of the inflammatory mediator bradykinin and cleaved HMWK (HKa) (FIG. 5A). Both HKa and bradykinin were required for LPS-induced NPA formation. Neither bradykinin (FIG. 5B) nor HKa alone (FIG. 5C) rescued the defective NPA formation elicited by IP6K1 disruption in platelets. When both bradykinin and HKa were applied exogenously, the LPS-induced NPA between IP6K1-deficient platelets and WT or IP6K1-deficient neutrophils was restored (FIG. 5D).

Figure 5E:
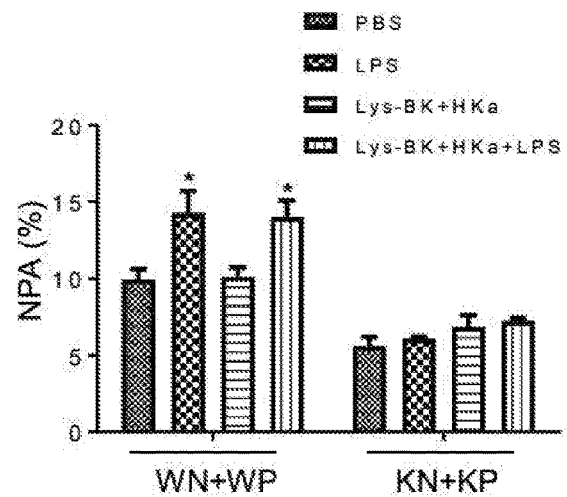
Figure 5F:
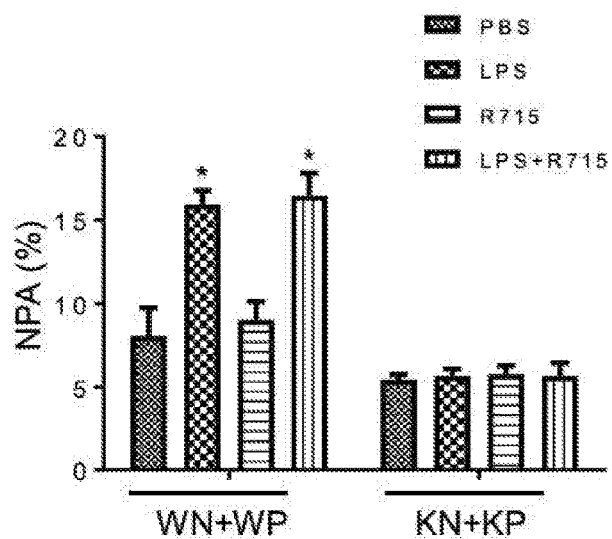
Figure 5G:
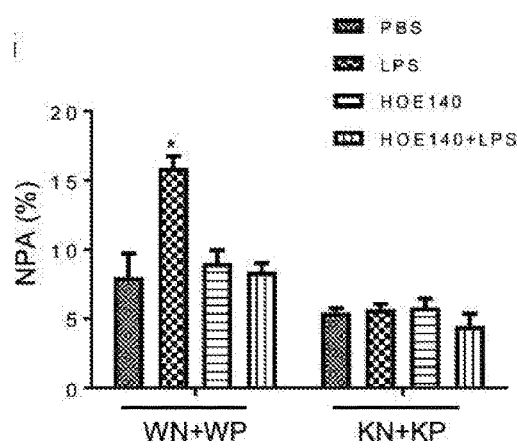
Figure 5H:
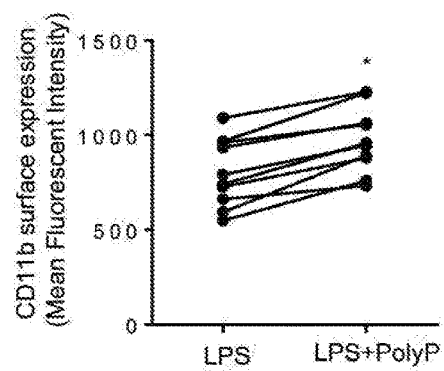

Bradykinin exerts its function via G-protein coupled bradykinin receptors. There are two bradykinin receptors, B1 and B2; bradykinin is the major B2 receptor agonist while the B1 receptor is mainly activated by des-Arg9-BK (DABK), a bradykinin metabolite. B1 receptor expression is known to be upregulated under inflammatory conditions and to mediate neutrophil migration elicited by cytokines such as IL-1β (18, 19). However, treatment of a neutrophil-platelet mixture with HKa and the B1 receptor-specific agonist LYS-BK could not restore NPA formation between IP6K1-deficient platelets and neutrophils (FIG. 5E), suggesting that the B1 receptor may not be critical to LPS-induced NPA formation. To definitively determine the receptor type mediating NPA formation, neutrophil-platelet mixtures were treated with specific B1 and B2 receptor antagonists. HOE140, a B2 receptor antagonist, inhibited LPS-induced NPA formation (FIG. 5F), while R715, a B1 receptor antagonist, failed to do so (FIG. 5G), confirming that bradykinin's effect on NPA formation was mediated via B2 receptors. As a well-known proinflammatory factor and neutrophil activator, bradykinin specifically increases surface expression of the CD11b and CD18 adhesion molecules on neutrophils (20). The same effect was also detected in polyP-stimulated neutrophil and platelet cell mixtures (FIG. 5H and FIGS. 16A-16C). HKa can also promote platelet-neutrophil interactions by bridging CD11b on neutrophils and its receptor glycoprotein Ib (GPIb) on platelets (21), thus providing a potential mechanism for LPS-induced and polyP-mediated NPA formation.

Figure 17A:
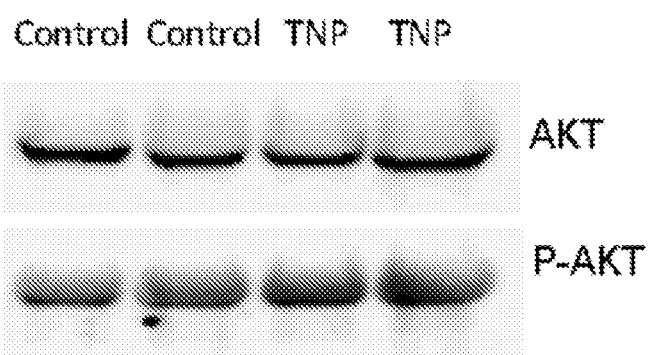
FIGS. 17A-17B demonstrate that the level of PtdIns(3,4,5)P3 signaling, assessed by phospho-Akt, is elevated in TNP treated mice. Mice were treated with TNP for 10 days (20 mg/kg body weight, once a day). Bone marrow neutrophils were isolated and lysed. Total/phosphorylated Akt in cell lysates was detected by western blotting. Relative amounts of phosphorylated Akt were quantified with NIH ImageJ™ software. Data shown are means±SEM of four experiments. *$p<0.05$ vs. neutrophils isolated from mice treated with DMSO alone
Figure 17B:
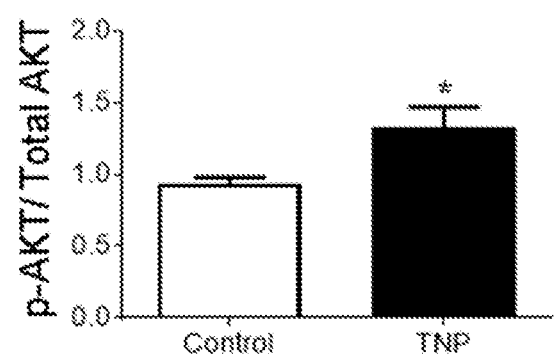

Treatment with the IP6K1 inhibitor TNP alleviates pulmonary inflammation and bacterial pneumonia-associated lung damage. IP6K1 facilitates NPA formation by maintaining high polyP levels in platelets, thereby providing a mechanism to control neutrophil accumulation during lung infection and inflammation. It also indicates that IP6K1 is a therapeutic target in infection and inflammation-induced lung injury, as shown by the Ip6k1-KO mouse model. Thus, it was next investigated whether a specific IP6K1 inhibitor TNP (N2-(m-(trifluoromethyl)benzyl) N6-(p-nitrobenzyl) purine) (22) could also alleviate lung damage in a mouse bacterial pneumonia model. It was found that both mouse and human neutrophils treated with TNP showed substantially enhanced PtdIns(3,4,5)P3 signaling and elevated PtdIns(3,4,5)P3-mediated cellular functions (FIG. 17).

Figure 6A:
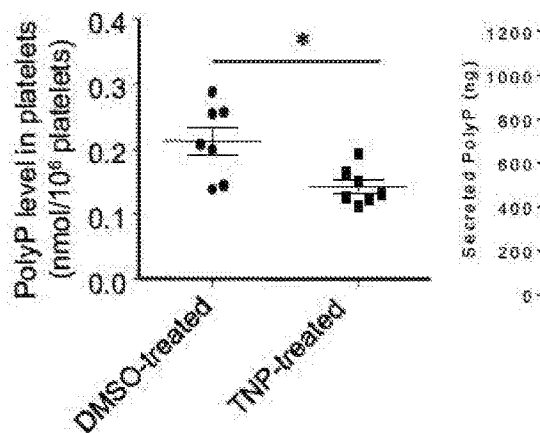
FIGS. 6A-6M demonstrate that treatment with IP6K1 inhibitor TNP alleviates pulmonary inflammation and lung damage associated with bacteria pneumonia.
Figure 6B:
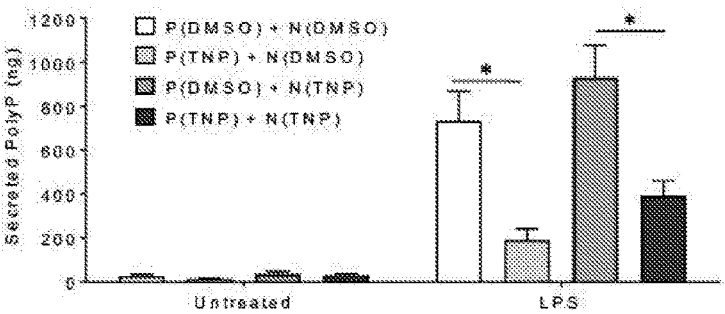
Figure 6C:
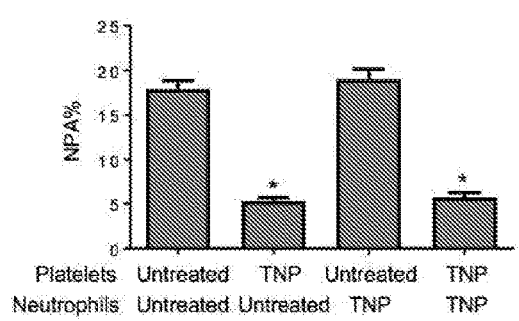
Figure 6D:
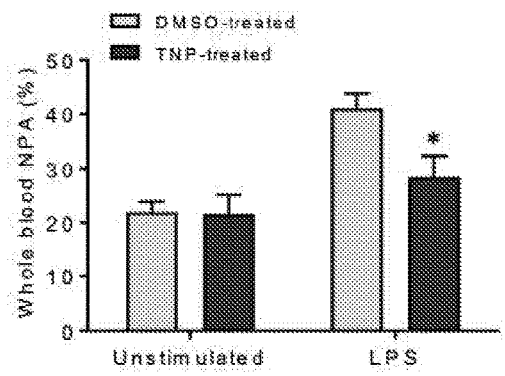
Figure 6E:
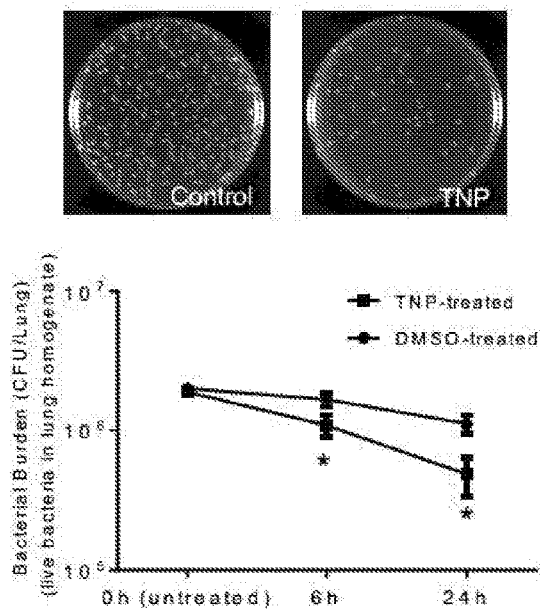
Figure 6F:
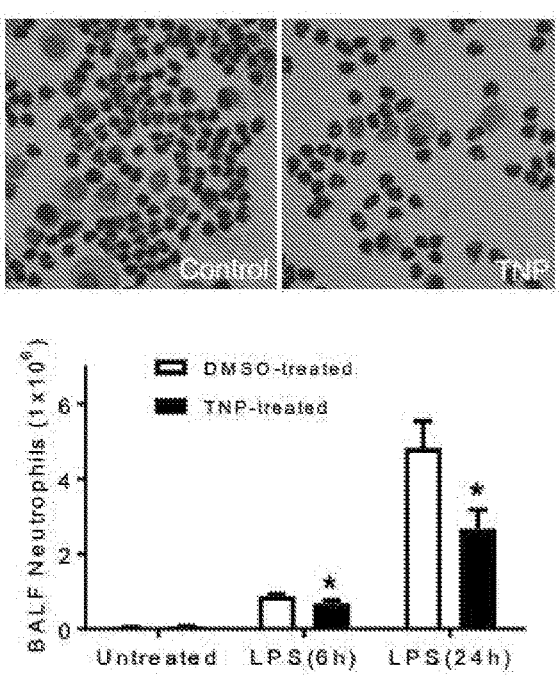
Figure 6G:
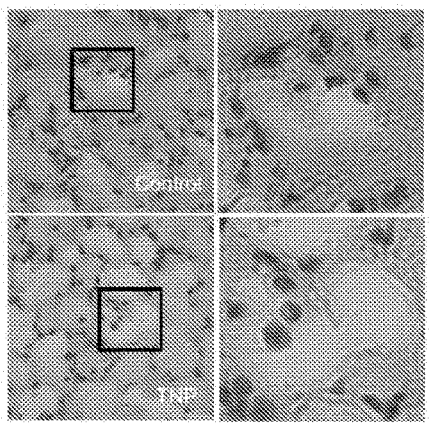
Figure 6H:
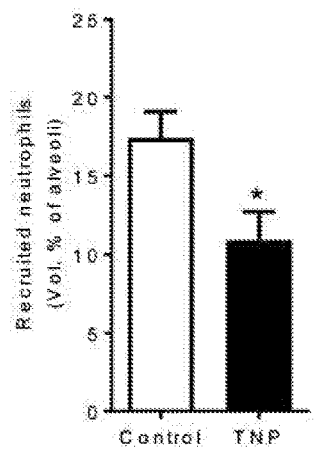
Figure 6I:
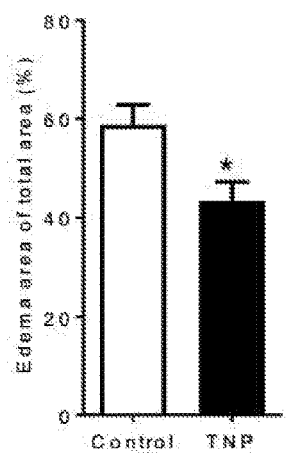
Figure 6J:
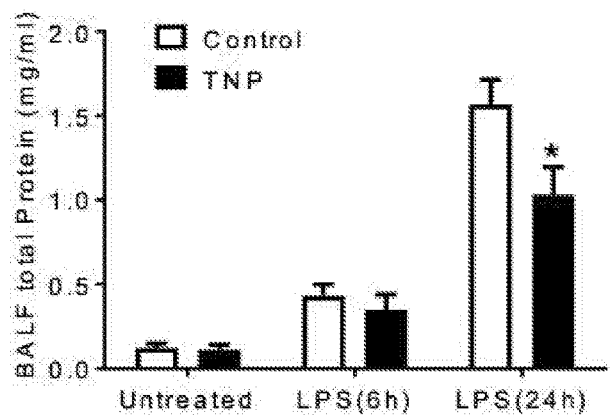
Figure 6K:
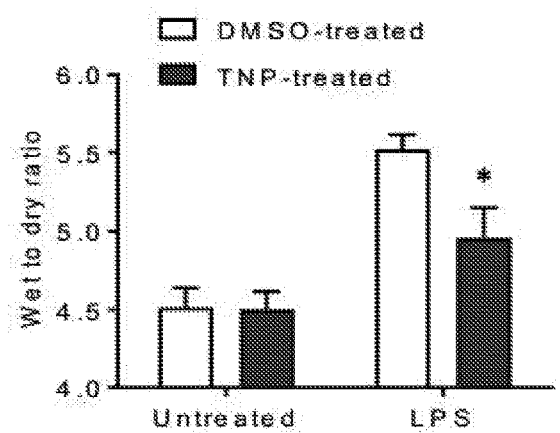

TNP treatment efficiently reduced polyP production in platelets, with platelets isolated from TNP-treated mice displaying reduced intracellular polyP levels and LPS-elicited polyP secretion compared to those isolated from DMSO-treated controls (FIGS. 6A-6B). As a result, LPS-induced ex vivo NPA formation and infection-induced NPA formation in the lungs of live mice were inhibited by TNP treatment (FIGS. 6C-6D). Consistent with the results observed in IP6K1-deficient mice, TNP-treated mice exhibited much improved bactericidal activity (FIG. 6E), and neutrophil accumulation in the inflamed lungs was suppressed as assessed by both BALF neutrophil counts (FIG. 6F) and morphometric analysis of lung sections (FIGS. 6G-6H). Consequently, TNP treatment alleviated inflammation-induced lung damage: there was less edema formation (FIG. 6I) and the total BALF protein levels were decreased (FIG. 6J) in TNP-treated mice compared to those treated with PBS alone. Finally, the measurement of lung wet-to-dry ratio directly confirmed a reduction in pulmonary vascular permeability in TNP-treated mice (FIG. 6K). Thus, inhibiting IP6K1 with TNP efficiently and effectively reduced neutrophil accumulation and alleviated lung injury.

Figure 6L:
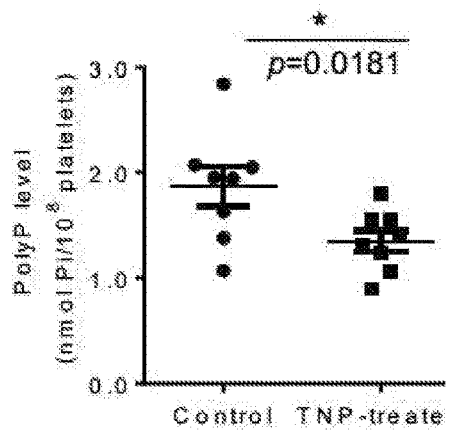
Figure 6M:
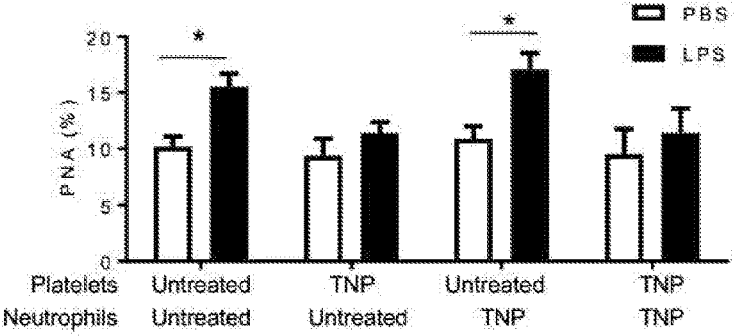

To examine whether inhibition of IP6 kinase can alter LPS-induced NPA formation between human primary neutrophils and platelets, we treated human platelets and/or neutrophils with the IP6K selective inhibitor TNP. Consistent with the results observed in mice, human platelets treated with TNP exhibited reduced polyP levels (FIG. 6L). Consequently, LPS-induced NPA formation was suppressed between human primary neutrophils and platelets treated with TNP. This effect was mainly mediated by IP6K inhibition in platelets, since NPA formation between TNP-treated neutrophils and untreated platelets was unaltered (FIG. 6M). These results indicate that IP6K also plays a role in regulating NPA formation between human neutrophils and platelets.

Discussion

By producing IP7, IP6K1 negatively regulates PtdIns(3,4,5)P3 signaling. Thus IP6K1 disruption in mouse neutrophils elevates PtdIns(3,4,5)P3 signaling and enhances various PtdIns(3,4,5)P3-mediated neutrophil functions such as phagocytosis and ROS production (1). Since upregulated PtdIns(3,4,5)P3 signaling also augments neutrophil accumulation (23, 24), the fact that IP6K1 disruption suppressed neutrophil migration to inflamed lungs in the pneumonia model is somewhat surprising. It is demonstrated herein that this effect is mediated by a platelet-mediated, but PtdIns(3,4,5)P3 signaling-independent mechanism. Numerous studies showed that platelets have the capacity to promote neutrophil accumulation (8-11). Neutrophil accumulation in inflamed lungs is controlled by a unique mechanism that critically involves platelets (25). Neutrophil-platelet aggregate (NPA) formation promotes neutrophil accumulation in the alveolar spaces during acute lung inflammation. In addition, endovascular NPAs may directly damage the pulmonary capillary endothelium, exaggerating lung injury. In a mouse transfusion-related acute lung injury (TRALI) model (2) and a mouse LPS (3) or acid-induced acute respiratory distress syndrome (ARDS) (4, 5) model, both neutrophils and platelets sequester in the pulmonary vasculature. Platelet depletion or treatments that disrupt NPAs can substantially reduce inflammation-induced lung damage (2-6). IP6K1 is a novel regulator of mammalian hemostasis via the control of inorganic polyphosphate (polyP) production by platelets. IP6K1-deficient mice have reduced platelet polyP levels, slower platelet aggregation, and impaired platelet-mediated plasma clotting (13). It is demonstrated herein that the defective neutrophil accumulation in the lungs in IP6K1-deficient mice is mainly caused by IP6K1 disruption in platelets but not neutrophils.

IP6K1 disruption leads to reduced neutrophil accumulation in the lungs in bacterial pneumonia. One obvious explanation for reduced neutrophil accumulation is that the augmented neutrophil killing and resulting bacterial clearance accelerates the resolution of pulmonary inflammation, in turn causing less neutrophil accumulation. However, the levels of proinflammatory cytokines in the inflamed lungs are unaltered in the IP6K1-deficient mice. In addition, disruption of IP6K1 does not alter neutrophil apoptosis during lung inflammation, thus the reduced neutrophil accumulation is not due to accelerated death. An adoptive transfer assay was conducted to explore neutrophil trafficking and accumulation directly. Adoptively transferred WT and IP6K1-deficient neutrophils were recruited to the inflamed lung at a similar rate, suggesting that the reduced neutrophil accumulation observed in the IP6K1-deficient mice was not simply due to an intrinsic migration defect elicited by IP6K1 disruption in neutrophils. As previously reported, platelet depletion could reduce LPS-induced lung damage. Intriguingly, the reduced neutrophil accumulation and lung injury observed in the IP6K1-deficient mice was diminished in platelet-depleted mice, indicating that platelets contributed to IP6K1 function in LPS-elicited pulmonary inflammation and injury. The reduced neutrophil accumulation in IP6K1-deficient mice is likely due to decreased polyP production by IP6K1-deficient platelets, since this defect can be rescued by polyP-treatment. Consistent with this, polyP-treated IP6K1-deficient mice displayed the same amount of LPS-induced lung damage as polyP-treated WT mice. Therefore, IP6K1-mediated polyP production by platelets appears to play a critical role in lung inflammation. We further demonstrate that polyP regulates neutrophil accumulation by triggering the bradykinin pathway and bradykinin-mediated neutrophil activation.

PolyP treatment rescued impaired LPS-induced NPA formation between IP6K1-deficient platelets and neutrophils, suggesting that IP6K1's function in NPA formation is mediated by polyP. Consistently, treatment of IP6K1-deficient mice with polyP restored LPS-induced pulmonary neutrophil accumulation to the same levels as WT mice. However, treatment with polyP was not sufficient for NPA formation; LPS stimulation was required for this IP6K1-mediated process. Thus other LPS-dependent factors are also involved in NPA formation. One mechanism by which polyP regulates NPA formation is through factor XII activation and the subsequent generation of bradykinin and HKa. Here, both HKa and bradykinin were required for LPS-induced NPA formation, with bradykinin specifically increasing surface expression of adhesion molecule Mac-I on neutrophils and HKa presumably promoting NPAs by bridging Mac-1 (CD11b/CD18) on neutrophils to its receptor GPIb on platelets (21). Intriguingly, HKa is also reported to be able to interact with Mac-1 and block Mac-1-dependent leukocyte adhesion to endothelial cells (26, 27).

IP6K1 facilitates NPA formation by maintaining high polyP levels in platelets. It is contemplated herein that the reduced polyP production contributed to the decreased NPA formation, diminished neutrophil accumulation, and alleviated lung damage observed in IP6K1-deficient mice. However, although the concept of NPA has been around for over a decade, there is still no direct evidence showing that neutrophil-platelet aggregates mediate neutrophil accumulation. Some studies show that there is no preferential pulmonary sequestration of NPA in local (28) or systemic (29) inflammation. Herein it is demonstrated that polyP produced by platelets is essential for neutrophil accumulation. polyP regulates neutrophil accumulation by triggering the bradykinin pathway. As a well-known proinflammatory factor and neutrophil activator, bradykinin specifically increases surface expression of the CD11b and CD18 adhesion molecules on neutrophils (20), and thus may enhance neutrophil accumulation independent of NPA. A previous report by Assaduzzaman et al. also showed that platelets play a key role in regulating neutrophil infiltration in the lung via upregulation of Mac-1 (CD11b/CD18) in sepsis induced by cecal ligation and puncture (CLP) (29). In platelet-depleted mice, LPS-induced NPA formation was suppressed with no difference detected between WT and IP6K1-deficient mice. However, PolyP treatment could still enhance neutrophil accumulation in the absence of NPA, indicating existence of a NPA-independent mechanism.

Materials and Methods

Study Design. The research objective of this study was to determine how IP6K1, through polyP production by platelets, regulate neutrophil accumulation in bacterial pneumonia. To achieve this objective, we undertook various approaches, including measurement of BALF neutrophil count, bacterial killing assay, H&E staining, assessment of pulmonary edema formation, to analyze neutrophil accumulation, host defense, and neutrophil-mediated pulmonary damage in bacterial pneumonia. For animal studies, 10-14 week-old mice were used. The effect of IP6K1 disruption or the specific IP6K inhibitor TNP on phenotype was assessed by investigators who were blind for genotype and treatment. To perform reliable statistical analysis, at least three independent experiments were conducted for each data shown in the manuscript, unless differently indicated in the figure legends. These numbers were chosen based on power analyses and previous experience in our lab.

Neutrophil depletion with Ly6G antibody. Neutrophil depletion with Ly6G antibody was carried out as previously described (30). Briefly, WT and IP6K1-deficient mice were intraperitoneally injected with a single dose of anti-mouse Ly6G antibody (clone 1A8, BioLegend, 400 µg/kg). The antibody was administered i.p. to obtain a sustained depletion over the first 48 hours of the experiment. Differential white blood cell count using Wright-Giemsa staining was performed to confirm that the neutrophil depletion was successful (peripheral blood neutrophil count was reduced by >85%) (30).

Platelet depletion in WT and IP6K1-deficient mice. Mice were intravenously injected with a single dose of platelet-depleting antibody (anti-GPIb/CD42b, Emfret Analytics, 2 µg/g bodyweight, diluted in 100 µl sterile PBS). The peripheral blood platelet counts were assessed at indicated time points.

Neutrophil-platelet aggregation. Mouse and human neutrophils were isolated and purified as previously described (31). Whole blood was collected into ACD tubes and platelet-rich plasma was isolated by centrifuging twice at 100×g for 5 min. Neutrophils ($0.5 \times 10^6$) and platelets ($5 \times 10^6$) were incubated for 2 h at 37° C. with LPS in 1 ml Tyrode's buffer (Sigma) supplemented with 1% BSA. After incubation, mouse neutrophils and platelets were stained with CD11b, CD41, and Ly6G and analyzed by flow cytometry to detect NPAs. Human neutrophils and platelets were stained with CD66, CD16, and CD41. NPA % was calculated as the percentage of CD66+, CD16+ and CD41 triple-positive cells (NPAs) among all CD66+ and CD16+ cells.

Statistical analysis. Survival rates were analyzed using the Kaplan-Meier survival curves and log-rank test. Other values were compared using Student's t test. Data were presented as means (±SD). Statistical significance was determined using a two-tailed paired t test for 5H and 6L, and a two-tailed unpaired t test for other comparisons. All calculations were performed using GraphPad Prism™ 6.0 software for Windows (GraphPad Software). Most experiments were repeated at least three times and the data were pooled and analyzed together. Differences were considered significant when the P value was <0.05.

Mice. Ip6k1-knockout (KO) mice were generated by targeted deletion of the Ip6k1 exon 6 coding sequence as previously described (1). Corresponding wild-type (WT) littermates were used as paired controls for Ipk61-KO mice. Mice aged 10-14 weeks were used. Mouse bone marrow neutrophils were prepared as described by Loison et al. (31). The Children's Hospital Animal Care and Use Committee approved and monitored all animal procedures.

Bacteria or LPS-induced acute pneumonia. After anesthesia with ketamine hydrochloride (100 mg/kg intraperitoneally (i.p.)) and xylazine (10 mg/kg i.p.), mouse tracheas were surgically exposed and a total volume of 40 µl of saline, a dose of $2 \times 10^6$ cfu of *E. coli* (strain 19138; American Type Culture Collection), a dose of $5 \times 10^8$ cfu of *Stapyhlococcus aureus* (strain 10390; American Type Culture Collection), or the indicated amount of LPS (LPS from *E. coli* O111:B4 or LPS from *E. coli* O157:H7; Sigma-Aldrich was instilled intratracheally via an angiocatheter inserted through the trachea and into the left bronchus. Colloidal carbon (1%) was included in the instillate to indicate deposition. After surgery and wound closure, mice were suspended by their front legs to help deliver the instillate deep into the left lobe before being placed back into the cage with soft and warm bedding for recovery. Mice were euthanized by CO2 at each time point. For polyP treatment, Medium Chain Polyphosphate (p100) (Kerafast Inc) was injected intraperitoneally (50 µg/g body weight) 10 min after the instillation of LPS. For treatment with IP6K1 inhibitor TNP (N2-(m-(trifluoromethyl)benzyl) N6-(p-nitrobenzyl)purine), mice were injected intraperitoneally with TNP once a day (20 mg/kg body weight) for 10 days before the induction of lung inflammation. TNP (Tocris Bioscience) was dissolved in DMSO/Tween80/water (1/1/8) at a concentration of 2 mg/ml and was injected directly without dilution.

Immunohistochemistry. Freshly deparaffinized and rehydrated sections were permeabilized with 0.1% Tx-100 in PBS and blocked with PBS containing 10% goat serum. Sections were incubated with rabbit anti-mouse CD41 (Abcam) and rat anti-mouse Ly6G antibody (Abcam) at 4° C. overnight followed by 2 h 37° C. incubation with Alexa 555-conjugated goat anti-rabbit IgG secondary antibody (Invitrogen) and Alexa 488-conjugated goat anti-rat IgG secondary antibody (Invitrogen), respectively. Nuclei were labeled by DAPI counterstaining.

Neutrophil accumulation. WT and Ip6k1-KO mice were anesthetized and instilled with bacteria or LPS as described above. After 24 h, mice were euthanized by CO2. The chest cavity was opened and a catheter was tied to the trachea. Bronchoalveolar lavage (BAL) was performed (1 mL PBS/15 mM EDTA×10) in each group. The BAL fluid (BALF) was centrifuged at 450×g for 10 min. The total number of cells in the BALF was counted by hemocytometry. Differential cell counts were conducted on cytospin preparations stained with a modified Wright-Giemsa stain (Volu-Sol, Inc.). Neutrophils were identified by their lobular or segmented nuclei. The percentage of neutrophils in the whole population (% PMN) was determined accordingly. Total numbers of neutrophils (#PMN) recruited was calculated as follows: [#PMN]=[cell density]×volume×[% PMN]. Emigrated neutrophils in the alveolar air spaces were also quantified by morphometric analysis of tissue sections. Emigrated neutrophils in lung sections (5 mice/group) 24 h after infection were quantified using standard point-counting morphometry (7). Briefly, mice were euthanized and their hearts tied off to maintain pulmonary blood volume. Lungs were then excised and fixed by intratracheal instillation of Bouin's solution at a pressure of 23 cm H2O and embedded in paraffin. Five to 6 µm-thick sections were cut and stained with hematoxylin and eosin (H&E). Neutrophils could be easily recognized by their lobular or segmented nuclei under high magnification. A counting grid (10×10, covering 70,000 µm2 of the magnified field) was reflected onto the field of view using a drawing tube. Randomly selected fields of pneumonic peripheral lung largely free of non-capillary blood vessels and bronchioles or larger airways were examined. At least three grids (300 points) were counted for each lung. The relative volumes of the parenchymal regions occupied by emigrated neutrophils were calculated by investigators blinded to the identities of the mice and were expressed as a percentage of the total parenchymal region volume (including both tissue and air spaces).

BALF total protein levels and cytokine/chemokine levels. BALF samples were obtained from mice 24 h after *E. coli* challenge. BAL was performed with 1 ml cold PBS/15 mM EDTA flushed in and out three times. Protein concentrations were measured in BALF using the Bio-Rad protein assay reagent. A standard curve was constructed using BSA. Cytokine levels in BALF were measured with ELISA kits according to the manufacturer's protocol (R&D Systems).

In situ detection of apoptosis. Lung sections were stained using a TACS™ TdT Kit following the manufacturer's protocol (R&D Systems).

Bacterial burden. Lung tissues were washed three times with cold sterile PBS and cut into small pieces. The tissue was then homogenized in sterile PBS on ice using the Tissue-Tearor™ (Model 9853370, BioSpec Products, Inc.). The probe was moved up and down in the tube for 30 s (1 cycle) with 6 homogenization cycles and 1 min incubation on ice between cycles. Lung homogenates were then serially diluted in ice-cold sterile PBS and aliquots were spread on Luria broth (LB) agar plates. After overnight incubation at 37° C., colonies were counted and bacterial viability was expressed as cfu per lung calculated based on the dilution factor.

Mortality induced by bacteria pneumonia. Due to animal welfare concerns and as requested by the Institutional Animal Care and Use Committee (IACUC), we used hypothermia (reduced body temperature) as an indicator of pneumonia-induced mortality in mice. This method can provide an earlier and more humane experimental endpoint. We first determined the fatal hypothermia temperature (FHT, the temperature at which mice will inevitably die) under our experimental condition. We found that when body temperature reached ≤29° C., 100% (n=12) of mice instilled with bacteria died. Thus, in this experiment, mice with a body temperature below 29° C. were counted as dead mice, and were euthanized immediately by asphyxiation due to inhalation of CO2. To compare the body temperature of bacteria challenged wild-type and IP6K1 knockout mice during the course of pneumonia, the mice were checked every 6 hours for 7 days (or until the mice died). Since more frequent monitoring of body temperature was not practically feasible, some mice would die in the 6 hour interval without being detected to be hypothermic.

Cyclophosphamide-induced mouse neutropenia. Cyclophosphamide powder (Cytoxan®, Bristol-Myers Squibb) was dissolved in distilled water for injection at a final concentration of 20 mg/ml. Cyclophosphamide was injected i.p. at a total dose of 250 mg/kg (two 0.5 mL injections on day 1 (150 mg/kg) and day 4 (100 mg/kg)). Blood samples (~30 μL) were taken from the retro-orbital sinuses of anesthetized uninfected mice using heparinized capillary tubes (Modulohm A/S) on days 1, 4, 5, 6, and 7. Total and differential white blood cell counts (neutrophils, lymphocytes, and monocytes) were performed using a Hemavet 850™ hematology system (Drew-Scientific Inc).

In vitro killing of bacteria by neutrophil-platelet co-culture. Fresh overnight culture of *Escherichia coli* (strain 19138; ATCC) and *Staphylococcus aureus* (strain 10390; ATCC) were suspended in PBS at an $OD_{600}$ of 0.20 and opsonized with 10% mouse serum for 1 hr at 37° C. in a water bath. Purified WT or Ip6k1-KO neutrophils (1×106) and WT or Ip6k1-KO platelets (2×108) were incubated with *E. coli* or *S. aureus* (5×106 cfu) for 1 hr. with intermittent shaking. After each time period, cells were lysed by adding distilled H2O and diluted aliquots were spread on LB agar (*E. coli*) or Blood agar (*S. aureus*) plates. The CFU were counted after incubating the plates overnight at 37° C. Bacterial suspension without any cells was used as input control. In vitro bacterial killing capabilities were reflected by the decrease of bacteria colony forming units after the incubation.

Flow cytometry. Murine neutrophils and platelets were incubated as described above. Cells were then harvested, washed with ice-cold PBS, and stained with APC0-CD11b (eBioscience), PE-CY7-Ly6G (BD Bioscience), FITC-CD41 (eBioscience), and isotype controls to detect leukocyte and platelet antigens. Samples were examined with a FACSCanto II™ flow cytometer (Becton Dickinson). Neutrophils were gated by their forward- and side-scatter characteristics and by their Ly-6G+/CD11b+ (neutrophil) expression pattern (30). Platelets were detected by CD41 staining NPAs were Ly-6G+CD41+. All data were analyzed using FlowJo™ software (TreeStar; FlowJo LLC).

Assessment of pulmonary capillary permeability. Evans blue dye (EBD, 40 mL/kg) was injected into mouse tail veins 30 min before termination of the experiment to assess vascular leak. Following euthanasia, lungs were perfused free of blood with Dulbecco's phosphate-buffered saline (DPBS) before being excised en bloc. The lungs were then homogenized in DPBS (1 mL/0.1 mg of tissue), incubated with two volumes of formamide (18 h, 56° C.), and centrifuged at 5,000×g for 30 min. The optical density of the supernatant was determined by spectrophotometry at 620 nm. Extravasated EBD concentration (microgram EBD per lung) in lung homogenates was calculated against a standard curve.

PolyP extraction and determination. PolyP was extracted from platelets using perchloric acid and quantified as the amount of orthophosphate residues (Pi) released upon sample treatment with recombinant exopolyphosphatase (PPX; from yeast *Saccharomyces cerevisiae*) as described by Müller et al. (14). Briefly, platelets were pelleted from platelet-rich plasma (PRP) and subjected to acid extraction (0.5 M perchloric acid for 30 min on ice) and neutralized with 1 M potassium carbonate. The neutralized extract was clarified (900×g, 5 min) and the supernatant was subjected to overnight incubation with or without recombinant *S. cerevisiae* exopolyphosphatase PPX (2 μg) to completely hydrolyse polyP. The released orthophosphate (Pi) was estimated using malachite green reagent (33.75 mg malachite green, 105 mg ammonium molybdate in 100 mL of 1 N hydrochloric acid) at a 1:4 ratio of sample to reagent by incubating the reaction for 10 min at room temperature and reading the absorbance at 650 nm (EnSpire multimode plate reader, PerkinElmer). The Pi contributed by polyP was determined by calculating the difference in Pi content between the PPX digested and undigested platelet extracts from the same sample. To isolate polyP from the supernatant of neutrophil-platelet co-culture, the supernatants were first incubated with proteinase K (750 mg/ml, 37° C., 1 hr) and extracted with a 1:1 phenol/chloroform mixture. The aqueous phase was then chloroform extracted. PolyP was precipitated from the extracts with barium acetate (0.1 M, pH 4.5) and quantified as described above.

Accumulation of adoptively transferred neutrophils at inflammatory sites. Bone marrow-derived neutrophils were labeled with CFSE (final concentration, 504) or Snarf-1 (final concentration, 5 μM) at 37° C. for 10 min and then washed twice with PBS. Labeled cells were mixed (1:1) as indicated and injected intravenously (via the tail vein) into neutropenic mice challenged with LPS for 2.5 h. BALF was harvested 1.5 h after granulocyte transfusion. The number of adoptively transferred neutrophils recruited to the lung was analyzed using a FACSCanto II™ flow cytometer and FACSDiva™ software (BD Biosciences). Relative accumulation of WT and Ip6k1-KO neutrophils was calculated as the ratio of indicated populations in the lung.

REFERENCES AND NOTES

1. A. Prasad, Y. Jia, A. Chakraborty, Y. Li, S. K. Jain, J. Zhong, S. G. Roy, F. Loison, S. Mondal, J. Sakai, C. Blanchard, S. H. Snyder, H. R. Luo, Inositol hexakisphosphate kinase 1 regulates neutrophil function in innate immunity by inhibiting phosphatidylinositol-(3,4,5)-trisphosphate signaling. Nat Immunol 12, 752-760 (2011).
2. M. R. Looney, J. X. Nguyen, Y. Hu, J. A. Van Ziffle, C. A. Lowell, M. A. Matthay, Platelet depletion and aspirin treatment protect mice in a two-event model of transfusion-related acute lung injury. J Clin Invest 119, 3450-3461 (2009).
3. G. Ortiz-Munoz, B. Mallavia, A. Bins, M. Headley, M. F. Krummel, M. R. Looney, Aspirin-triggered 15-epi-lipoxin A4 regulates neutrophil-platelet aggregation and attenuates acute lung injury in mice. Blood 124, 2625-2634 (2014).
4. R. E. Abdulnour, J. Dalli, J. K. Colby, N. Krishnamoorthy, J. Y. Timmons, S. H. Tan, R. A. Colas, N. A. Petasis, C. N. Serhan, B. D. Levy, Maresin 1 biosynthesis during platelet-neutrophil interactions is organ-protective. Proc Natl Acad Sci USA 111, 16526-16531 (2014).
5. A. Zarbock, K. Singbartl, K. Ley, Complete reversal of acid-induced acute lung injury by blocking of platelet-neutrophil aggregation. J Clin Invest 116, 3211-3219 (2006).
6. M. Asaduzzaman, M. Rahman, B. Jeppsson, H. Thorlacius, P-selectin glycoprotein-ligand-1 regulates pulmonary recruitment of neutrophils in a platelet-independent manner in abdominal sepsis. Br J Pharmacol 156, 307-315 (2009).
7. Y. Li, Y. Jia, M. Pichavant, F. Loison, B. Sarraj, A. Kasorn, J. You, B. E. Robson, D. T. Umetsu, J. P. Mizgerd, K. Ye, H. R. Luo, Targeted deletion of tumor suppressor PTEN augments neutrophil function and enhances host defense in neutropenia-associated pneumonia. Blood 113, 4930-4941 (2009).

8. M. W. Laschke, S. Dold, M. D. Menger, B. Jeppsson, H. Thorlacius, Platelet-dependent accumulation of leukocytes in sinusoids mediates hepatocellular damage in bile duct ligation-induced cholestasis. Br J Pharmacol 153, 148-156 (2008).
9. P. von Hundelshausen, C. Weber, Platelets as immune cells: bridging inflammation and cardiovascular disease. Circ Res 100, 27-40 (2007).
10. K. Singbartl, S. B. Forlow, K. Ley, Platelet, but not endothelial, P-selectin is critical for neutrophil-mediated acute postischemic renal failure. FASEB J 15, 2337-2344 (2001).
11. K. Jurk, B. E. Kehrel, Platelets: physiology and biochemistry. Seminars in thrombosis and hemostasis 31, 381-392 (2005).
12. Y. Li, A. Prasad, Y. Jia, S. G. Roy, F. Loison, S. Mondal, P. Kocjan, L. E. Silberstein, S. Ding, H. R. Luo, Pretreatment with phosphatase and tensin homolog deleted on chromosome 10 (PTEN) inhibitor SF1670 augments the efficacy of granulocyte transfusion in a clinically relevant mouse model. Blood 117, 6702-6713 (2011).
13. S. Ghosh, D. Shukla, K. Suman, B. J. Lakshmi, R. Manorama, S. Kumar, R. Bhandari, Inositol hexakisphosphate kinase 1 maintains hemostasis in mice by regulating platelet polyphosphate levels. Blood 122, 1478-1486 (2013).
14. F. Muller, N. J. Mutch, W. A. Schenk, S. A. Smith, L. Esterl, H. M. Spronk, S. Schmidbauer, W. A. Gahl, J. H. Morrissey, T. Renne, Platelet polyphosphates are proinflammatory and procoagulant mediators in vivo. Cell 139, 1143-1156 (2009).
15. J. S. Bae, W. Lee, A. R. Rezaie, Polyphosphate elicits pro-inflammatory responses that are counteracted by activated protein C in both cellular and animal models. Journal of thrombosis and haemostasis: JTH 10, 1145-1151 (2012).
16. J. H. Morrissey, S. H. Choi, S. A. Smith, Polyphosphate: an ancient molecule that links platelets, coagulation, and inflammation. Blood 119, 5972-5979 (2012).
17. S. A. Smith, J. H. Morrissey, Polyphosphate: a new player in the field of hemostasis. Curr Opin Hematol 21, 388-394 (2014).
18. P. G. McLean, A. Ahluwalia, M. Perretti, Association between kinin B(1) receptor expression and leukocyte trafficking across mouse mesenteric postcapillary venules. J Exp Med 192, 367-380 (2000).
19. A. Ahluwalia, M. Perretti, Involvement of bradykinin B1 receptors in the polymorphonuclear leukocyte accumulation induced by IL-1 beta in vivo in the mouse. J Immunol 156, 269-274 (1996).
20. C. D. Figueroa, C. E. Matus, F. Pavicic, J. Sarmiento, M. A. Hidalgo, R. A. Burgos, C. B. Gonzalez, K. D. Bhoola, P. Ehrenfeld, Kinin B1 receptor regulates interactions between neutrophils and endothelial cells by modulating the levels of Mac-1, LFA-1 and intercellular adhesion molecule-1. Innate immunity 21, 289-304 (2015).
21. T. Chavakis, S. Santoso, K. J. Clemetson, U. J. Sachs, I. Isordia-Salas, R. A. Pixley, P. P. Nawroth, R. W. Colman, K. T. Preissner, High molecular weight kininogen regulates platelet-leukocyte interactions by bridging Mac-1 and glycoprotein Ib. J Biol Chem 278, 45375-45381 (2003).
22. A. Chakraborty, The inositol pyrophosphate pathway in health and diseases. Biological reviews of the Cambridge Philosophical Society, (2017).
23. B. Sarraj, S. Massberg, Y. Li, A. Kasorn, K. Subramanian, F. Loison, L. E. Silberstein, U. von Andrian, H. R. Luo, Myeloid-specific deletion of tumor suppressor PTEN augments neutrophil transendothelial migration during inflammation. J Immunol 182, 7190-7200 (2009).
24. S. Mondal, K. K. Subramanian, J. Sakai, B. Bajrami, H. R. Luo, Phosphoinositide lipid phosphatase SHIP1 and PTEN coordinate to regulate cell migration and adhesion. Mol Biol Cell 23, 1219-1230 (2012).
25. A. Zarbock, R. K. Polanowska-Grabowska, K. Ley, Platelet-neutrophil-interactions: linking hemostasis and inflammation. Blood Rev 21, 99-111 (2007).
26. N. Sheng, M. B. Fairbanks, R. L. Heinrikson, G. Canziani, I. M. Chaiken, D. M. Mosser, H. Zhang, R. W. Colman, Cleaved high molecular weight kininogen binds directly to the integrin CD11b/CD18 (Mac-1) and blocks adhesion to fibrinogen and ICAM-1. Blood 95, 3788-3795 (2000).
27. T. Chavakis, S. M. Kanse, R. A. Pixley, A. E. May, I. Isordia-Salas, R. W. Colman, K. T. Preissner, Regulation of leukocyte recruitment by polypeptides derived from high molecular weight kininogen. FASEB J 15, 2365-2376 (2001).
28. K. Yoshida, R. Kondo, Q. Wang, C. M. Doerschuk, Neutrophil cytoskeletal rearrangements during capillary sequestration in bacterial pneumonia in rats. Am J Respir Crit Care Med 174, 689-698 (2006).
29. M. Asaduzzaman, S. Lavasani, M. Rahman, S. Zhang, O. O. Braun, B. Jeppsson, H. Thorlacius, Platelets support pulmonary recruitment of neutrophils in abdominal sepsis. Crit Care Med 37, 1389-1396 (2009).
30. H. J. Kwak, P. Liu, B. Bajrami, Y. Xu, S. Y. Park, C. Nombela-Arrieta, S. Mondal, Y. Sun, H. Zhu, L. Chai, L. E. Silberstein, T. Cheng, H. R. Luo, Myeloid cell-derived reactive oxygen species externally regulate the proliferation of myeloid progenitors in emergency granulopoiesis. Immunity 42, 159-171 (2015).
31. F. Loison, H. Zhu, K. Karatepe, A. Kasorn, P. Liu, K. Ye, J. Zhou, S. Cao, H. Gong, D. E. Jenne, E. Remold-O'Donnell, Y. Xu, H. R. Luo, Proteinase 3-dependent caspase-3 cleavage modulates neutrophil death and inflammation. J Clin Invest 124, 4445-4458 (2014).

What is claimed herein is:

1. A method of reducing neutrophil recruitment to the lung of a subject in need thereof, the method comprising administering to the subject an inhibitor of inositol hexakisphosphate kinase 1 (IP6K1).

2. A method of treating or preventing a lung infection or lung inflammatory condition in a subject in need thereof, the method comprising administering to the subject an inhibitor of inositol hexakisphosphate kinase 1 (IP6K1).

3. The method of claim 2, wherein the infection is bacterial pneumonia.

4. The method of claim 2, wherein the subject is a subject with or determined to have pulmonary neutrophil accumulation.

5. The method of claim 2, wherein the subject is a subject with or determined to have increased inorganic polyphosphate (polyP) levels.

6. The method of claim 2, wherein the subject is a subject with or determined to have increased serum inorganic polyphosphate (polyP) levels.

7. The method of claim 2, wherein the inhibitor is an inhibitory nucleic acid.

8. The method of claim 2, wherein the inhibitor is TNP [N2-(m-(trifluoromethyl)benzyl) N6-(p-nitrobenzyl)purine].

9. The method of claim 2, wherein the inhibitor is administered in a composition which further comprises a platelet-targeting molecule.

10. The method of claim 1, wherein the inhibitor is an inhibitory nucleic acid.

11. The method of claim 1, wherein the inhibitor is TNP [N2-(m-(trifluoromethyl)benzyl) N6-(p-nitrobenzyl)purine].

12. The method of claim 1, wherein the inhibitor is administered in a composition which further comprises a platelet-targeting molecule.

* * * * *